United States Patent
Chen et al.

(10) Patent No.: US 9,884,815 B2
(45) Date of Patent: Feb. 6, 2018

(54) PGAM1 INHIBITORS AND METHODS RELATED THERETO

(71) Applicant: EMORY UNIVERSITY, Atlanta, GA (US)

(72) Inventors: Jing Chen, Atlanta, GA (US); Taro Hitosugi, Decatur, GA (US); Sumin Kang, Decatur, GA (US)

(73) Assignee: Emory University, Atlanta, GA (US)

(*) Notice: Subject to any disclaimer, the term of this patent is extended or adjusted under 35 U.S.C. 154(b) by 535 days.

(21) Appl. No.: 14/349,550

(22) PCT Filed: Oct. 11, 2012

(86) PCT No.: PCT/US2012/059740
§ 371 (c)(1),
(2) Date: Sep. 23, 2014

(87) PCT Pub. No.: WO2013/055913
PCT Pub. Date: Apr. 18, 2013

(65) Prior Publication Data
US 2014/0294818 A1    Oct. 2, 2014

Related U.S. Application Data

(60) Provisional application No. 61/547,278, filed on Oct. 14, 2011.

(51) Int. Cl.
| | | |
|---|---|---|
| *C07K 16/40* | (2006.01) | |
| *C08F 212/32* | (2006.01) | |
| *A61K 31/18* | (2006.01) | |
| *C07C 311/29* | (2006.01) | |
| *C09B 1/06* | (2006.01) | |
| *C09B 1/12* | (2006.01) | |
| *A61K 45/06* | (2006.01) | |

(52) U.S. Cl.
CPC ............ *C07C 311/29* (2013.01); *A61K 31/18* (2013.01); *A61K 45/06* (2013.01); *C07K 16/40* (2013.01); *C09B 1/06* (2013.01); *C09B 1/12* (2013.01); *C07C 2603/24* (2017.05); *C07K 2317/34* (2013.01)

(58) Field of Classification Search
None
See application file for complete search history.

(56) References Cited

U.S. PATENT DOCUMENTS

| | | | | |
|---|---|---|---|---|
| 2,394,918 A * | 2/1946 | Kienle | ...................... | D06P 1/22 |
| | | | | 552/222 |
| 6,576,660 B1 * | 6/2003 | Liao | ........................ | A61K 31/00 |
| | | | | 514/337 |
| 6,620,858 B2 * | 9/2003 | Cyr | .......................... | C08F 20/38 |
| | | | | 522/103 |

FOREIGN PATENT DOCUMENTS

| | | | | |
|---|---|---|---|---|
| JP | 2008201699 | | 4/2008 | |
| WO | WO 9214454 A1 * | | 9/1992 | ............. A61K 31/04 |
| WO | 2010082912 | | 7/2010 | |

OTHER PUBLICATIONS

Patani et al. ("Patani", Chem. Rev, 1996, 96, 3147-3176).*
Hitosugi et al. Phosphoglycerate Mutase 1 Coordinates Glycolysis and Biosynthesis to Promote Tumor Growth, Cancer Cell 22, 585-600, 2012.
Qu et al. Phosphoglycerate mutase 1 regulates dNTP pool and promotes homologous recombination repair in cancer cells, J Cell Biol, 2017, 1-16.

* cited by examiner

*Primary Examiner* — Mark Halvorson
*Assistant Examiner* — Kauser Akhoon
(74) *Attorney, Agent, or Firm* — Emory Patent Group

(57) ABSTRACT

In certain embodiments, the disclosure relates to methods of treating or preventing a PGAM1 mediated condition such as cancer or tumor growth comprising administering an effective amount of PGAM1 inhibitor, for example, an anthracene-9,10-dione derivative to a subject in need thereof. In certain embodiments, the disclosure relates to methods of treating or preventing cancer, such as lung cancer, head and neck cancer, and leukemia, comprising administering a therapeutically effective amount of a pharmaceutical composition comprising a compound disclosed herein or pharmaceutically acceptable salt to a subject in need thereof.

18 Claims, 34 Drawing Sheets

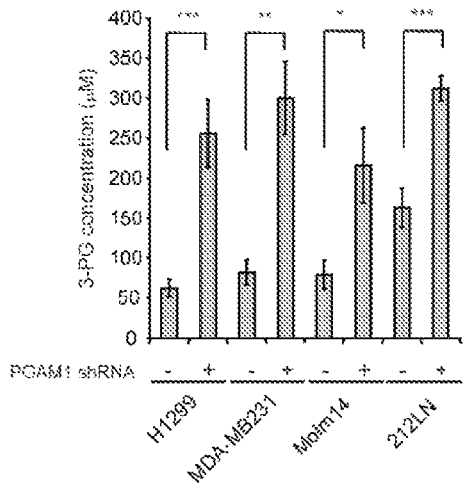
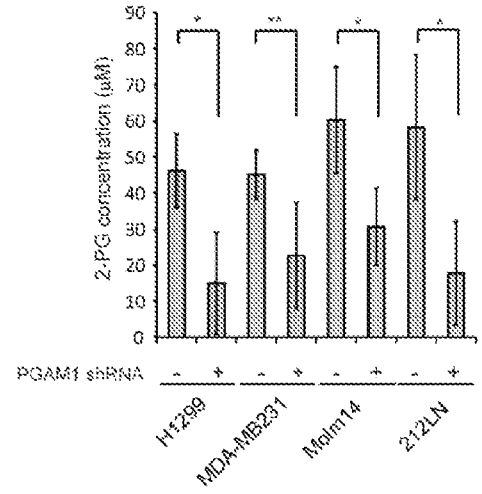
FIG. 1A          FIG. 1B
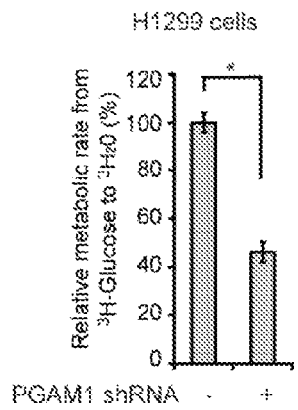
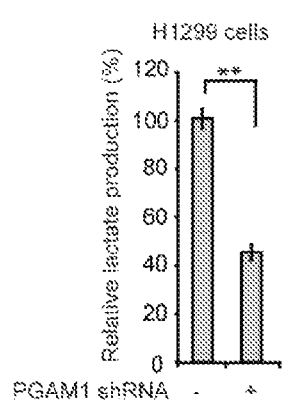
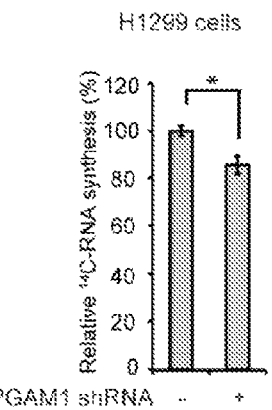
FIG. 1C          FIG. 1D          FIG. 1E
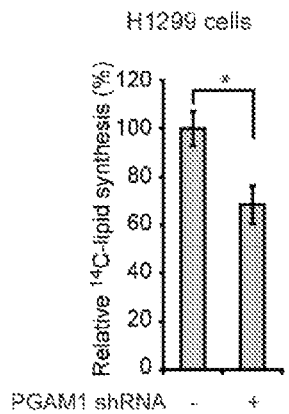
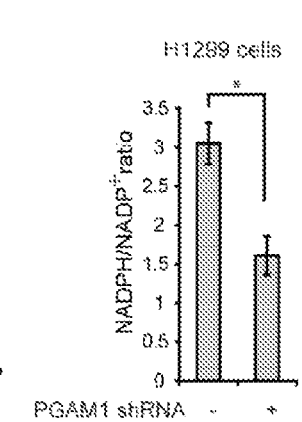
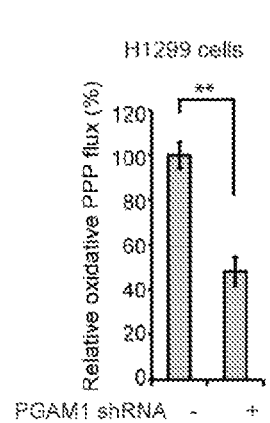
FIG. 1F          FIG. 1G          FIG. 1H

FIG. 1I  FIG. 1J

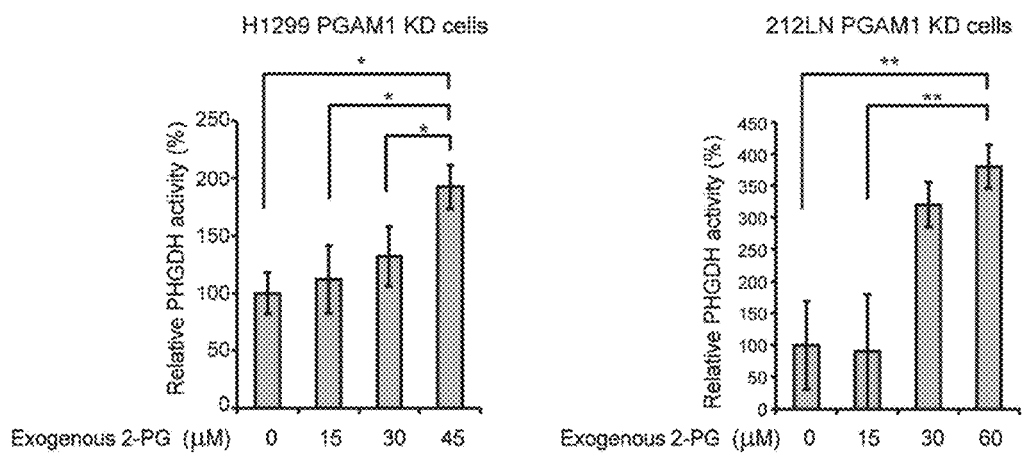
FIG. 5B
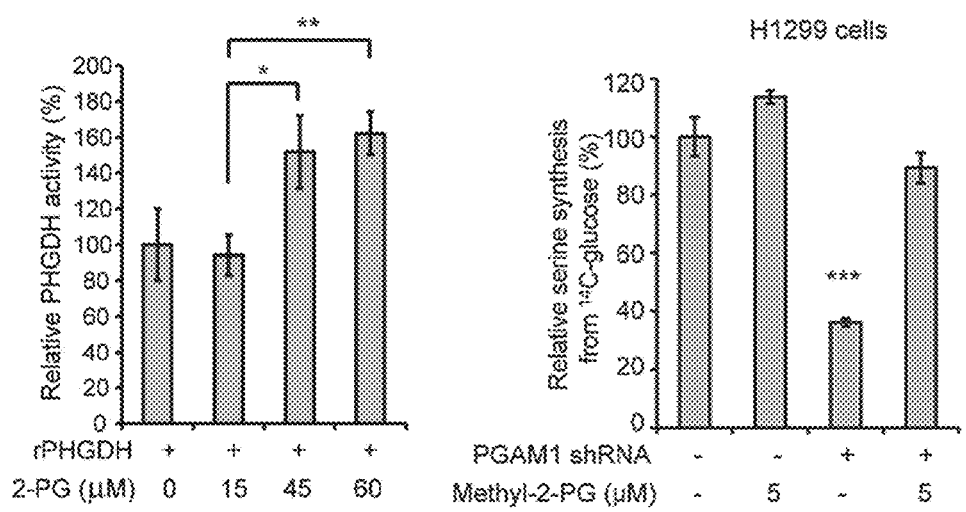
FIG. 5C
FIG. 5D

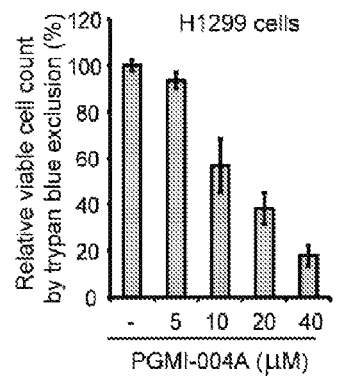
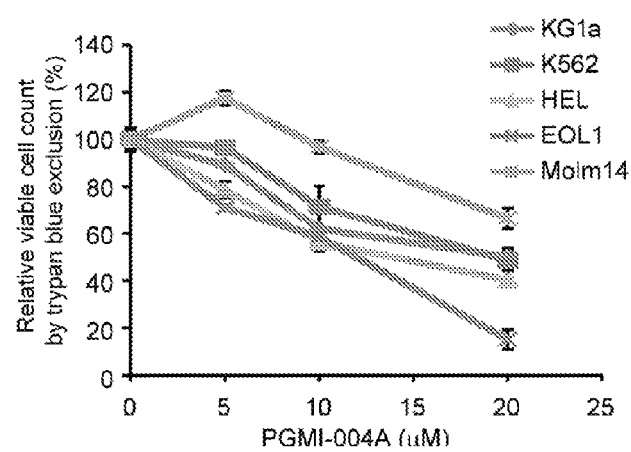
FIG. 7I    FIG. 7J
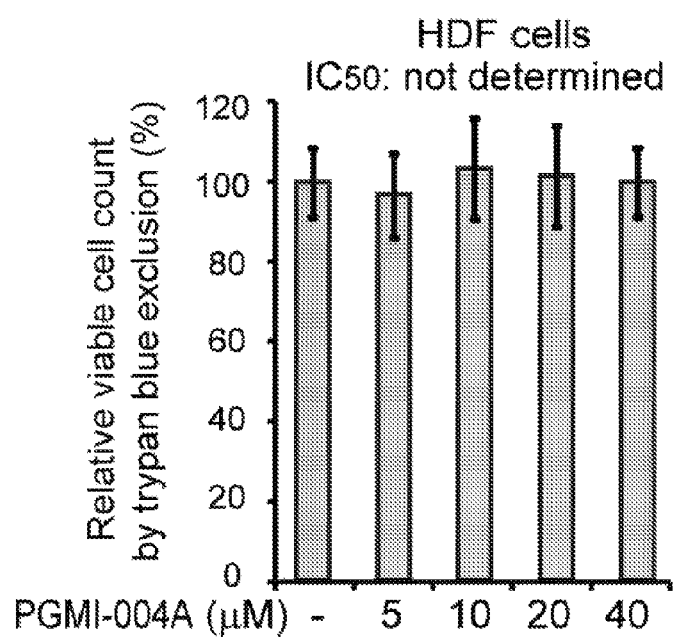
FIG. 7K

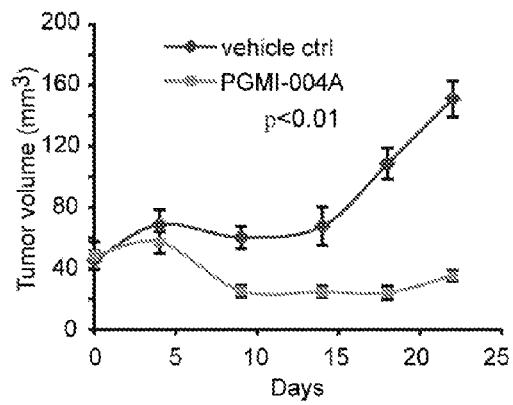
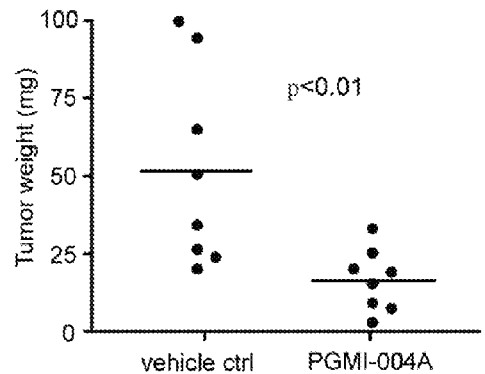
FIG. 8A
FIG. 8B
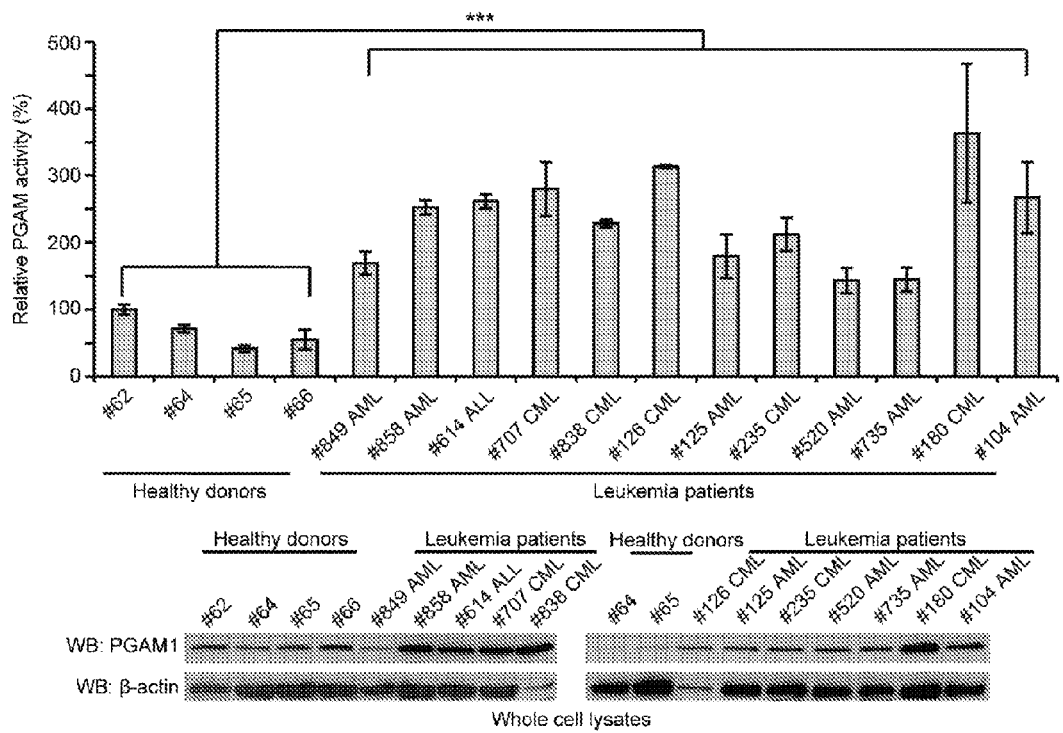
FIG. 8C

FIG. 12CFIG. 12D

PGAM1 INHIBITORS AND METHODS RELATED THERETO

CROSS REFERENCE TO RELATED APPLICATIONS

This application claims priority to U.S. Provisional Application No. 61/547,278 filed Oct. 14, 2011, hereby incorporated by reference in its entirety.

BACKGROUND

There remains a need for improved therapeutics useful in the treatment of cancer. The Warburg effect in cancer cells consists of an increase in aerobic glycolysis and enhanced lactate production, which generates more ATPs more quickly than in normal cells that overwhelmingly rely on oxidative phosphorylation. In addition, tumor tissue traps more glucose than normal tissue does, as cancer cells use elevated amounts of glucose as a carbon source for anabolic biosynthesis of macromolecules. These include nucleotides, amino acids and fatty acids, to produce RNA/DNA, proteins and lipids, respectively, which are used for cell proliferation and to fulfill the request of the rapidly growing tumors. Interestingly, leukemia cells are also highly glycolytic, despite that such cells reside within the bloodstream at higher oxygen tensions than cells in most normal tissues, as well as tumor cells that commonly reside in hypoxia. This suggests that tumor hypoxia may not be a major contributor to select for cells dependent on anaerobic metabolism.

During glycolysis, glycolytic intermediates including glucose-6-phosphate (G6P) can be diverted into the pentose phosphate pathway (PPP), which contributes to macromolecular biosynthesis by producing reducing potential in the form of reduced nicotinamide adenine dinucleotide phosphate (NADPH) and/or ribose-5-phosphate (R5P), the building blocks for nucleotide synthesis. NADPH is the most crucial metabolite produced by the PPP because NADPH not only fuels macromolecular biosynthesis such as lipogenesis, but it also functions as a crucial antioxidant, quenching the reactive oxygen species (ROS) produced during rapid proliferation of cancer cells.

Glycolysis and glutaminolysis supply the carbon input required for the TCA cycle to function as a biosynthetic 'hub' and permits the production of other macromolecules including amino acids and fatty acids. Thus, cancer cells appear to coordinate glycolysis and anabolism to provide an overall metabolic advantage to cancer cell proliferation and disease development.

Engel et al., report that a phosphoglycerate mutase-derived polypeptide inhibits glycolytic flux and induces cell growth arrest in tumor cell lines. J Biol Chem, 2004, 279, 35803-35812.

Evans et al., report the mechanistic and structural requirements for active site labeling of phosphoglycerate mutase by spiroepoxides. See Mol. BioSyst., 2007, 3, 495-506.

PCT Patent Application PCT/US2009/000257, published as WO 2010/082912 A1 discloses certain disulfonamide derivatives. The disclosure also discloses methods for treating tumors and cancer.

SUMMARY

In certain embodiments, the disclosure relates to methods of treating or preventing a PGAM1 mediated condition such as cancer or tumor growth comprising administering an effective amount of PGAM1 inhibitor, for example, an anthracene-9,10-dione derivative to a subject in need thereof.

In certain embodiments, the anthracene-9,10-dione derivative is a compound of Formula I,

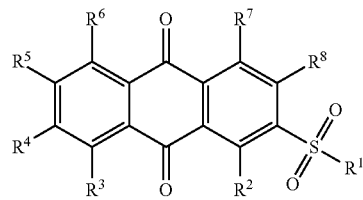

Formula I prodrug, ester, or salt thereof, wherein:
$R^1$, $R^2$, $R^3$, $R^4$, $R^5$, $R^6$, $R^7$ and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, $R^4$, $R^5$, $R^6$, $R^7$, and $R^8$ are optionally substituted with one or more, the same or different, $R^9$;

$R^9$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein $R^9$ is optionally substituted with one or more, the same or different, $R^{11}$;

$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In some embodiments, the disclosure relates to compounds of Formula I or salts thereof, wherein $R^7$ is hydroxyl.

In some embodiments, the disclosure relates to compounds of Formula I or salts thereof, wherein $R^8$ is hydroxyl.

In some embodiments, the disclosure relates to compounds of Formula I or salts thereof, wherein $R^1$ is amino wherein $R^1$ is optionally substituted with one or more, the same or different, $R^9$.

In some embodiments, the disclosure relates to compounds of Formula I or salts thereof, wherein $R^1$ is amino and is substituted with an aryl ring, wherein the aryl ring is optionally substituted with one or more, the same or different $R^{10}$.

In some embodiments, the disclosure relates to compounds of Formula I or salts thereof, wherein $R^1$ is amino and is substituted with an aryl ring, wherein the aryl ring substituted in the para position with an alkyl, wherein the alkyl group is optionally substituted with one or more, the same or different $R^{11}$.

In some embodiments, the disclosure relates to compounds of Formula I or salts thereof, wherein $R^1$ is amino and is substituted with an aryl ring, wherein the aryl ring substituted in the para position with a methyl, wherein the methyl group is optionally substituted with one or more, the same or different $R^{11}$.

In some embodiments, the disclosure relates to compounds of Formula I or salts thereof, wherein $R^1$ is amino and is substituted with an aryl ring, wherein the aryl ring substituted in the para position with a methyl, wherein the methyl group is substituted with one or more, the same or different halogens.

In some embodiments the disclosure relates to compounds of Formula I or salts thereof, wherein $R^1$ is amino and is substituted with an aryl ring, wherein the aryl ring substituted in the para position with trifluoromethane.

In certain embodiments, the derivative is 3,4-dihydroxy-9,10-dioxo-9,10-dihydroanthracene-2-sulfonic acid or 3,4-dihydroxy-9,10-dioxo-N-(4-(trifluoromethyl)phenyl)-9,10-dihydroanthracene-2-sulfonamide prodrug, ester, or salt thereof optionally substituted with one or more, the same or different, substituent(s).

In certain embodiments, the compound comprises a Log P of greater than 2, 3, or 4.

In some embodiments, the disclosure relates to pharmaceutical compositions of compounds of Formula I or salts thereof.

In some embodiments, the disclosure relates to pharmaceutical compositions of compounds of Formula I containing a pharmaceutically acceptable excipient or a pharmaceutically acceptable salt thereof.

In some embodiments, the disclosure relates to pharmaceutical compositions of compounds of Formula I containing a pharmaceutically acceptable excipient or a pharmaceutically acceptable salt thereof and a second therapeutic agent.

In some embodiments, the disclosure relates to a method of treating or preventing cancer comprising by administering a pharmaceutical composition of Formula I to a subject diagnosed with, exhibiting symptoms of, or at risk of cancer.

In some embodiments, the disclosure relates to a method of treating or preventing cancer comprising by administering a pharmaceutical composition of Formula I to a subject diagnosed with, exhibiting symptoms of, or at risk of cancer wherein the pharmaceutical compositions is administered in combination with a second chemotherapeutic agent.

In some embodiments, the disclosure relates to a method of treating or preventing cancer comprising by administering a pharmaceutical composition of Formula I to a subject diagnosed with, exhibiting symptoms of, or at risk of cancer in combination with a second anti-cancer agent such as gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In some embodiments, the disclosure relates to a method of treating or preventing cancer comprising by administering a pharmaceutical composition of Formula I to a subject diagnosed with, exhibiting symptoms of, or at risk of cancer wherein the cancer is selected from the group consisting of leukemia, cervical, ovarian, colon, breast, gastric, lung, skin, ovarian, pancreatic, prostate, head, neck, and renal cancer.

In some embodiments, the disclosure relates to the use of a compound of Formula I in the production of a medicament for the treatment or prevention of cancer.

In certain embodiments, the disclosure relates to an antibody that binds the PGAM1 phospho-Y26 epitope. In certain embodiments the antibody is a human chimera or a humanized antibody that binds PGAM1 phospho-Y26 epitope. In certain embodiments, the disclosure contemplates the use of a pharmaceutical composition comprising an antibody that binds PGAM1 phospho-Y26 epitope in the treatment of cancer in combination with other anti-cancer agent by administering an effective amount to a subject in need thereof.

In certain embodiments, the disclosure also relates to the method of synthesis of compounds disclosed herein.

BRIEF DESCRIPTION OF THE FIGURES

FIGS. 1A-L show data indicating PGAM1 controls intracellular 3-PG and 2-PG levels in cancer cells and is important for glycolysis and anabolic biosynthesis, as well as cell proliferation and tumor growth. (A-B) Intracellular concentrations of 3-PG and 2-PG were determined in diverse PGAM1 knockdown cancer cells and compared to control cells. (C-J) H1299 cells with stable knockdown of PGAM1 and control cells harboring an empty vector were tested for glycolytic rate (C), lactate production (D), RNA biosynthesis (E), lipogenesis (F), NADPH/NADP+ ratio (G), and oxidative PPP flux (H). The intracellular ATP levels (I) and oxygen consumption rate (J) in the presence or absence of 100 nM oligomycin (ATP synthase inhibitor) were also tested. (K) Cell proliferation rates were determined by cell counting in diverse human cancer (H1299, 212LN and MDA-MB231) and leukemia (KG1a, Molm14 and K562) cells with stable knockdown of PGAM1, which were normalized to the corresponding control cells harboring an empty vector. (L) Stable knockdown of PGAM1 by shRNA attenuates tumor growth potential of H1299 cells in xenograft nude mice. Left: Dissected tumors (indicated by red arrows) in a representative nude mouse and expression of PGAM1 in tumor lysates are shown. Right: PGAM1 knockdown cells show significantly reduced tumor formation in xenograft nude mice compared to cells harboring empty vector control.

FIGS. 5A-H show data indicating rescue of reduced 2-PG levels due to PGAM1 attenuation results in decreased 3-PG levels by activating PHGDH. (A) 3-PG levels in diverse cancer cells with stable knockdown of PGAM1 were determined in the presence and absence of methyl-2-PG. (B-C) Enzyme activity of PHGDH in PGAM1 knockdown H1299 (B; left) or 212LN (B; right) cell lysates and recombinant PHGDH (rPHGDH) (C) were determined in the presence of increasing concentrations of 2-PG. Relative enzyme activity was normalized to the control samples without 2-PG treatment. 2-PG levels in control H1299 cells with empty vector and PGAM1 knockdown cells are 46.2±10.2 μM and 15.0±14.1 μM, respectively, while 2-PG levels in 212LN cells with empty vector and stable knockdown of PGAM1 are 58.3±20.1 μM and 17.8±14.4 μM, respectively. (D) Serine biosynthesis rate of H1299 cells with stable knockdown of PGAM1 was determined by measuring 14C incorporation into serine from 14C-glucose in the presence and absence of methyl-2-PG. Relative serine biosynthesis was normalized to control cells harboring an empty vector without methyl-2-PG treatment. (E) Western blot result shows shRNA-mediated knockdown of PHGDH in H1299 cells with stable knockdown of PGAM1 in the presence or absence of methyl-2-PG treatment. (F) 2-PG (left) and 3-PG (right) levels in PGAM1 knockdown cells upon PHGDH knockdown were determined in the presence and absence of methyl-2-PG. (G-H) PGAM1 stable knockdown cells treated with or without shRNA targeting PHGDH were tested for PPP flux (G) as well as biosynthesis of serine, lipids and RNA (H; left, middle and right, respectively) in the presence and absence of methyl-2-PG.

FIGS. 7A-K show data indicating inhibition of PGAM1 by PGMI-004A reveals that PGAM1 enzyme activity is important for regulation of 3-PG and 2-PG levels and coordination of glycolysis and biosynthesis to promote cancer cell proliferation. (A) 2-PG (left) and 3-PG (right) levels in H1299 cells treated with or without PGMI-004A were determined in the presence and absence of methyl-2-PG. (B-C) Lactate production (B) and intracellular ATP levels (C) in H1299 cells treated with or without PGMI-004A were determined in the presence and absence of methyl-2-PG. (D-E) H1299 cells treated with or without PGMI-004A were tested for oxidative PPP flux (D) and NADPH/NADP+ ratio (E). (F-H) H1299 cells treated with or without PGMI-004A were tested for biosynthesis of lipids (F) and RNA (G), as well as cell proliferation (H) in the presence and absence of methyl-2-PG. (I-K) Cell viability of H1299 cells (I), diverse human leukemia cells (J) and control human dermal fibroblasts (HDF) cells (K) in the presence of increasing concentrations of PGMI-004A. Cell viability was determined by trypan blue exclusion.

FIGS. 8A-I show data indicating that PGMI-004A treatment results in increased 3-PG and decreased 2-PG levels, and reduced cell proliferation of primary leukemia cells from human patients, as well as attenuated tumor growth in xenograft nude mice in vivo. (A-B) Tumor growth (A) and tumor size (B) in xenograft nude mice injected with H1299 cells were compared between the group of mice treated with PGMI-004A and the control group treated with vehicle control. p values were determined by a two-tailed Student's t test. (C) PGAM1 protein expression (lower) and enzyme activity (upper) levels were examined using primary leukemia cells from diverse human patients with AML, CML and B-ALL and compared to control peripheral blood cells from healthy donors. (D) Effect of PGMI-004A treatment on 3-PG (left) and 2-PG (right) levels in human primary leukemia cells isolated from peripheral blood samples from a representative AML patient. (E) Effect of PGMI-004A treatment on cell viability (left), PGAM1 activity (middle) and lactate production (right) in human primary leukemia cells from a representative CML patient. (F-G) Effect of methyl-2-PG treatment on decreased cell viability (F; G left) and lactate production (G right) in PGMI-004A-treated human primary leukemia cells from AML patients. (H-I) PGMI-004A shows no toxicity in treatment (120 h) of peripheral blood cells (H) and CD34+ cells isolated from bone marrow samples (I) from representative healthy human donors.

FIGS. 12A-F show data indicating PGMI-004A effectively inhibits tumor growth in xenograft nude mice and cell viability of primary leukemia cells from human patients. (A-D) Histological morphology of hematoxylin-eosin stained tissue sections of representative nude mice in PGMI-004A or vehicle control-treated groups (#39 and #46, respectively). Nude mice were treated daily with PGMI-004A (100 mg/kg/day) intraperitoneally for 7 days. Peripheral blood samples were collected and applied for analysis of hematological properties. The vital organs were collected for histo-pathological analysis. Histopathologic tissue sections (kidney, lung, liver and spleen) from representative nude mice stained with hematoxylin-eosin did not reveal significant differences between the vehicle and PGMI-004A treated groups. Images were analyzed and captured using ImageScope software (Aperio Technologies Inc.) without any additional or subsequent image processing (high power images are 20×; low power images are either 4.0×, 4.2×, or 4.4×). Scale bars are indicated. (E) Dissected tumors (indicated by arrows) in representative nude mice treated with vehicle control or PGMI-004A are shown. (F) Tumors from two groups of xenograft nude mice treated with either vehicle control or PGMI-004A are shown.

DETAILED DESCRIPTION

Figure 1K:
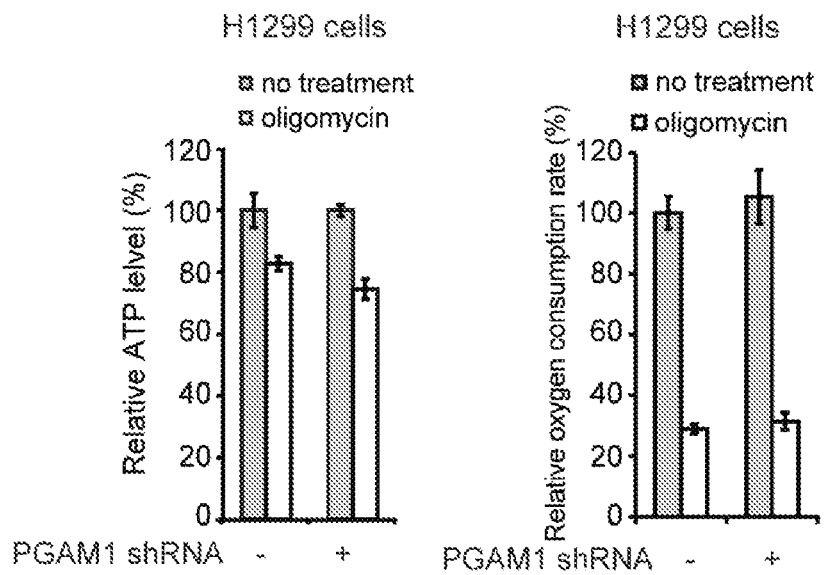

The Warburg effect in cancer cells consists of increased aerobic glycolysis and enhanced lactate production, which generates more ATPs more quickly than in normal cells that overwhelmingly rely on oxidative phosphorylation. In addition, cancer cells use glycolytic intermediates for anabolic biosynthesis of macromolecules. These include nucleotides, amino acids and fatty acids, to produce RNA/DNA, proteins and lipids, respectively, which are necessary for cell proliferation and to fulfill the request of the rapidly growing tumors.

PGAM1 converts 3-phosphoglycerate (3-PG) to 2-phosphoglycerate (2-PG) during glycolysis. This is a unique step in glycolysis as most of the glycolytic intermediates that are used as precursors for anabolic biosynthesis are upstream of this step. In many cancers, including hepatocellular carcinoma and colorectal cancer, PGAM1 activity is increased compared to that in the normal tissues. PGAM1 gene expression is believed to be upregulated due to loss of TP53 in cancer cells, as TP53 negatively regulates PGAM1 gene expression.

Inhibition of PGAM1 results in increased 3-PG and decreased 2-PG levels in cancer cells, leading to significantly decreased PPP flux and biosynthesis, and consequently reduced cell proliferation and tumor growth. Y26 phosphorylation of PGAM1 is common in human leukemias. Leukemogenic tyrosine kinases (LTKs) are constitutively activated and frequently implicated in pathogenesis of human leukemias, including FGFR1 fusions associated 8p11 stem cell MPD, BCR-ABL associated CML, FLT3-ITD associated AML and JAK2 V617F associated myeloproliferative disorders. Y26 phosphorylation activates PGAM1 by promoting His11 phosphorylation and contributes to control of 3-PG and 2-PG levels, providing a novel, acute mechanism underlying PGAM1 upregulation in addition to chronic changes regulated by TP53. Shutting off or forced activation of glycolytic enzymes may disrupt not only energy production but also supplies of metabolic intermediates as precursors for anabolism, both of which are required for cancer cells to survive, grow and proliferate.

PGAM1 protein expression, Y26 phosphorylation and enzyme activity levels are upregulated in human primary leukemia cells compared with normal peripheral blood cells from healthy donors. Disclosed herein are certain PGAM1 inhibitors which effectively inhibit cancer/leukemia cell proliferation, tumor growth in xenograft nude mice.

Terms

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It can also be identified by a change in relevant biomarker or gene expression profile, such as PSA for prostate cancer, HER2 for breast cancer, or others.

The half maximal inhibitory concentration (IC$_{50}$) refers to a measure of the effectiveness of a compound in inhibiting biological or biochemical function. This quantitative measure indicates how much of a particular drug or other substance (inhibitor) is needed to inhibit a given biological process (or component of a process, i.e. an enzyme, cell, cell receptor or microorganism) by half.

The partition coefficient is a ratio of concentrations of un-ionized compound between the two solutions. To measure the partition coefficient of ionizable solutes, the pH of the aqueous phase is adjusted such that the predominant form of the compound is un-ionized. The logarithm of the ratio of the concentrations of the un-ionized solute in the solvents (octane/water) refers to the log P. The log P value is a measure of lipophilicity.

Phosphoglycerate Mutase 1 (PGAM1) PGAM1 Coordinates Glycolysis and Biosynthesis to Promote Tumor Growth Cancer cells coordinate glycolysis and biosynthesis to support rapidly growing tumors Experiments herein indicate that glycolytic enzyme phosphoglycerate mutase 1 (PGAM1), commonly upregulated in human cancers due to loss of TP53, contributes to biosynthesis regulation in part by controlling intracellular levels of its substrate 3-phosphoglycerate (3-PG) and product 2-phosphoglycerate (2-PG). 3-PG binds to and inhibits 6-phosphogluconate dehydrogenase in the oxidative pentose phosphate pathway (PPP), while 2-PG activates 3-phosphoglycerate dehydrogenase to provide feedback control of 3-PG levels. Inhibition of PGAM1 by shRNA or a small molecule inhibitors, such as PGMI-004A, results in increased 3-PG and decreased 2-PG levels in cancer cells, leading to significantly decreased glycolysis, PPP flux and biosynthesis, as well as attenuated cell proliferation and tumor growth.

Figure 3:
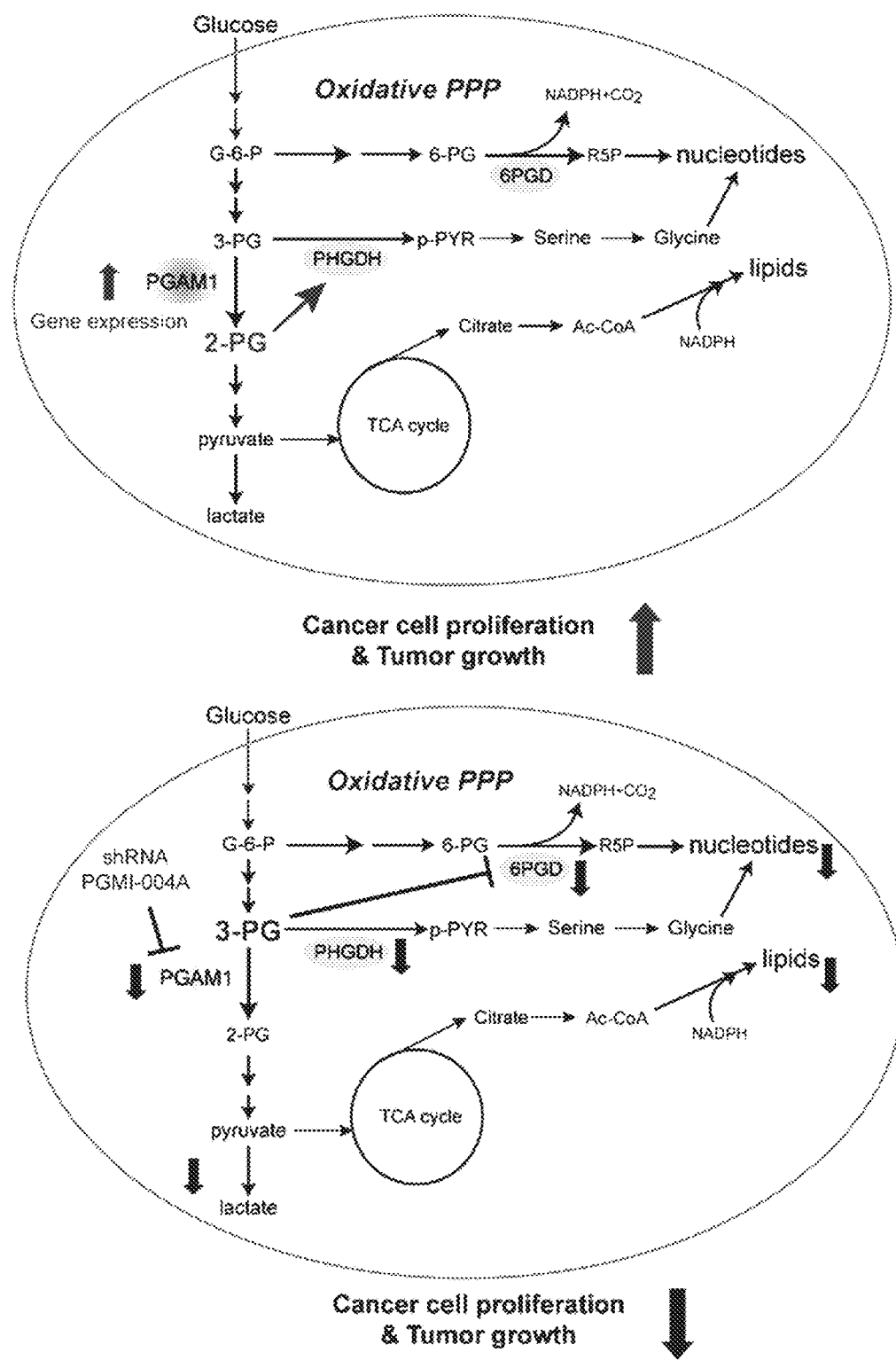
FIG. 3 illustrates a proposed model: role of PGAM1 in cancer cell metabolism. Top: PGAM1 activity is upregulated in cancer cells to promote glycolysis and keep the intracellular 3-PG levels low, which in turn permits high levels of the PPP and biosynthesis to fulfill the request of rapidly growing tumors. PGAM1 also maintains the physiological levels of 2-PG to sustain PHGDH activity, which diverts 3-PG from glycolysis to serine synthesis and contributes to maintaining relatively low levels of 3-PG in cancer cells. These effects in concert provide a metabolic advantage to cancer cell proliferation and tumor growth. Bottom: When PGAM1 is inhibited, 3-PG levels are elevated, which in turn inhibit 6PGD and consequently the oxidative PPP and anabolic biosynthesis. At the same time, 2-PG is decreased to levels below the physiological concentrations, leading to decreased PHGDH activity, which facilitates 3-PG accumulation. Such metabolic changes result in attenuated cell proliferation and tumor development.

Experiments herein indicate that upregulation of PGAM1 by increased gene expression in cancer cells provides a metabolic advantage to cancer cell proliferation and tumor growth; PGAM1 coordinates glycolysis and anabolic biosynthesis, at least in part by controlling intracellular levels of its substrate 3-PG and product 2-PG (FIG. 3). Although it is not intended that embodiments of the disclosure be limited by any particular mechanism, it is believed that 3-PG inhibits 6PGD by directly binding to the active site of 6PGD and competing with its substrate 6-PG. Attenuation of PGAM1 results in abnormal accumulation of 3-PG, which in turn inhibits 6PGD and consequently the oxidative PPP and anabolic biosynthesis. PGAM1 controls the intracellular levels of its product 3-PG not only directly through substrate consumption but also indirectly by controlling levels of its product 2-PG. Physiological concentrations of 2-PG promote the enzyme activity of PHGDH, which converts 3-PG to pPYR, reducing the cellular 3-PG levels. Upon attenuation of PGAM1, 2-PG is decreased to levels below the physiological concentrations, leading to decreased PHGDH activity, which facilitates 3-PG accumulation. This represents a regulatory mechanism by which 2-PG activates PHGDH to provide feedback control of 3-PG levels. Thus, PGAM1 activity is upregulated in cancer cells to promote glycolysis and keep the intracellular 3-PG levels low, which in turn permits high levels of the PPP and biosynthesis to fulfill the request of rapidly growing tumors. This is consistent with a report that expression of TP53 suppresses oxidative PPP in cancer cells (Jiang et al., Nature cell biology, 2011, 13, 310-316). In addition, PGAM1 may also be responsible for maintaining the physiological levels of 2-PG to sustain PHGDH activity, which diverts 3-PG from glycolysis to serine synthesis and contributes to maintaining relatively low levels of 3-PG in cancer cells.

Inhibition of PGAM1 by shRNA or treatment with a small molecule inhibitor PGMI-004A results in altered glycolysis and anabolic biosynthesis, and reduced cancer cell proliferation and tumor growth. Interestingly, targeting PGAM1 does not significantly affect intracellular ATP levels. Decreased ATP production due to attenuated glycolysis in PGAM1 knockdown cells may be compensated by alternative mechanisms other than mitochondrial oxidative phosphorylation, or perhaps the ATP consumption in PGAM1 knockdown cells is decreased accordingly. Methyl-2-PG treatment rescues most of the aforementioned phenotypes. Rescued 2-PG levels in cells with attenuated PGAM1 reversed decreased lactate production by rescuing the glycolytic process downstream of PGAM1, as well as reduced oxidative PPP flux and biosynthesis of RNA and lipids, at least in part by decreasing elevated 3-PG levels. However, methyl-2-PG treatment only partially rescues the attenuated cell proliferation in PGAM1 knockdown cells or cells treated with PGMI-004A. This result suggests that PGAM1 may contribute to cell proliferation in both 2-PG-dependent and independent manners.

The current understanding of the connection between glycolysis and PPP/biosynthesis is based upon a model in which glycolytic intermediates can be diverted into PPP and biosynthesis pathways as precursors. The concentrations of glycolytic metabolites such as 3-PG and 2-PG can directly affect the catalytic activity of enzymes involved in PPP and biosynthesis, which represents an additional link between glycolysis, PPP and biosynthesis. Metabolites have been suggested to function as signaling molecules. Examples include AMP, which is an allosteric activator for AMP-Activated Protein Kinase (AMPK), a kinase that senses intracellular energy levels (ATP/AMP ratio), and glutamine, which activates leucine uptake, leading to mTOR activation. The cellular levels of 3-PG and 2-PG, two intermediates in glycolysis, have additional regulatory impact on metabolic enzymes to affect cell metabolism and consequently proliferation, which provides an example to suggest that glycolytic metabolites could also serve as signaling molecules to control cell metabolism and cellular responses. Moreover, findings herein also indicate a feedback mechanism by which the product levels (2-PG) of a metabolic enzyme (PGAM1) can regulate its substrate levels (3-PG) by affecting an alternative enzyme (PHGDH) that is involved in production of this substrate.

Targeting PGAM1 by a PGAM1-derived inhibitory peptide or PGAM inhibitor MJE3 attenuates cancer cell proliferation. Studies herein suggest that protein expression and enzyme activity levels of PGAM1 are important for cancer cell proliferation and tumor growth. Certain PGM1 inhibitors herein exhibits promising efficacy in treatment of xenograft nude mice in vivo with minimal toxicity, as well as in diverse human cancer cells and primary leukemia cells from human patients in vitro with no obvious off target effect and minimal toxicity to human cells. Anti-PGAM1 is a promising therapy in clinical treatment of tumors that heavily rely on the Warburg effect.

Y26 Phosphorylation Enhances PGAM1 Enzyme Activity by Promoting H11 Phosphorylation.

Figure 13A:
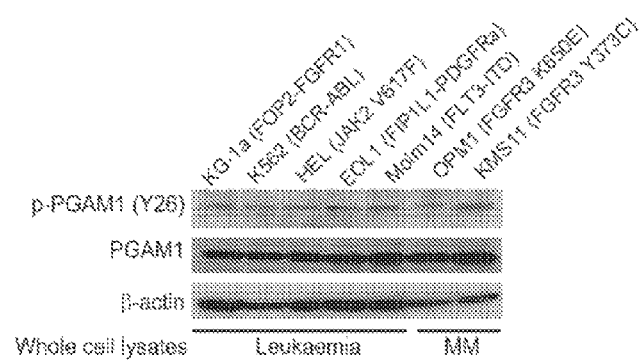
FIGS. 13A-G show data indicating Y26 phosphorylation of PGAM1 is common in leukemia cells, which contributes to control of 3-PG and 2-PG levels and is important for cancer cell metabolism, proliferation and tumor growth. (A) PGAM1 is commonly expressed and Y26-phosphorylated in leukemia and multiple myeloma cells. (B-C) Left: Active, recombinant FGFR1 (rFGFR1) and JAK2 (rJAK2) phosphorylates rPGAM1 at Y26 and such phosphorylation is abolished in Y26F mutant proteins (B and C, respectively). Right: Inhibition of FOP2-FGFR1 by TKI258 in leukemia KG1a cells and JAK2 V617F mutant by AG490 in leukemia HEL cells (B and C, respectively) results in decreased Y26 phosphorylation of PGAM1. (D) Generation of H1299 cells with stable knockdown of endogenous hPGAM1 and rescue expression of mPGAM1 WT or Y26F mutant. (E) Attenuation of PGAM1 by expressing catalytically less active mPGAM1 Y26F mutant results in increased intracellular 3-PG levels (left) and decreased 2-PG levels (right), while treatment with cell permeable methyl-2PG reverses these alterations in Y26F cells. (F) Y26F cells have a decreased cell proliferation rate compared to control cells expressing mPGAM1 WT, while treatment with methyl-2PG significantly rescues the reduced cell proliferation of Y26F cells. (G) Attenuation of PGAM1 by rescue expression of Y26F mutant results in decreased tumor growth potential of H1299 cells in xenograft nude mice. Left: Dissected tumors (indicated by red arrows) in a representative nude mouse; expression and Y26 phosphorylation levels of PGAM1 or mPGAM1 proteins in tumor lysates are shown. Right: Cells expressing mPGAM1 Y26F show significantly reduced tumor formation in xenograft nude mice compared to cells expressing mPGAM1 WT.
Figure 13B:
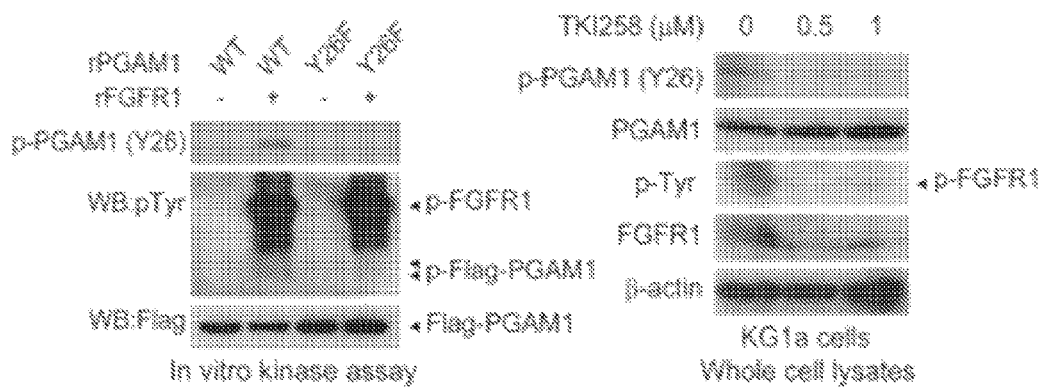
Figure 13C:
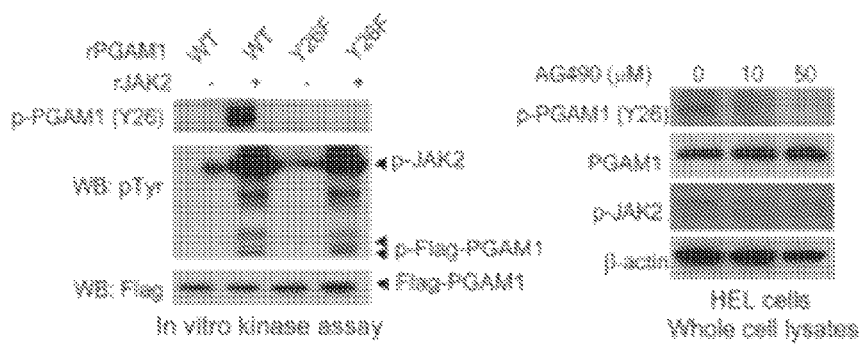
Figure 13D:
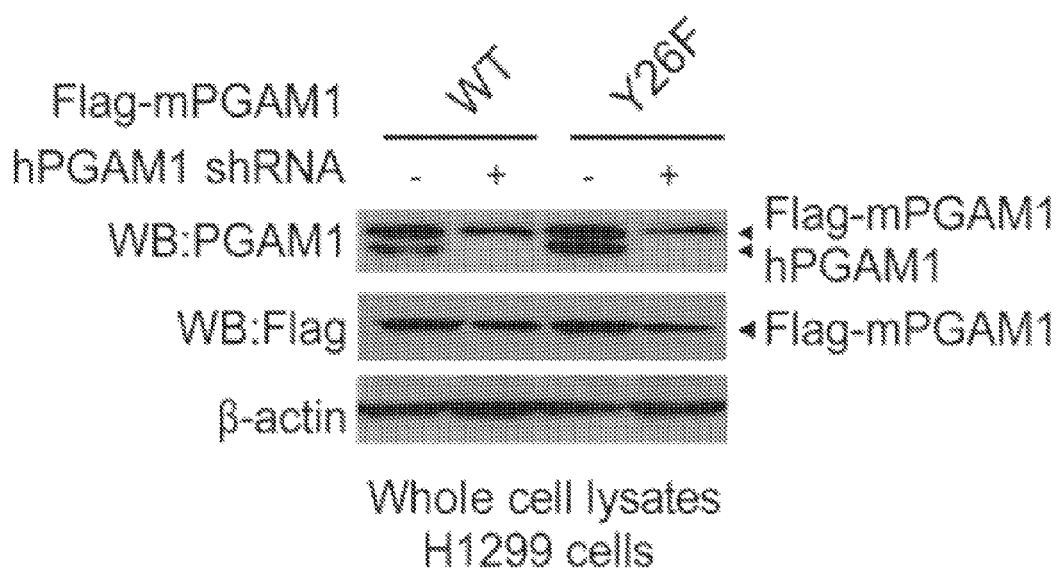
Figure 13E:
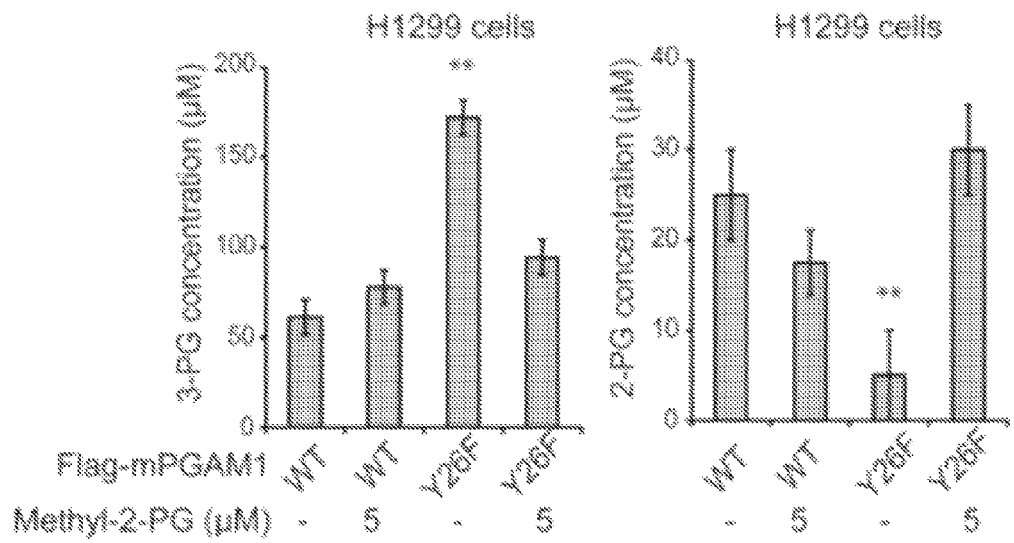
Figure 13F:
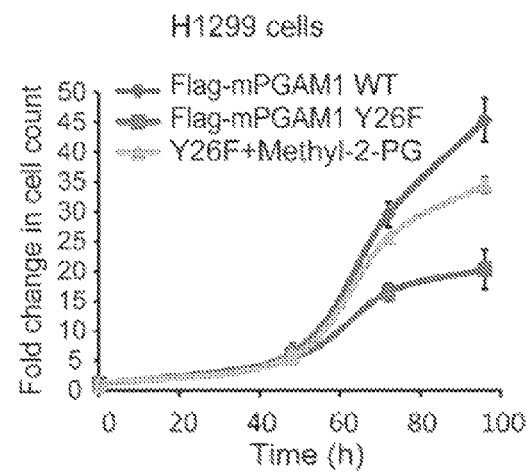
Figure 13G:
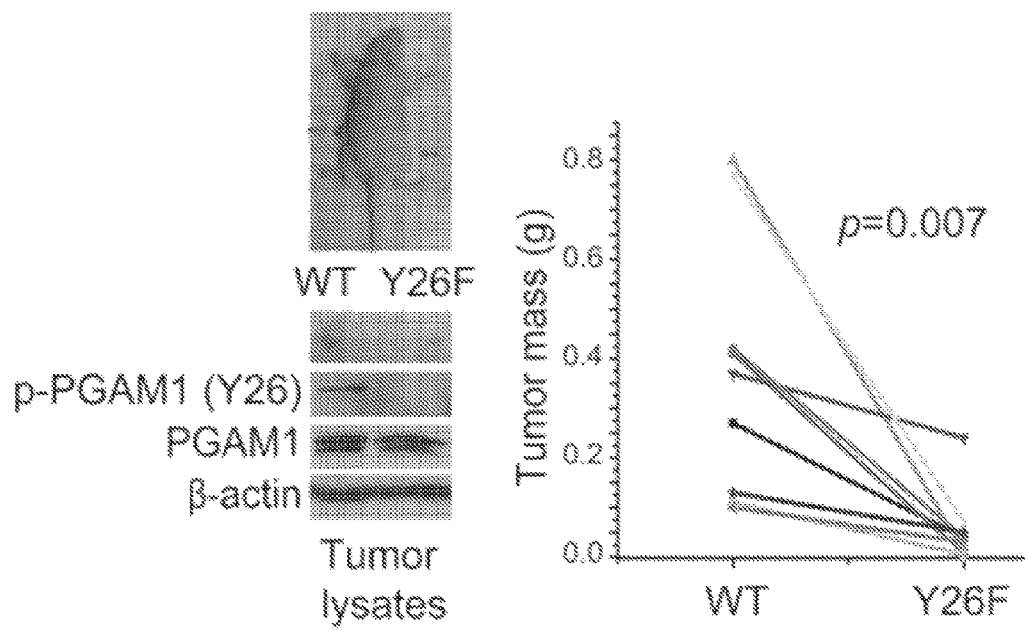

Phospho-proteomics studies identified PGAM1 as Y26 phosphorylated in cancer and leukemia cells (FIG. 13A). In vitro kinase assays where conducted where active, recombinant FGFR1 (rFGFR1) phosphorylated purified, Flag-tagged recombinant PGAM1 (rPGAM1) (FIG. 13B) at Y26 (FIG. 13B), which was accessed by a specific phospho-PGAM1 (pY26) antibody. Inhibition of FGFR1 by TKI258 treatment results in decreased PGAM1 activity in the presence but not absence of cofactor 2,3-bisphosphoglycerate (2,3-BPG)(FIG. 13C). PGAM1 is believed to be activated upon binding of 2,3-BPG, which may "phosphorylate" PGAM1 at histidine 11 (H11) by transferring the C3 phosphate. Our mutational analysis revealed that in the presence of 2,3-BPG, rFGFR1 significantly activates rPGAM1 WT and control Y133F mutant but not Y26F mutant (FIG. 13D). Structural studies revealed that Y26 is close to the cofactor 2,3-BPG binding site (FIG. 13E), suggesting a potential mechanism wherein Y26 phosphorylation by FGFR1 may induce conformational change to promote cofactor binding. To test this hypothesis, active rFGFR1 was incubated with purified, recombinant PGAM1 WT, Y26F or a control Y133F mutant in an in vitro kinase assay, followed by incubation with a competitive 2,3-BPG fluorescent analogue (8-hydroxy-1,3,6-pyrenetrisulfonate). The decrease in fluorescence (ex: 362 nm, em: 520 nm) compared with buffer control was measured as 2,3-BPG binding ability. Phosphorylation of PGAM1 WT or a control Y133F mutant by FGFR1 resulted in a significant increase in the amount of bound 2,3-BPG analogue, whereas substitution of PGAM1 Y26 abolished enhanced binding of cofactor in the presence of rFGFR1 (FIG. 13F). Moreover, a quantitative mass spectrometry based study (FIG. 13G) revealed that the H11 phosphorylation levels of Y26F mutant is significantly lower compared to PGAM1 WT in an in vitro kinase assay using PGAM1 proteins incubated with rFGFR1 in the presence of 2,3-BPG (FIG. 13G; left). Similar results were obtained (FIG. 13G; right) when using Flag-tagged mouse PGAM1 (mPGAM1) WT and Y26F from "rescue" H1299 cells with stable knockdown of endogenous human PGAM1 (hPGAM1) and rescue expression of Flag-mPGAM1 WT or Y26F mutant. These results suggest that Y26 phosphorylation enhances PGAM1 activity by promoting 2,3-BPG binding to PGAM1 and consequently H11 phosphorylation.

Methods of Use

The compounds and pharmaceutical compositions disclosed can be used to inhibit the PGAM pathway. Examples are listed for the use of an exemplary compound in treating head and neck cancer, lung cancer, and leukemia. Other cancers have also been shown to favor the PGAM pathway: lung cancer, Durany et al., Phosphoglycerate mutase, 2,3- bisphosphoglycerate phosphatase and enolase activity and isoenzymes in lung, colon and liver carcinomas, 75:7 British Journal of Cancer 969-977 (1997), breast cancer, Durany et al, Phosphoglycerate mutase, 2,3-bisphosphoglycerate phosphatase, creatine kinase and enolase activity and isoenzymes in breast carcinoma, 82:1 British Journal of Cancer 20-27 (2000), liver cancer, Durany et al., Phosphoglycerate mutase, 2,3-bisphosphoglycerate phosphatase and enolase activity and isoenzymes in lung, colon and liver carcinomas, 75:7 British Journal of Cancer 969-977 (1997), colon cancer, Durany et al., Phosphoglycerate mutase, 2,3-bisphosphoglycerate phosphatase and enolase activity and isoenzymes in lung, colon and liver carcinomas, 75:7 British Journal of Cancer 969-977 (1997) and colorectal cancer. Teruyuki Usuba, Purification and Identification of Monoubiquitin-phosphoglycerate Mutase B Complex from Human Colorectal Cancer Tissues, 94:5 International Journal of Cancer 662-668 (2001). See also, Glycolysis inhibition for anticancer treatment, 25:34 Oncogene 4633-4646 (2006). The compounds and pharmaceutical compositions disclosed herein may be prescribed to patients diagnosed with or suffering from any form of cancer as a treatment for their ailment.

It is further contemplated that these compounds and compositions may be used in the prevention of all forms of cancer. Pharmaceutical compositions disclosed can be prescribed to subjects at risk for cancer in order to lower the incidence rate of cancer. Since cancer survival rates are higher when the disease is caught in the early stages, a preventive treatment will increase the likelihood of survival for subjects not yet diagnosed with the disease.

Other diseases that involve regulation of the PGAM pathway and in which use of the compounds disclosed would be beneficial include muscular dystrophy (and other muscle disorders) and glycogen storage disease. See Clown et al., Plasma phosphoglycerate mutase as a marker of muscular dystrophy, 65:2 Journal of the Neurological Sciences 201-210 (1984). In certain embodiments, the disclosure contemplates methods of using compounds disclosed herein in the treatment or prevention of muscular dystrophy or other glycogen storage diseases by administration to a subject in need thereof.

Anthracene-9,10-Dione Derivatives

In certain embodiments, the anthracene-9,10-dione derivative is a compound of Formula I,

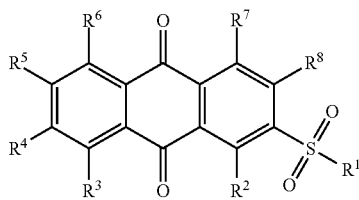

Formula I prodrug, ester, or salt thereof, wherein:

$R^1$, $R^2$, $R^3$, $R^4$, $R^5$, $R^6$, $R^7$ and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, $R^4$, $R^5$, $R^6$, $R^7$, and $R^8$ are optionally substituted with one or more, the same or different, $R^9$;

$R^9$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{11}$;

$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In some embodiments, the disclosure relates to compounds of Formula I or salts thereof, wherein $R^7$ is hydroxyl.

In some embodiments, the disclosure relates to compounds of Formula I or salts thereof, wherein $R^8$ is hydroxyl.

In some embodiments, the disclosure relates to compounds of Formula I or salts thereof, wherein $R^1$ is amino wherein $R^1$ is optionally substituted with one or more, the same or different, $R^9$.

In some embodiments, the disclosure relates to compounds of Formula I or salts thereof, wherein $R^1$ is amino and is substituted with an aryl ring, wherein the aryl ring is optionally substituted with one or more, the same or different $R^{10}$.

In some embodiments, the disclosure relates to compounds of Formula I or salts thereof, wherein $R^1$ is amino and is substituted with an aryl ring, wherein the aryl ring substituted in the para position with an alkyl, wherein the alkyl group is optionally substituted with one or more, the same or different $R^{11}$.

In some embodiments, the disclosure relates to compounds of Formula I or salts thereof, wherein $R^1$ is amino and is substituted with an aryl ring, wherein the aryl ring substituted in the para position with a methyl, wherein the methyl group is optionally substituted with one or more, the same or different $R^{11}$.

In some embodiments, the disclosure relates to compounds of Formula I or salts thereof, wherein $R^1$ is amino and is substituted with an aryl ring, wherein the aryl ring substituted in the para position with a methyl, wherein the methyl group is substituted with one or more, the same or different halogens.

In some embodiments the disclosure relates to compounds of Formula I or salts thereof, wherein $R^1$ is amino and is substituted with an aryl ring, wherein the aryl ring substituted in the para position with trifluoromethane.

In certain embodiments, the derivative is 3,4-dihydroxy-9,10-dioxo-9,10-dihydroanthracene-2-sulfonic acid or 3,4-dihydroxy-9,10-dioxo-N-(4-(trifluoromethyl)phenyl)-9,10-dihydroanthracene-2-sulfonamide prodrug, ester, or salt thereof optionally substituted with one or more, the same or different, substituent(s).

Pharmaceutical Compositions

The compounds of the present disclosure can be administered to a subject either alone or as a part of a pharmaceutical composition.

This application claims as a novel pharmaceutical composition, all the claimed compounds combined with one or more pharmaceutical agents, as well as the combination of one or more pharmaceutical agents with any compound in the family represented by Formula I. Pharmaceutically acceptable salts, solvates and hydrates of the compounds listed are also useful in the method of the disclosure and in pharmaceutical compositions of the disclosure.

The pharmaceutical compositions of the present disclosure can be administered to subjects either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Proper fluidity can be maintained, for example, by the use of a coating such as lecithin, by the maintenance of the required particle size in the case of dispersions and by the surfactants.

These compositions may also contain adjuvants such as preserving, emulsifying, and dispensing agents. Prevention of the action of microorganisms be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Compositions for rectal administrations are preferably suppositories which can be prepared by mixing the compounds of the present disclosure with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet (2006) 21(3):173-85, entitled "Human carboxylesterase isozymes: catalytic properties and rational drug design.

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit®RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit®

RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or can not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

Combination Therapies

The cancer treatments disclosed herein can be applied as a sole therapy or can involve, conventional surgery or radiotherapy or chemotherapy. Such chemotherapy can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-a mine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

Antibodies

In certain embodiments, the disclosure relates to an antibody that binds the PGAM1 phospho-Y26 epitope. In certain embodiments the antibody is a human chimera or a humanized antibody that binds PGAM1 phospho-Y26 epitope.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in U.S. Pat. No. 5,223,409.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. U.S. Pat. No. 7,064,244.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. No. 4,816,567 and U.S. Pat. No. 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. No. 7,125,689 and U.S. Pat. No. 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

EXAMPLES

Synthesis of PGMI-004A and methyl-2-PG

Synthesis of PGMI-004A involves two steps. The first step was to synthesize 3,4-dihydroxy-9,10-dioxo-2-anthracenesulfonyl chloride. In brief, 3,4-dihydroxy-9,10-dioxo-2-anthracene sulfonic acid sodium salt (1.71 g, 5.0 mmol) was added chlorosulfonic acid (50 mL) and the mixture was heated to 90-100° C. for 5 hours. After cooled to room temperature, the reaction solution was added to ice (200 g). After the ice was melted, the solution was extracted with dichloromethane (3×150 mL) and the organic phase was combined and dried over sodium sulfate. After removal of dichloromethane, the residue was subjected to silica chromatography to give product 3,4-dihydroxy-9,10-dioxo-2-anthracenesulfonyl chloride as a brown solid (0.59 g, 35%). $^1$H NMR (500.1 MHz) (Acetone-$d_6$) δ: 12.95 (s, 1H), 11.65 (br., 1H), 8.35 (m, 2H), 8.21 (s, 1H), 7.98 (m, 2H). $^{13}$C NMR (125.8 MHz) (DMSO-$d_6$) δ: 189.7, 181.8, 152.9, 150.0, 136.6, 136.4, 135.6, 134.9, 134.4, 128.2, 128.0, 124.4, 119.7, 117.6. MS calcd. for Cl4H7ClO6S [M-H]—, 337.0 (calcd.); 336.9 (found).

The second step was to synthesize N-(4-trifluoromethyl)-penyl-3,4-dihydroxy-9,10-dioxo-2-anthracenesulfonamide (PGMI-004A). 3,4-Dihydroxy-9,10-dioxo-2-anthracenesulfonyl chloride (0.50 g, 1.47 mmol) in dichloromethane (20 mL) was added triethylamine (4.0 equiv.) and 4-(trifluoromethyl)aniline (2.0 equiv.) and the mixture was stirred at room temperature overnight. After filtration, the solvent was evaporated and the resulting solid was subjected to silica chromatography to give product N-(4-trifluoromethyl)-penyl-3,4-dihydroxy-9,10-dioxo-2-anthracenesulfonamide as a red solid (0.29 g, 42%). $^1$H NMR (500.1 MHz) (DMSO-$d_6$) δ: 8.12 (m, 3H), 7.83 (m, 2H), 7.58 (m, 2H), 7.28 (m, 2H). $^{13}$C NMR (125.8 MHz) (DMSO-$d_6$) δ: 189.8, 180.6, 154.3, 143.2, 136.5, 135.4, 135.2, 134.3, 129.0, 128.1, 127.9, 127.8, 127.7, 127.6, 126.8, 124.8, 124.6, 124.2, 123.1, 119.8, 118.5, 114.4. MS calcd. for C21H12F3O6S [M-H]—, 462.0 (calcd.); 462.0 (found).

To synthesize methyl ester of D(+)-2-phosphoglyceric acid, D(+)2-Phosphoglyceric acid sodium salt (20 mg) was added hydrogen chloride in methanol (5 mL) and the mixture was stirred at room temperature for 5 h. Removal of the solvent under reduced pressure gave product methyl ester of D(+)-2-phosphoglyceric acid quantitatively as a white solid. $^1$H NMR (500.1 MHz) (CD$_3$OD) δ: 4.72 (m, 1H), 3.87 (m, 2H), 3.77 (s, 3H). 1H NMR (125.8 MHz) (CD$_3$OD) δ: 170.8, 76.7 (J=5.41 Hz), 63.6 (J=5.79 Hz), 52.4. $^{31}$P NMR (202.4 MHz) (CD$_3$OD) δ: -0.946.

In Vitro PGAM1 and Enolase Assays.

An in vitro PGAM1 assay was performed as primary screening. PGAM1 enzyme mix was prepared containing 100 mM Tris-HCl, 100 mM KCl, 5 mM MgCl$_2$, 1 mM ADP, 0.2 mM NADH, 5 mg/ml recombinant PGAM1, 0.5 units/ml enolase, 0.5 units/ml recombinant pyruvate kinase M1, and 0.1 units/ml recombinant LDH. 3-PG was added last at the final concentration of 2 mM to initiate the reaction. The decrease in autofluorescence (ex:340 nm, em:460 nm) from oxidation of NADH was measured as PGAM1 activity. An in vitro enolase assay as secondary screening was also performed. Enolase enzyme mix was prepared containing 100 mM Tris-HCl, 100 mM KCl, 5 mM MgCl$_2$, 1 mM ADP, 0.2 mM NADH, 0.5 units/ml enolase, 0.5 units/ml recombinant pyruvate kinase M1, and 0.1 units/ml recombinant LDH. 2-PG was added last at the final concentration of 2 mM to initiate the reaction. The decrease in autofluorescence (ex:340 nm, em:460 nm) from oxidation of NADH was measured as enolase activity. For K$_d$ determination, 2 µM of human PGAM1 proteins were mixed with different concentrations of PGMI-004A (1-500 µM). The fluorescence intensity (Ex: 280 nm, em: 350 nm) from Tryptophan were measured. Assay was carried out in Tris-HCl buffer (10 mM Tris, pH 7.4, 100 mM NaCl) containing 5% DMSO.

PGMI-004A-3-PG Competitive Binding Assay.

2 µM rPGAM1 was incubated with different concentrations of PGMI-004A (0-40 µM) and 3-PG(0-400 µM), and Tryptophan fluorescence (ex: 280 nm, em:350 nm) from rPGAM1 was measured in 100 mM Tris-HCl buffer. Fluorescence intensity without any treatment is presented as 1.0.

Thermal Melt Shift Assay.

In brief, thermal shift assay of compound-protein interaction was performed in 384-well PCR plates with various compound concentrations and 200 µg/ml protein in a buffer solution (20 mM Tris-HCl, 100 mM NaCl, pH 7.4). SYPRO orange was used as a dye to monitor the fluorescence change at 610 nm. Small molecules were dissolved in DMSO and added to protein solution. Final DMSO concentration of solution is 1%. Dissociation constants (Kds) for protein-ligand interaction were calculated using the method as described.

The fluorescence intensity data were fitted to Eq. (1) to obtain ΔHu, ΔCpu, and T$_m$ by nonlinear regression using the program Prism:

$$F(T) = F(post) + \frac{F(pre) - F(post)}{1 + \exp\left\{-\frac{\Delta Hu}{R}\left(\frac{1}{T} - \frac{1}{T_m}\right) + \frac{\Delta Cpu}{R}\left[\ln\left(\frac{T}{T_m}\right) + \frac{T_m}{T} - 1\right]\right\}} \quad (1)$$

where

F(T): fluorescence intensity at temperature T;

T$_m$: midpoint temperature of the protein-unfolding transition;

F(pre) and F(post): pretransitional and posttransitional fluorescence intensities;

R: gas constant,

ΔHu: enthalpy of protein unfolding;

ΔCpu: heat capacity change on protein unfolding.

The thermal unfolding parameters for 6PGD and PGAM1 alone were determined from 4 control wells, each containing 0.2 mg/mL protein. The average Tm, ΔHu, ΔCpu are 326.00 K (52.85° C.), 103.9 kcal/mol, and 4.5 kcal/mol for 6PGD, 322.43 K (49.28° C.), 157.0 kcal/mol, and 10.3 kcal/mol for PGAM1, respectively. To calculate the ligand-binding affinity at T$_m$ and T, equation (2) and (3) were used:

$$F(T) = F(post) + \frac{F(pre) - F(post)}{1 + \exp\left\{-\frac{\Delta Hu}{R}\left(\frac{1}{T} - \frac{1}{T_m}\right) + \frac{\Delta Cpu}{R}\left[\ln\left(\frac{T}{T_m}\right) + \frac{T_m}{T} - 1\right]\right\}} \quad (2)$$

$$F(T) = F(post) + \frac{F(pre) - F(post)}{1 + \exp\left\{-\frac{\Delta Hu}{R}\left(\frac{1}{T} - \frac{1}{T_m}\right) + \frac{\Delta Cpu}{R}\left[\ln\left(\frac{T}{T_m}\right) + \frac{T_m}{T} - 1\right]\right\}} \quad (3)$$

Where $K_{L(Tm)}$: ligand association constant at T$_m$;

$[L_{Tm}]$: free ligand concentration at T$_m$;

$K_{L(T)}$: ligand association constant at T (37° C. was used for all the calculation);

$\Delta H_{L(T)}$: van't Hoff enthalpy of binding at temperature T. Here we use −5 kcal/mol which makes the calculated binding constants closer to the real values.

Thermal shift data for 6PGD at 2 mM 3PG and 0.2 mM 6-PG concentrations were used to calculate the K$_d$ since both of the shift Tm are around 2-2.5° C. and comparable. The K$_d$ for 3PG and 6-PG with 6PGD are 460±40 µM and 37±3 µM. Thermal shift data for PGAM1 at 40 µM PGMI-004A was used to calculate the K$_d$, which is 9.4±2.0 µM.

Cell Proliferation and Viability Assays.

For leukemia cell proliferation assay, 10×10$^4$ cells were seeded in non-tissue culture coated 6-well plate and incubated at 37° C. for indicated times. Cell numbers were counted by trypan blue exclusion under a microscope (×40) at indicated times and the percentage of cell proliferation was determined by comparing PGAM1 knockdown cells to pLKO.1 vector expressing cells. For cell viability assays of leukemia cells, 10×10$^4$ cells were seeded in non-culture coated 6-well plate and incubated with PGMI-004A at 37° C. for indicated times. Cell viability was determined by counting drug-treated cells compared to DMSO-treated control cells with trypan blue exclusion under a microscope (×40) and by using CellTiter96Aqueous One solution proliferation kit (Promega). For adherent cell proliferation assay such as H1299 and MDA-MB231 cells, 5×10$^4$ cells were seeded in E-well plate 24 h before the assay starts and were cultured at 37° C. 24 h after seeding, cells were treated with 5 µM Methyl-2PG and incubated at 37° C. for indicated times. Cell proliferation was determined by the increase in cell number indicated times after the treatment starts compared to that at the treatment starts for each cell line (T=0). Cell numbers were counted by trypan blue exclusion under a microscope (×40). For adherent cell viability assay with trypan blue exclusion, 5×10$^4$ cells were seeded in 6-well plate 24 h before the assay starts and were cultured at 37° C. 24 h after seeding, cells were treated with PGMI-004A and incubated at 37° C. for indicated times. Cell viability was determined by counting drug-treated cells compared to DMSO-treated control cells with trypan blue exclusion under a microscope (×40). For MTT cell viability assay of adherent cells, 5×10$^3$ cells were seeded in 96-well plate 24 h before the assay starts and were cultured at 37° C. 24 h after seeding, cells were treated with PGMI-004A and incubated at 37° C. for 3 days. Cell viability was determined by using CellTiter96Aqueous One solution proliferation kit (Promega).

Xenograft Studies.

Nude mice (Athymic Nude-Foxn1$^{nu}$, female 6-8-week-old, Harlan) were subcutaneously injected with 10×10$^6$ H1299 cells harboring empty vector on the left flank, and cells with stable knockdown of endogenous hPGAM1 on the right flank, respectively. The tumors were harvested and weighed at the experimental endpoint, and the masses of tumors (g) derived from cells with and without stable knockdown of endogenous hPGAM1 in both flanks of each mouse were compared. Statistical analyses were performed by comparison in relation to the control group with a two-tailed paired Student's t test. For drug evaluation of PGMI-004A using xenograft mice, the drug was administered by daily i.p. injection at a dose of 100 mg/kg from 6 days after subcutaneous injection of H1299 cells on right flank of each mouse. Tumor growth was recorded by measurement of two perpendicular diameters of the tumors over a 3-week course using the formula $4\pi/3\times(\text{width}/2)^2\times(\text{length}/2)$. The tumors were harvested and weighed at the experimental endpoint. The masses of tumors (g) treated with vehicle control (DMSO:PEG400:PBS at a ratio of 4:3:3) and PGMI-004A were compared and the p values were determined by a two-tailed Student's t test.

Primary Tissue Samples from Human Patients with Leukemia and Healthy Donors.

Approval of use of human specimens was given by the Institutional Review Board of Emory University School of Medicine. All clinical samples were obtained with informed consent with approval by the Emory University Institutional Review Board. Clinical information for the patients was obtained from the pathological files at Emory University Hospital under the guidelines and with approval from the Institutional Review Board of Emory University School of Medicine and according to the Health Insurance Portability and Accountability Act. Only samples from patients that were not previously treated with chemotherapy or radiation therapy were used. Mononuclear cells (MNCs) were isolated from peripheral blood and bone marrow samples from human leukemia patients or peripheral blood samples from healthy donors using lymphocyte separation medium (Cellgro). Cells were cultured in RPMI 1640 medium supplemented with 10% FBS and penicillin/streptomycin and incubated with increasing concentrations of PGMI-004A for up to 72 or 120 hours.

Antibodies

Phospho-Tyr antibody pY99 and FGFR1 antibody were from Santa Cruz Biotechnology, Santa Cruz, Calif.; PGAM1 antibody was from Novus; antibodies against GST and β-actin were from Sigma, St. Louis, Mo. Specific antibody against phospho-PGAM1 (p-Y26) was generated. Specific antibody against phospho-PGAM1 (p-Y26) was generated by CST.

RNAi

ShRNA construct for PGAM1 knockdown was purchased from Open Biosystems, Huntsville, Ala. The sequence of shRNA used for knockdown is as follows:

(SEQ ID NO: 1)
5'-CCGGCAAGAACTTGAAGCCTATCAACTCGAGTTGATAGGCTTCAAGTT

CTTGTTTTTG-3'.

PGAM1 Enzyme Assay.

Murine PGAM1 was Flag-tagged by PCR and subcloned into pMSCV-neo derived Gateway destination vector as described previously (Chen et al., Blood, 2005, 106, 328-337). For GST-tagged PGAM1 expression in mammalian cells, PGAM1 variants were subcloned into pDEST27 vector (Invitrogen, Carlsbad, Calif.). For His-tagged PGAM1 expression in bacterial cells, PGAM1 was subcloned into pET53 vector (Novagen).

$(\text{His})_6$-tagged PGAM1 proteins were purified by sonication of high expressing BL21(DE3)pLysS cells obtained from a 250 mL culture subjected to IPTG-induction for 4 h. Cell lysates were resolved by centrifugation and loaded onto a Ni-NTA column in 20 mM imidazole. After a step of 2x washing, the protein was eluted with 250 mM imidazole. Proteins were desalted on a PD-10 column and the purification efficiency was examined by Coomassie staining and western blotting.

PGAM1 activity was measured by multiple enzymes coupled assay. PGAM1 enzyme mix containing 100 mM Tris-HCl, 100 mM KCl, 5 mM $MgCl_2$, 1 mM ADP, 0.2 mM NADH, 5 mg/ml recombinant PGAM1, 0.5 units/ml enolase, 0.5 units/ml recombinant pyruvate kinase M1, and 0.1 units/ml recombinant LDH was prepared. 3-PG was added last at a final concentration of 2 mM to initiate the reaction. The decrease in autofluorescence (ex:340 nm, em:460 nm) from oxidation of NADH was measured as PGAM1 activity.

Cellular Metabolites Extraction and Measurement.

Cellular metabolites were extracted and spectrophotometrically measured as described previously with some modifications. To determine cellular concentration of 2-PG and 3-PG, 100 μL of packed cell pellets were homogenized in 1.5 ml of hypotonic lysis buffer (20 mM HEPES (pH 7.0), 5 mM KCl, 1 mM $MgCl_2$, 5 mM DTT, and protease inhibitor cocktail). The homogenates were centrifuged in a cold room at 4° C. for 10 minutes at maximum speed, and the supernatants were applied to Amicon Ultra tubes with 1 OKDa cut off filter (Millipore). The flow through containing the metabolites was used for the measurement. NADH, ADP, and $MgCl_2$ were added to the flow through to final concentrations of 0.14 mM, 1 mM, and 50 mM, respectively. Recombinant LDH and PKM1 proteins were added to final concentrations of 5 μg/ml and 10 μg/ml, respectively. Recombinant enolase protein was added to a final concentration of 50 μg/ml to measure cellular 2-PG. Once the reaction was initiated by enolase, a decrease in absorbance at 340 nm from NADH oxidation was measured by a DU800 spectrophotometer (Beckman). After termination of the enolase reaction, recombinant PGAM1 protein was added to a final concentration of 25 μg/ml and the decrease in absorbance at 340 nm was immediately monitored to measure cellular 3-PG. 100 μL of 2-PG and 3-PG (Sigma) diluted with 1.5 ml of hypotonic lysis buffer were used as the standards.

Alternatively, perchloric acid was used to quench metabolism and the acid extracts from H1299 cell lysates were then neutralized with KOH (DeBerardinis et al., 2007), followed by enzymatic reactions using the final supernatant to determine the 3-PG and 2-PG levels. An isotope-ratio based detection method was used to determine intracellular 3-PG and 2-PG levels in cells. In brief, pure standards were derivatized with a trimethylsilyl donor (Tri-Sil, Pierce) and used to determine the retention times of 2-PG and 3-PG on GC/MS. These standards were also used to identify parent ions containing all three 2-PG and 3-PG carbons on the derivatized molecule (m/z 459 for both 2-PG and 3-PG), and to generate algorithms for natural isotope abundance correction. Next, two dishes of H1299 cells were cultured in RPMI supplemented with [U-$^{13}$C]glucose so that approximately 25% of the total glucose pool was labeled. After 6 hours of culture, the cells were quickly rinsed in ice-cold normal saline, lysed in 1 mL of cold 50% methanol, and frozen in liquid nitrogen. The lysates were freeze-thawed three times, then centrifuged to remove debris. The supernatant from the first sample was evaporated to dryness, derivatized in Tri-Sil, then injected (5 μL) onto an Agilent 6890 GC networked to an Agilent 5973 Mass Selective Detector. This confirmed that the fractional enrichments of glucose, lactate, 2-PG and 3-PG were 25-30%, with only the unenriched and fully enriched species present. The second sample was spiked with 25 nmoles of unlabeled 2-PG and 3-PG, derivatized, and analyzed by GC/MS. The 2-PG and 3-PG enrichments in this sample were 5.8% and 6.3%, respectively (Response FIG. 1B; left). Using the factor of isotopic dilution resulting from addition of 25 nmoles of unlabeled standards (4.8 for 2-PG and 4.1 for 3-PG), the cellular lysate contained approximately 6.6 nmoles of 2-PG and 8.1 nmoles of 3-PG. Assuming a 100 µL volume for the cell pellet, these figures correlate to intracellular concentrations of 66 µM for 2-PG and 81 µM for 3-PG, very close to the values measured by the enzymatic assay.

To determine cellular concentration of 6-PG, 200 µL of packed cell pellets were homogenized in 0.6 ml of hypotonic lysis buffer. The homogenates were centrifuged in a cold room at 4° C. for 10 minutes at maximum speed, and the supernatants were applied to Amicon Ultra tubes with 1 OKDa cut off filter (Millipore). The flow through containing the metabolites was used for the measurement. Tris-HCl (pH8.1) and $MgCl_2$ were added to the flow through to final concentrations of 50 mM and 1 mM, respectively. Recombinant 6PGD protein was added to a final concentration of 10 µg/ml, and the reaction was initiated by adding NADP (final concentration of 0.1 mM) to the reaction mixture. An increase in absorbance at 340 nm from NADPH production was measured by a DU800 spectrophotometer (Beckman). 200 µL of 6-PG (Sigma) diluted with 0.6 ml of hypotonic lysis buffer were used as the standards.

$^{14}$C-Lipid Synthesis and $^{14}$C-RNA Synthesis Assays.

$^{14}$C-lipids synthesized from $^{14}$C-glucose were measured. Subconfluent cells seeded on a 6-well plate were pre-incubated with PGMI-004A for 2 h prior to the addition of $^{14}$C-glucose. Cells were then incubated in complete medium spiked with 4 µCi/ml of D-[6-$^{14}$C]-glucose for 2 h in the presence of PGMI-004A, washed twice with PBS, and lipids were extracted by the addition of 500 µL hexane:isopropanol (3:2 v/v). Wells were washed with an additional 500 µL of hexane:isopropanol solution, and extracts were combined and air dried with heat. Extracted lipids were resuspended in 50 µL of chloroform, and subjected to scintillation counting. Scintillation counts were normalized with cell numbers counted by a microscope (×40). $^{14}$C-RNA synthesized from $^{14}$C-glucose was measured. Subconfluent cells seeded on a 6-well plate were pre-incubated with PGMI-004A for 2 h prior to the addition of $^{14}$C-glucose. Cells were then incubated in complete medium spiked with 4 µCi/ml of D-[U-$^{14}$C]-glucose for 2 h in the presence of PGMI-004A. RNA was then extracted using RNeasy columns (Qiagen) and $^{14}$C-RNA was assayed by scintillation counter. $^{14}$C counts for each sample were normalized by the amount of RNA.

$^{14}$C-Serine Synthesis Assay.

Serine synthesis flux from $^{14}$C glucose was measured as described previously (Parry, 1957) with modification. Subconfluent cells seeded on a 6 cm dish were incubated in complete medium spiked with 40 µCi/ml of D-[U-$^{14}$C]-glucose overnight. The incubated cells were lysed with hypotonic lysis buffer (20 mM HEPES (pH 7.0), 5 mM KCl, 1 mM $MgCl_2$, 5 mM DTT, and protease inhibitor cocktail), and the cell lysates were spun down by centrifugation to remove cell debris. The supernatant containing 100 µg of total protein was spotted onto Whatman 3MM paper. One-dimensional chromatogram was run in water saturated phenol, and two-dimensional chromatogram was run in 1-butanol:acetic acid:water solution at the ratio of 100:22:50. L-serine (Sigma) was used as a standard. L-serine dissolved in hypotonic lysis buffer was spotted onto another paper, which was run under the same conditions in parallel with the cell lysate sample. Spots of amino acids were developed by ninhydrin reaction. The spot corresponding to serine was identified based on $R^f$ values of L-serine standard, cut out from the paper, and directly subjected to scintillation counting.

Glycolytic Rate Assay.

Glycolytic rate was measured by monitoring the conversion of 5-$^3$H-glucose to $^3H_2O$. $10^6$ cells were washed once in PBS prior to incubation in 1 ml of Krebs buffer without glucose for 30 min at 37° C. The Krebs buffer was then replaced with Krebs buffer containing 10 mM glucose spiked with 10 µCi of 5-$^3$H-glucose. Following incubation for 1 h at 37° C., triplicate 50 µl aliquots were transferred to uncapped PCR tubes containing 50 µl of 0.2 N HCl, and a tube was transferred into an eppendorf tube containing 0.5 ml of $H_2O$ for diffusion. The tubes were sealed, and diffusion was allowed to proceed for a minimum of 24 h at 34° C. The amounts of diffused $^3H_2O$ were determined by scintillation counting.

Lactate Production, Oxygen Consumption and Intracellular ATP Assays.

Cellular lactate production was measured under normoxia with a fluorescence-based lactate assay kit (MBL). Phenol red-free RPMI medium without FBS was added to a 6 well-plate of subconfluent cells, and was incubated for 1 h at 37° C. After incubation, 1 ml of media from each well was assessed using the lactate assay kit. Cell numbers were counted by a microscope (×40). Oxygen consumption rates were measured with a Clark type electrode equipped with 782 oxygen meter (Strathkelvin Instruments). $1 \times 10^7$ cells were resuspended in RPMI 1640 medium with 10% FBS and placed into a water-jacked chamber RC300 (Strathkelvin Instruments) and recording was started immediately. Intracellular ATP concentration was measured by an ATP bioluminescent somatic cell assay kit (Sigma). $1 \times 10^6$ cells were trypsinized and resuspended in ultrapure water. Luminescence was measured with spectrofluorometer (SPECTRA Max Gemini; Molecular Probe) immediately after the addition of ATP enzyme mix to cell suspension.

NADPH/NADP$^+$ Ratio Assay.

NADPH/NADP$^+$ kit (BioAssay Systems) was used to measure cellular NADPH/NADP$^+$ ratio. Subconfluent cells seeded on a 10 cm dish were collected by a scraper, washed with PBS, and lysed with 200 µL of NADP$^+$ (or NADPH) extraction buffer. Heat extract was allowed to proceed for 5 minutes at 60 degrees before adding 20 µL of assay buffer and 200 µL of the counter NADPH (or NADP$^+$) extraction buffer to neutralize the extracts. The extracts were spun down and the supernatants were reacted with working buffer according to the manufacturer's protocol. The absorbance at 565 nm from the reaction mixture was measured with plate reader.

Oxidative PPP Flux Assay Using $^{14}CO_2$ Release.

Cells were seeded on 6-cm dishes that are placed in a 10-cm dish with 2 sealed pinholes on the top. $^{14}CO_2$ released from cells was collected by completely sealing the 10-cm dish, in which the cells on the 6-cm dish were incubated in 2 ml of medium containing [1-$^{14}$C]- or [6-$^{14}$C]-glucose, respectively, at a final specific activity of 10 µCi/ml glucose at 37° C. for 3 h. The oxidative PPP flux was stopped by injecting 0.3 ml of 50% TCA through one of the holes on the top, and at the same time $^{14}CO_2$ released was trapped by injecting 0.3 ml of Hyamine Hydroxide into a small cup placed on the 10-cm dish through the second hole. Krebs cycle measurements, obtained in parallel samples incubated with [6-$^{14}$C]-glucose, were used to correct the oxidative PPP flux measurements obtained from samples incubated with [1-$^{14}$C]-glucose. Each dish was completely re-sealed with parafilm and incubated overnight at room temperature.

Hyamine Hydroxide in the small cup was dissolved into 60% methanol and directly subjected to scintillation counting.

G6PD and 6PGD Assays.

G6PD activity was determined by the NADPH production rate from G6PD and 6PGD, then subtracting that of 6PGD, since a product of G6PD, 6-phosphogluconolactone, is rapidly hydrolyzed to a substrate of 6PGD, 6-phosphogluconate, in cells. To obtain the combined dehydrogenase activity, substrates for both dehydrogenase enzymes were added to a cuvette. In another cuvette, substrates for the second enzyme, 6PGD, were added to obtain the activity of this enzyme. Substrate concentrations were as follows: 0.2 mM glucose 6-phosphate, 0.2 mM 6-phosphogluconate, and 0.1 mM NADP$^+$. 10 µg of cell lysates or 1 µg of recombinant protein were added to a cuvette containing buffer (50 mM Tris, 1 mM $MgCl_2$, pH 8.1) and then the reaction was initiated by NADP$^+$. The increase of absorbance at 341 nm was measured by a DU800 spectrophotometer (Beckman).

PHGDH Enzyme Assay.

PHGDH activity was spectrophotometrically measured as described previously. PHGDH enzyme buffer containing 200 mM Tris-HCl (pH8.1), 400 mM KCl, 0.6 mM NAD, 2 mM GSH, 10 mM EDTA was mixed with cell lysates or recombinant PHGDH protein. The reaction was initiated by the addition of 3-PG to a final concentration of 10 mM and followed by measuring the increase in absorbance at 340 nm over a 10 min period.

Primary Tissue Samples from Human Patients with Leukemia and Healthy Donors

Only samples from patients that were not previously treated with chemotherapy or radiation therapy were used. Mononuclear cells (MNCs) were isolated from peripheral blood and bone marrow samples from human leukemia patients or peripheral blood samples from healthy donors using lymphocyte separation medium (Cellgro). Cells were cultured in RPMI 1640 medium supplemented with 10% FBS and penicillin/streptomycin and incubated with increasing concentrations of PGMI-004A for up to 72 or 120 hours.

Xenograft Studies

An in vitro PGAM1 assay was used as primary screening followed by the secondary screening using an in vitro enolase assay to exclude screened compounds with potential off target effect. In xenograft studies, nude mice were subcutaneously injected with $10 \times 10^6$ H1299 cells stably expressing mPGAM1 WT and Y26F with stable knockdown of endogenous hPGAM1 on the left and right flanks, respectively or $10 \times 10^6$ H1299 cells with and without stable knockdown of endogenous hPGAM1 on the left and right flanks, respectively. The tumors were harvested and weighed at the experimental endpoint. Statistical analyses were done by comparison in relation to the control group with a two-tailed paired Student's t test. For drug evaluation of PGMI-004A using xenograft mice, the drug was administered by daily i.p. injection at a dose of 100 mg/kg from 6 days after subcutaneous injection of H1299 cells on right flank of each mouse. Tumor growth was recorded by measurement of two perpendicular diameters of the tumors over a 3-week course using the formula $4\pi/3 \times (width/2)^2 \times (length/2)$.

Nude mice (Athymic Nude-Foxn1nu, female 6-8-week-old, Harlan) were subcutaneously injected with $10 \times 10^6$ H1299 cells harboring empty vector or rescue cells stably expressing mPGAM1 WT on the left flank, and cells with stable knockdown of endogenous hPGAM1 or rescue cells stably expressing mPGAM1 Y26F on the right flank, respectively. The tumors were harvested and weighed at the experimental endpoint, and the masses of tumors (g) derived from cells expressing mPGAM WT or Y26F mutant in both flanks of each mouse, or those of tumors derived from cells with and without stable knockdown of endogenous hPGAM1 in both flanks of each mouse, were compared. Statistical analyses were performed by comparison in relation to the control group with a two-tailed paired Student's t test. For drug evaluation of PGMI-004A using xenograft mice, the drug was administered by daily i.p. injection at a dose of 100 mg/kg from 6 days after subcutaneous injection of H1299 cells on right flank of each mouse. Tumor growth was recorded by measurement of two perpendicular diameters of the tumors over a 3-week course using the formula $4\pi/3 \times (width/2)2 \times (length/2)$. The tumors were harvested and weighed at the experimental endpoint, and the masses of tumors (g) treated with vehicle control (DMSO:PEG400:PBS at a ratio of 4:3:3) and PGMI-004A were compared by a two-tailed unpaired Student's t test.

PGAM1 is Important for Cancer Cell Proliferation.

The effects of targeted down-regulation of diverse glycolytic enzymes were examined by shRNA in cancer cells. A group of glycolytic enzymes were found that are important to cancer cell metabolism and proliferation, including pyruvate kinase M2 (PKM2; 5) and PGAM1. In many cancers, including hepatocellular carcinoma and colorectal cancer, PGAM1 activity is increased compared with normal tissues. PGAM1 gene expression is believed to be up-regulated due to loss of TP53 in cancer cells, as TP53 negatively regulates PGAM1 gene expression. As shown in FIG. 1, stable knockdown of PGAM1 in lung cancer H1299, head and neck cancer 212LN, breast cancer MDA-MB231 and leukemia KG1a, K562 and Molm14 cells results in decreased cell proliferation with reduced PGAM1 activity and lactate production. These results suggest a role of PGAM1 protein levels in cancer cell proliferation and maintenance of glycolysis.

Y26 Phosphorylation Activates PGAM1 by Promoting H11 Phosphorylation.

Phospho-proteomics studies identified PGAM1 as phosphorylated at multiple tyrosine sites including Y26, Y92, Y119 and Y133 in murine haematopoietic Ba/F3 cells expressing constitutively active ZNF198-FGFR1 fusion tyrosine kinase 5. This was confirmed in an in vitro kinase assay where active, recombinant FGFR1 (rFGFR1) directly phosphorylated purified, Flag-tagged recombinant PGAM1 (rPGAM1) at tyrosine residues. In addition, GST-tagged PGAM1 was tyrosine phosphorylated in COS7 cells transiently co-transfected with plasmids encoding FGFR1 wild type (WT), but not in cells co-expressing GST-PGAM1 and a kinase dead (KD) form of FGFR1.

PGAM1 is believed to be activated upon binding of cofactor 2,3-bisphosphoglycerate (2,3-BPG), which was suggested to "phosphorylate" PGAM1 at histidine 11 (H11) by transferring the C3 phosphate to H11. In a PGAM1 enzyme activity assay, incubation with cofactor, 2,3-BPG significantly activates PGAM1 in cell lysates from FGFR1-expressing lung cancer H1299 and leukemia KG1a cells, and treatment with the FGFR1 small molecule inhibitor TKI258 significantly decreases PGAM1 enzyme activity, only in the presence but not absence of 2,3-BPG. In consonance with this observation, in a PGAM1 enzyme assay coupled with the FGFR1 in vitro kinase assay, rFGFR1 significantly activated rPGAM1 enzyme activity only in the presence but not absence of 2,3-BPG. Mutational analysis provided that, in the absence of 2,3-BPG, tyrosine phosphorylation by FGFR1 did not alter enzyme activity of rPGAM1 WT, Y26F, Y119F or Y133F.

Interestingly, Y92F mutant lost PGAM1 enzyme activity in the presence and absence of rFGFR1, suggesting that Y92 is intrinsically required for PGAM1 enzyme activity. In contrast, in the presence of 2,3-BPG, rFGFR1 significantly activates rPGAM1 Y119F and Y133F, in addition to rPGAM1 WT as previously observed. However, substitution of Y26 abolished the FGFR1-dependent increase in the PGAM1 enzyme activity. Y92F mutant again showed a very low level of PGAM1 activity, however, incubation with rFGFR1 resulted in significantly increased PGAM1 enzyme activity of Y92F in the presence of 2,3-BPG. These data together suggest that Y26 phosphorylation is responsible for mediating FGFR1-dependent activation of PGAM1 in the presence of 2,3-BPG.

Figures 2A, 2B:
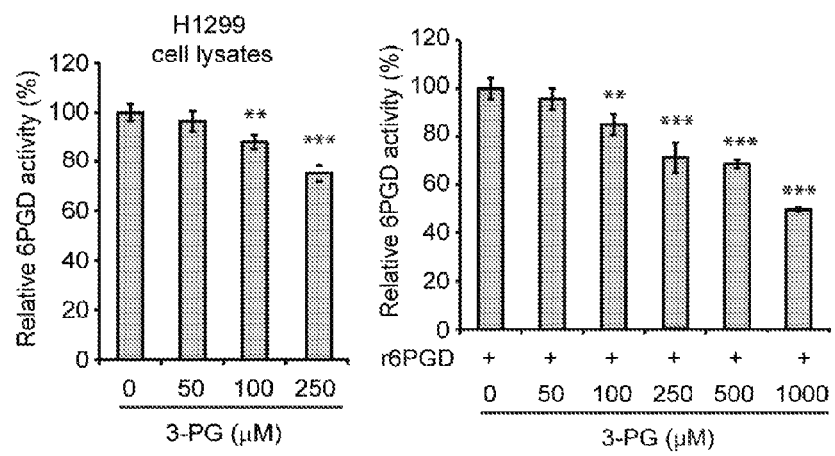
FIGS. 2A-F show data indicating attenuation of PGAM1 results in increased intracellular levels of 3-PG, which binds to and inhibits 6PGD by competing with its substrate 6-PG. (A-B) Enzyme activity of 6PGD in H1299 cell lysates (A) or recombinant 6PGD (r6PGD) (B) was determined in the presence of increasing concentrations of 3-PG. Relative 6PGD activity was normalized to the control samples without 3-PG treatment. 3-PG levels in control H1299 cells with empty vector and PGAM1 knockdown are 62.5±10.8 μM and 256±41.9 μM, respectively. (C) Thermal shift melting curves of 6PGD and 3PG. Thermal shift assay was performed to examine the protein (6PGD) and "ligand" (3PG) interaction. Change of melting temperature (Tm) in a dose-dependent manner at concentrations from 100 μM to 25 mM demonstrates that 3-PG directly binds to the protein. Kd for 6PGD-3-PG interaction was determined to be 460±40 μM. (D) The Dixon plot shows that 3-PG inhibits 6PGD and the dissociation constant (Ki) was determined. (E) The Lineweaver-Burk plot shows that 3-PG functions as a competitive inhibitor of 6PGD. (F) Thermal shift melting curves of 6PGD and 6PG. Thermal shift assay was performed to examine the protein (6PGD) and ligand (6PG) interaction. Change of melting temperature (Tm) in a dose-dependent manner at concentrations from 5 μM to 5 mM demonstrates that 6-PG directly binds to the protein. Kd for 6PGD-6PG interaction was determined to be 37±3 μM.
Figure 2C:
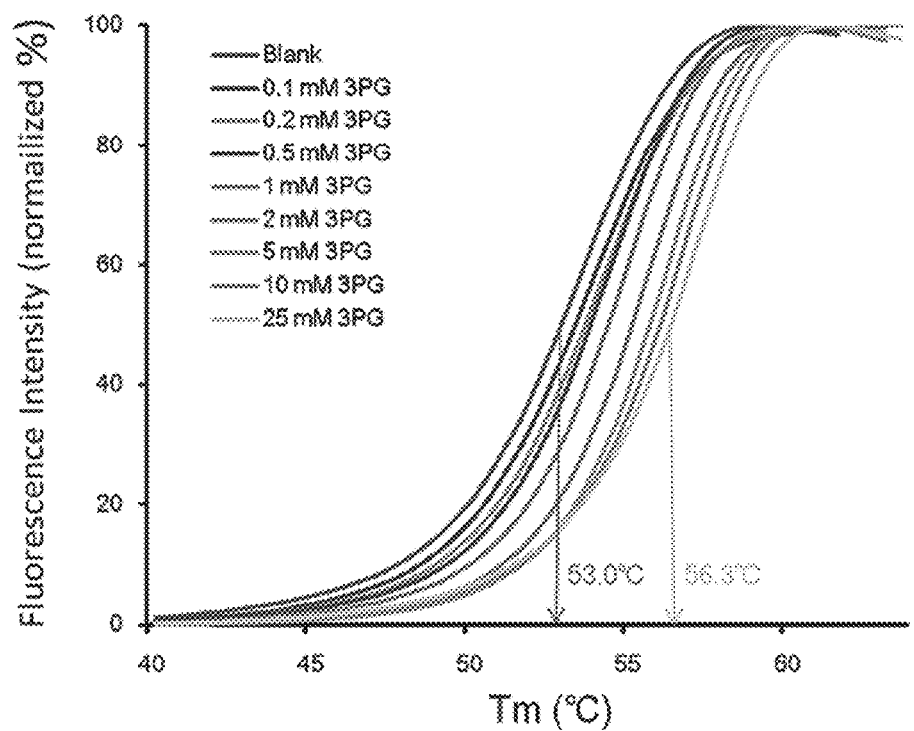
Figure 2D:
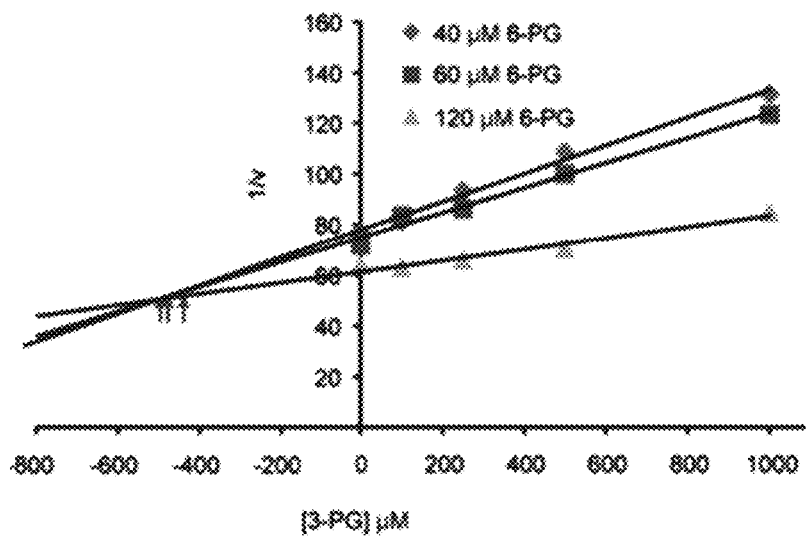
Figure 2E:
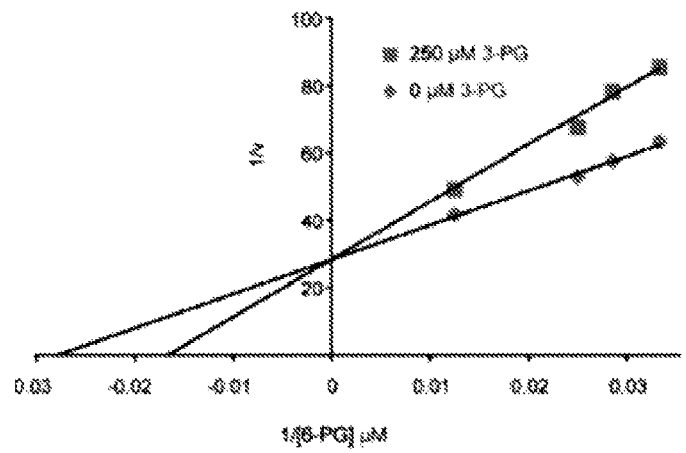

Structural studies revealed that both H11 and Y92 are directly proximal to the active site where both cofactor (2,3-BPG) and substrate (3-PG) bind, suggesting that Y92 is important for 2,3-BPG binding and PGAM1 activity, consistent with our observation that substitution of Y92 abolishes PGAM1 enzyme activity (FIG. 2d-2e). This is also consistent with a previous report that S14, T23, G24, R90, Y92, K99, R116 and R117 are involved in binding of cofactor 2,3-BPG and substrate 3-PG, which share the same binding pocket on PGAM1.

Y26 is also close to the cofactor binding site; since FGFR1 phosphorylates Y26 to activate PGAM1 in the presence of 2,3-BPG, this suggests a potential mechanism wherein Y26 phosphorylation by FGFR1 may induce conformational change to promote cofactor binding. To test this hypothesis, active rFGFR1 was incubated with purified, recombinant PGAM1 WT, Y26F or control Y133F mutant in an in vitro kinase assay, followed by incubation with 2,3-BPG fluorescent analogue (8-hydroxy-1,3,6-pyrenetrisulfonate). The decrease in fluorescence (ex: 362 nm, em: 520 nm) compared with buffer control was measured as 2,3-BPG binding ability.

Phosphorylation of PGAM1 WT or Y133F mutant by FGFR1 resulted in a significant increase in the amount of bound 2,3-BPG analogue, whereas substitution of PGAM1 Y26 abolished enhanced binding of cofactor in the presence of rFGFR1.

Moreover, a quantitative mass spectrometry based study revealed that the H11 phosphorylation levels of Y26F mutant is significantly lower compared to PGAM1 WT in an in vitro kinase assay using PGAM1 proteins incubated with rFGFR1 in the presence of 2,3-BPG. Similar results were obtained when using Flag-tagged mouse PGAM1 (mPGAM1) WT and Y26F from "rescue" H1299 cells with stable knockdown of endogenous human PGAM1 (hPGAM1) and rescue expression of Flag-mPGAM1 WT or Y26F mutant, respectively. These results suggest that Y26 phosphorylation enhances PGAM1 activity by promoting 2,3-BPG binding to PGAM1 and consequently H11 phosphorylation.

An antibody was generated that specifically recognizes PGAM1 phospho-Y26. PGAM1 was phosphorylated at Y26 by rFGFR1 in vitro; inhibiting FGFR1 decreased PGAM1 Y26 phosphorylation in H1299 lung cancer cells and KG1a leukemia cells. In addition, FLT3 and JAK2 also directly phosphorylated PGAM1 at Y26 in vitro, and inhibition of FLT3-ITD by TKI258 and JAK2 by AG490 resulted in decreased Y26 phosphorylation of PGAM1 in the pertinent human cancer cell lines. It was found that PGAM1 is commonly expressed and phosphorylated at Y26 in diverse leukemia and multiple myeloma cells associated with various constitutively activated tyrosine kinase mutants, as well as various human solid tumor cells including lung, prostate, breast and head and neck cancer cells.

Y26 Phosphorylation of PGAM1 Contributes to Control of 3-PG and 2-PG Levels, Promoting Cancer Cell Metabolism, Proliferation and Tumor Development.

A specific phospho-PGAM1 antibody (pY26) was developed and used to identify that PGAM1 is commonly expressed and phosphorylated at Y26 in diverse human leukemia cell lines associated with distinct LTKs (FIG. 13A). Indeed, FGFR1 (FIG. 13B), JAK2 (FIG. 13C) and FLT3 (data not shown) directly phosphorylated PGAM1 at Y26 in vitro, and inhibition of FGFR1 by TKI258 and JAK2 by AG490 resulted in decreased Y26 phosphorylation of PGAM1 in the pertinent human cancer cell lines. "Rescue" H1299 were next generated cells by RNAi-mediated stable knockdown of endogenous hPGAM1 and rescue expression of Flag-tagged mPGAM1 WT or less active Y26F mutant (FIG. 13D). Compared with the mPGAM1 WT rescue cells, Y26F cells have increased 3-PG (FIG. 13E; left) and decreased 2-PG (FIG. 13E; right) levels, as well as reduced cell proliferation (FIG. 13F), while treatment with methyl-2-PG significantly rescues these phenotypes. Y26F cells also demonstrated attenuated tumor growth potential in xenograft nude mice compared to control mPGAM1 WT rescue cells (FIG. 13G). These data together suggest that PGAM1 Y26 phosphorylation levels are important to control intracellular 3-PG and 2-PG levels, which confers both metabolic and proliferative advantages to cancer cells, representing an additional, acute regulatory mechanism underlying PGAM1 upregulation in cancer cells.

PGAM1 Controls Intracellular 3-PG and 2-PG Levels, and is Important for Glycolysis and Anabolic Biosynthesis in Cancer Cells, as Well as Cancer Cell Proliferation and Tumor Growth To better understand how cancer cells coordinate glycolysis and anabolic biosynthesis, the effects of targeted downregulation of the glycolytic enzyme PGAM1 was examined. Stable knockdown of PGAM1 in lung cancer H1299, breast cancer MDA-MB231, acute myeloid leukemia Molm14 and head and neck cancer 212LN cells resulted in decreased PGAM1 activity. Global Metabolic Profiling (Metabolon) was performed using cell lysate samples of parental H1299 cells and cells with stable knockdown of PGAM1. The results indicate that PGAM1 knockdown results in altered intracellular concentrations of 118 biochemicals (61 upregulated and 57 downregulated) with $p<0.05$ using Welch's Two Sample t-tests. Among these biochemicals, the PGAM1 substrate 3-PG levels are increased in PGAM1 knockdown compared to control cells. In consonance with this observation, attenuation of PGAM1 by shRNA in diverse cancer cells leads to not only increased 3-PG (FIG. 1A) but also decreased 2-PG (FIG. 1B) levels compared to corresponding control cells harboring an empty vector. The intracellular levels of 3-PG and 2-PG determined using different methods are comparable. In addition, stable overexpression of PGAM1 in 3T3 cells results in increased 2-PG and decreased 3-PG levels, compared to control parental 3T3 cells. These results suggest a role for PGAM1 controlling the metabolite levels of its substrate 3-PG and product 2-PG in cancer cells.

The role of PGAM1 in cancer cell metabolism was examined. Compared to vector control cells, stable knockdown of PGAM1 results in decreased glycolytic rate (FIG. 1C) and lactate production (FIG. 1D), as well as reduced glucose-dependent biosynthesis of RNA and lipids, accompanied by reduced NADPH/NADP+ ratio (FIG. 1E-1G, respectively). Since the PPP produces NADPH and R5P to contribute to macromolecular biosynthesis, whether PGAM1 contributes to PPP flux was examined. Indeed, oxidative PPP flux is reduced in PGAM1 knockdown compared to control vector cells (FIG. 1H). Interestingly, attenuation of PGAM1 in cancer cells does not affect glucose uptake rate, or intracellular ATP levels (FIG. 1I) or O2 consumption rate (FIG. 1J) in either the presence or absence of ATP synthase inhibitor oligomycin. These results suggest that downregulation of PGAM1 attenuates glycolysis, PPP and biosynthesis, but does not significantly affect glucose uptake or intracellular ATP levels.

Figure 1K:
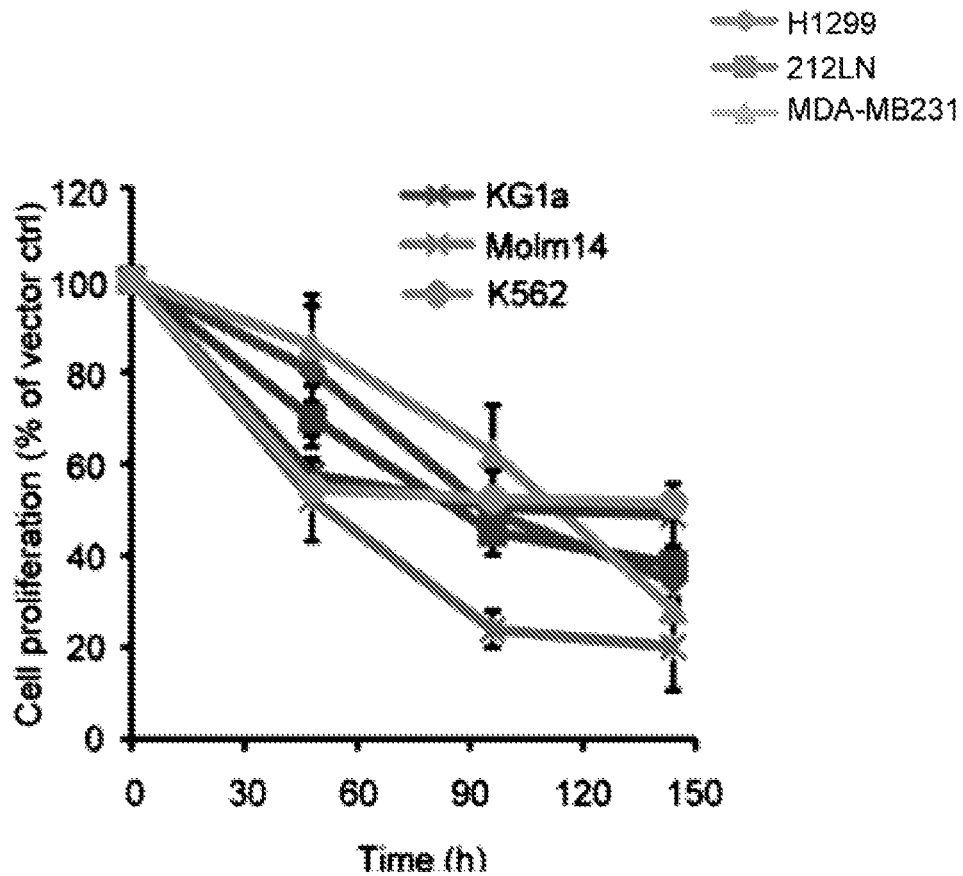
Figure 1L:
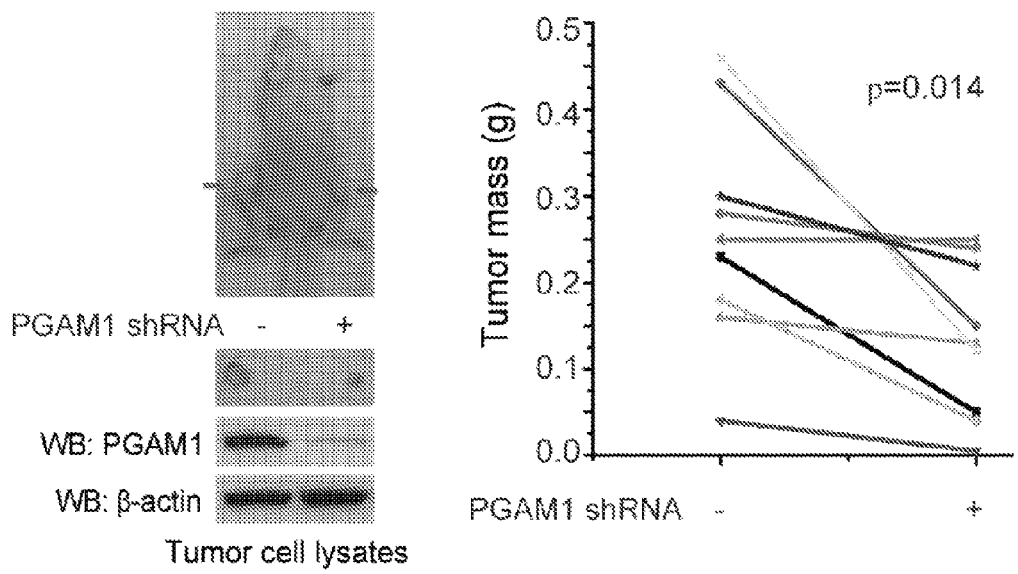

In addition, stable knockdown of PGAM1 results in decreased cell proliferation in diverse human cancer and leukemia cells (FIG. 1K). Moreover, a xenograft experiment was performed in which nude mice were subcutaneously injected with control H1299 cells harboring an empty vector on the left flank and PGAM1 knockdown H1299 cells on the right flank (FIG. 1L; left). The mice were monitored for tumor growth over a 6-week time period. The masses of tumors derived from PGAM1 knockdown H1299 cells were significantly reduced compared to those of tumors formed by vector control cells (FIG. 1L; right).

PGAM1 Knockdown Results in Elevated Levels of 3-PG, which Binds to and Inhibits 6PGD by Competing with its Substrate 6-Phosphogluconate (6-PG)

The molecular mechanism by which PGAM1 regulates the PPP was explored. Experiments suggests that the abnormally high levels of 3-PG in PGAM1 knockdown cells may account for inhibition of oxidative PPP flux (FIG. 1). To test this hypothesis, the effect of 3-PG was examined on glucose-6-phosphate dehydrogenase (G6PD), the first and most important enzyme of the oxidative PPP, which produces NADPH, and 6-phosphogluconate dehydrogenase (6PGD), an enzyme that also produces NADPH while converting 6-phosphogluconate into ribulose 5-phosphate in the presence of NADP+. In vitro 6PGD and G6PD assays were performed in the presence of increasing concentrations of 3-PG. Physiological concentrations of 3-PG in human cells are reported to be approximately 50-80 µM. In H1299, MDA-MB231 and Molm14 cells, the 3-PG levels are approximately 60-80 µM in control vector cells and 200-300 µM in PGAM1 knockdown cells, while the 3-PG concentrations are approximately 160 µM and 310 µM in 212LN control and PGAM1 knockdown cells, respectively. Thus, the effects of increasing concentrations of 3-PG on G6PD and 6PGD enzyme activities was examined according to the aforementioned physiological 3-PG levels in tumor cells.

Treatment with 3-PG concentrations analogous to those in PGAM1 knockdown H1299 cells (~250 µM) results in decreased enzyme activity of 6PGD (FIG. 2A) in H1299 cell lysates or recombinant 6PGD (r6PGD) (FIG. 2B), whereas the physiological 3-PG concentrations determined in control H1299 cells (~60 µM) do not significantly affect 6PGD enzyme activity in both experiments. In control experiments, treatment with increasing concentrations of 3-PG did not significantly affect G6PD activity in H1299 cell lysates or rG6PD activity. In addition, 2-PG did not affect 6PGD enzyme activity in H1299 cell lysates or r6PGD activity. These results suggest that abnormally high levels of 3-PG, as in PGAM1 knockdown cells, may selectively and directly inhibit 6PGD but not G6PD.

To examine whether 3-PG binds to and inhibits 6PGD, a thermal melt shift assay was performed to examine the interaction of protein (6PGD) and "ligand" (3-PG). Incubation of increasing concentrations of 3-PG raises 6PGD melting temperature (Tm) in a dose-dependent manner, suggesting that 3-PG directly binds to the protein (FIG. 2C). The Kd value for protein-"ligand" interaction was calculated to be 460±40 µM. Moreover, kinetics studies were performed on the inhibition of 6PGD by 3-PG. As shown in FIG. 2D, the Dixon plot indicates that 3-PG binds and inhibits 6PGD. The inhibition constant (Ki) was determined to be 489±13 µM, in agreement with the Kd determined.

Figure 2F:
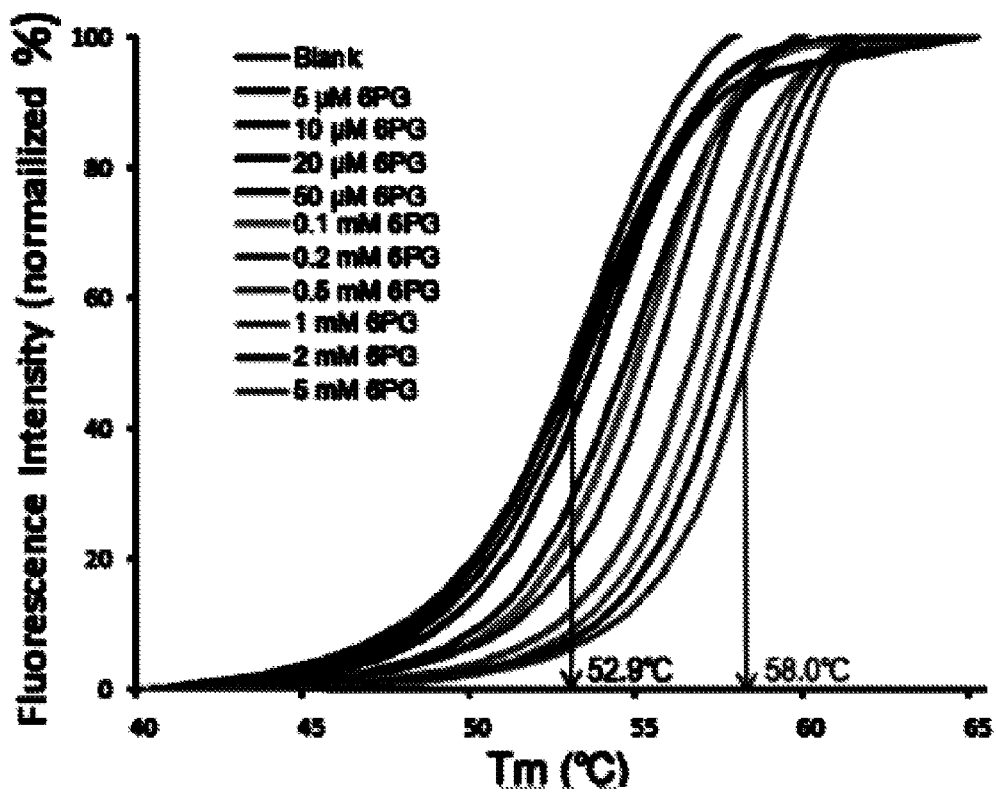

The intracellular concentration of 6-PG in H1299, MDA-MB231 and 212LN cells were determined to be 34.9±2.1 µM, 37.6±0.7 µM and 24.9±0.4 µM, respectively. Additional enzyme kinetics assays were performed to test whether 3-PG at a concentration analogous to that in PGAM1 knockdown H1299 cells (~250 µM) functions as a competitive or non-competitive inhibitor of 6PGD in the presence of physiological concentrations of 6-PG (~35 µM). As shown in FIG. 2E, the Lineweaver-Burk plot demonstrates that 3-PG functions as a competitive inhibitor of 6PGD. Since the Kd value for protein (6PGD)-ligand (6-PG) interaction was calculated to be 37±3 µM in a thermal melt shift assay (FIG. 2F), these data together suggest that at physiological concentrations, 3-PG (~60-80 µM) cannot effectively compete with 6-PG (35 µM) to inhibit 6PGD in cancer cells; however, upon attenuation of PGAM1, elevated cellular 3-PG levels (~250-300 µM) result in reduced 6PGD enzyme activity.

To further understand the structural properties of 3-PG mediated inhibition of 6PGD, the apo-form of 6PGD (1.39 Å) was crystallized soaked with 3-PG to obtain the 3-PG-bound form of 6PGD (1.53 Å). The Fo-Fc density analysis revealed that the electron density of 3-PG was located in the active site of the 3-PG-bound 6PGD structure but not in the apo-6PGD structure. 3-PG interacts with several residues (Y191, T262, R287, R446) in the active site of 6PGD that are important for substrate binding and enzymatic activity of 6PGD. Different conformations were observed for Arg 446 and His 452 in the 3-PG-bound 6PGD structure compared to the apo-form 6PGD structure. An alignment of three different 6PGD structures with bound NADP, 6-PG and 3-PG shows an overlap of 3-PG and 6-PG in the active site. Together, these results demonstrate that 3-PG directly binds to 6PGD and inhibits 6PGD enzyme activity by competing with the cognate substrate 6-PG, representing a molecular mechanism to explain how PGAM1, as a glycolytic enzyme, contributes to the regulation of the oxidative PPP and consequently anabolic biosynthesis.

Rescue of Reduced 2-PG Levels in PGAM1 Knockdown Cells Results in Decreased 3-PG Levels by Activating 3-Phosphoglycerate Dehydrogenase (PHGDH)

Figure 4A:
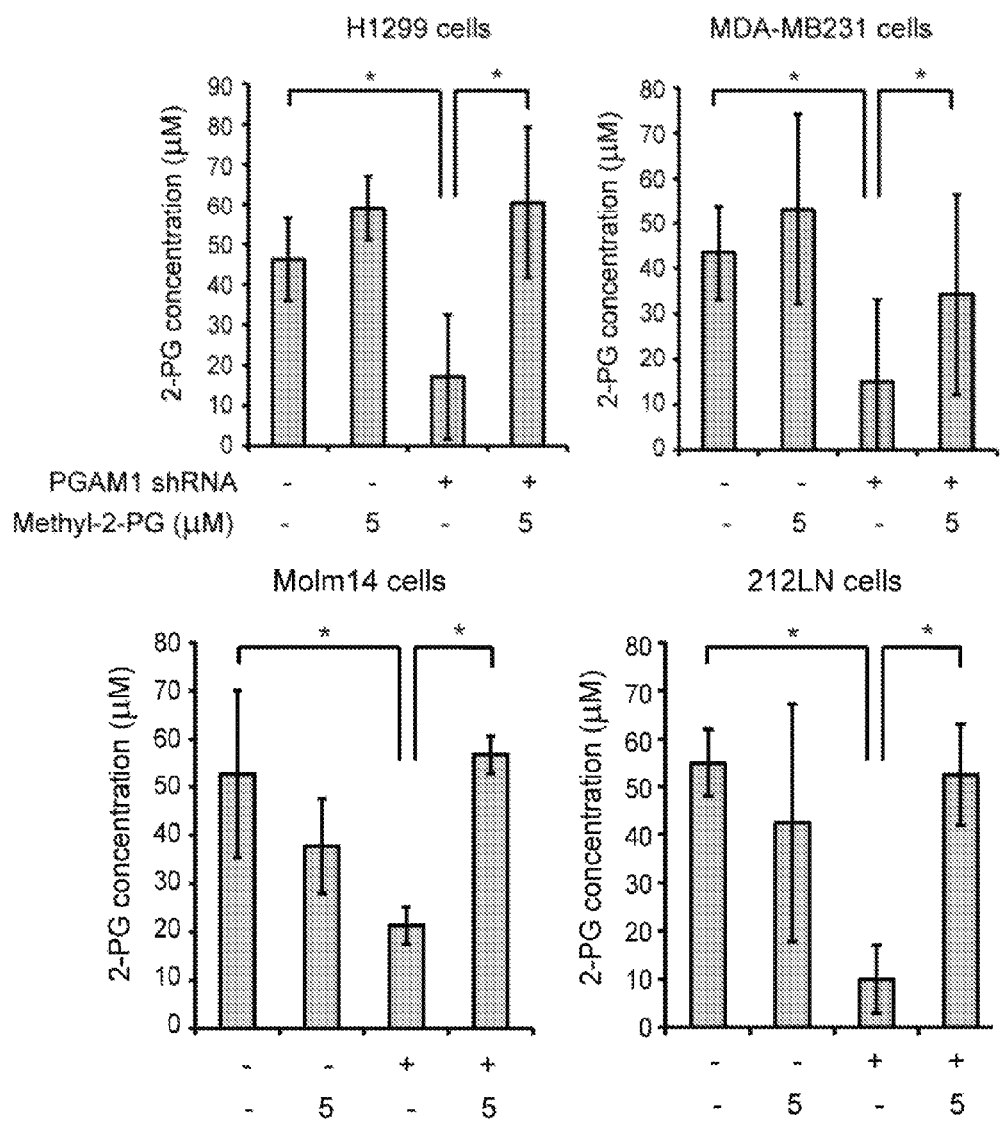
FIGS. 4A-F show data indicating rescue of reduced 2-PG levels in PGAM1 knockdown cells reverses the phenotypes due to attenuation of PGAM1. (A) 2-PG levels in diverse cancer cells with stable knockdown of PGAM1 were determined in the presence and absence of cell permeable methyl-2-PG. (B-F) H1299 cells with stable knockdown of PGAM1 were tested for lactate production (B), oxidative PPP flux (C) and biosynthesis of RNA (D) and lipids (E), as well as cell proliferation (F) in the presence and absence of methyl-2-PG.
Figure 4B:
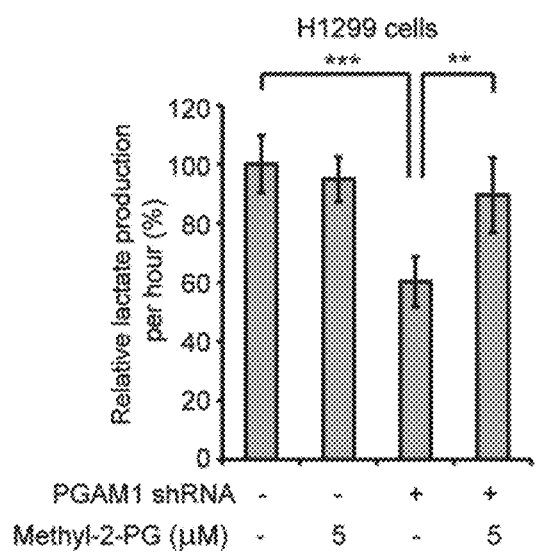
Figure 4C:
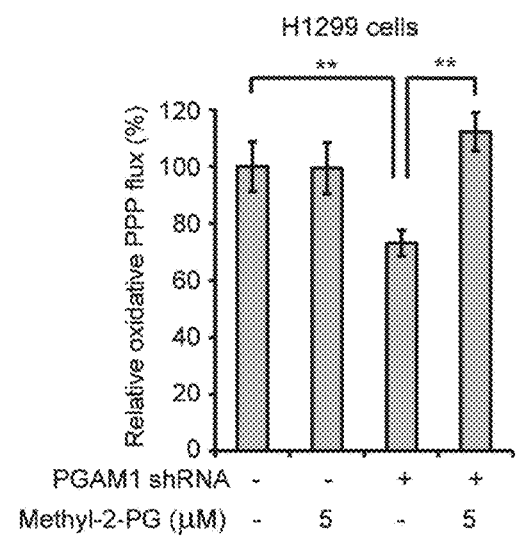
Figure 4D:
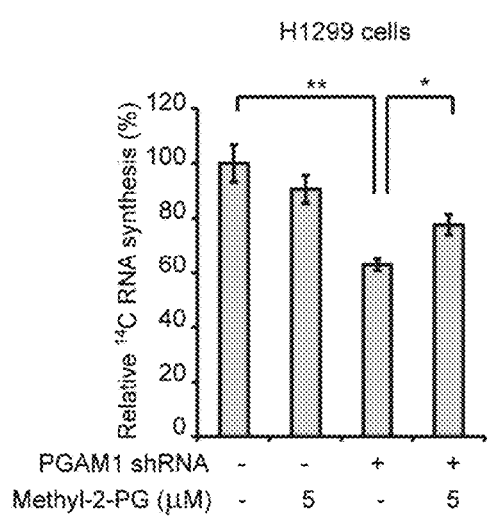
Figure 4E:
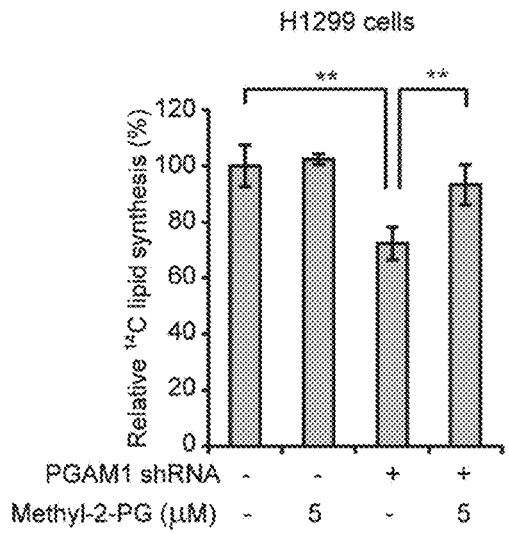
Figure 4F:
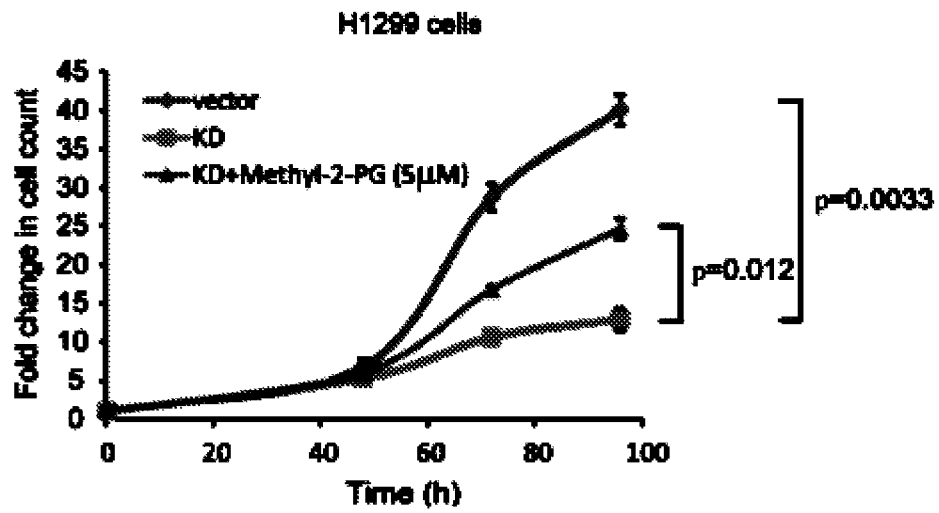

In order to examine the effect of decreased 2-PG levels on cancer cell metabolism, the aforementioned PGAM1 knockdown cancer cells were treated with a cell permeable agent, methyl-2-PG, which converts to 2-PG in cells. In diverse PGAM1 knockdown cancer cells, treatment with methyl-2-PG results in increased 2-PG cellular levels comparable to those in the corresponding control vector cells (FIG. 4A). Methyl-2-PG treatment rescues the reduced lactate production (FIG. 4B) but has no significant effect on intracellular ATP levels in H1299 cells with stable knockdown of PGAM1 compared to control vector cells. This result suggests that rescuing cellular 2-PG levels reverses the inhibitory effect of PGAM1 knockdown on glycolysis and allows downstream glycolytic reactions to resume and ultimately produce lactate. However, such rescued glycolytic activity does not affect ATP levels, which is consistent with our previous observation (FIG. 1I-1J).

Surprisingly, methyl-2-PG treatment rescues the decreased oxidative PPP flux and biosynthesis of RNA and lipids, as well as partially restores the reduced cell proliferation in H1299 PGAM1 knockdown cancer cells compared to the corresponding control vector cells (FIG. 4C-FIG. 4F). Similar results were obtained using MDA-MB231 vector and PGAM1 knockdown cells. These data suggest that the increased 2-PG levels in PGAM1 knockdown cells provide a feedback mechanism to rescue the abrogated PPP and anabolic biosynthesis upstream of PGAM1.

Figure 5A:
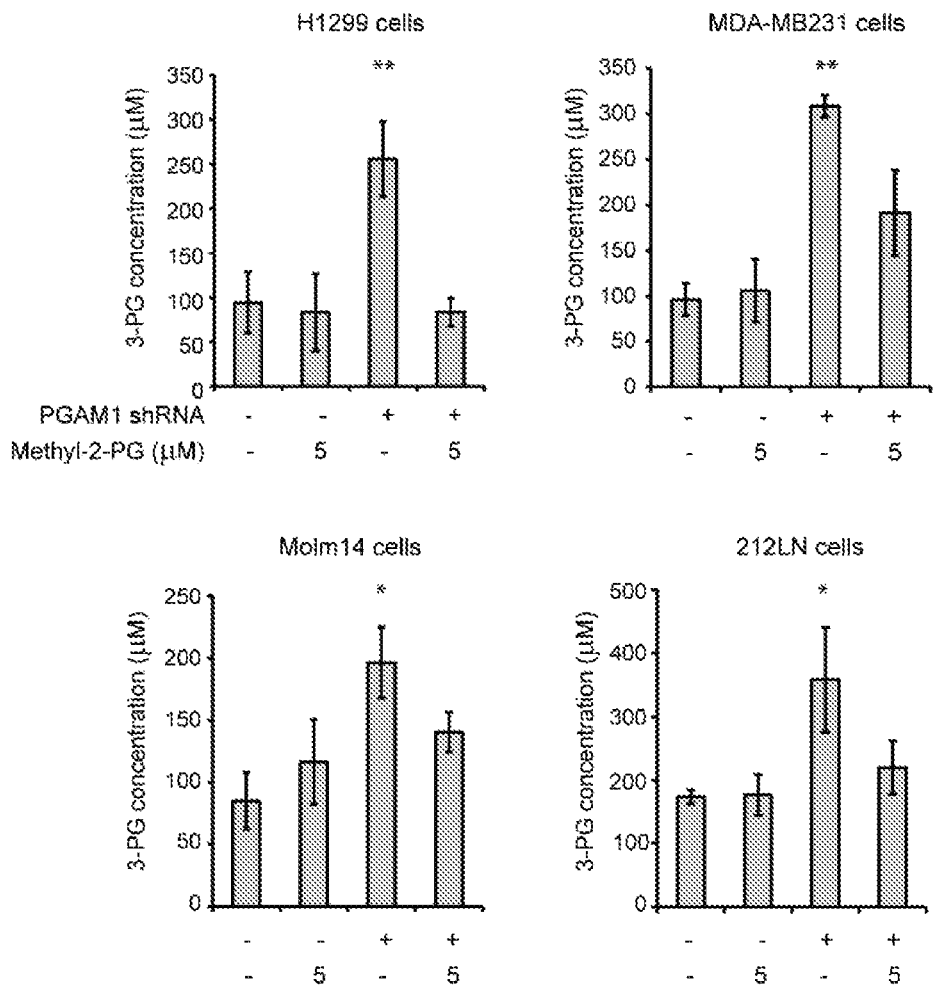

This hypothesis was tested by examining the effect of rescued 2-PG levels on 3-PG concentrations in PGAM1 knockdown cells. Treatment with methyl-2-PG results in decreased 3-PG concentrations in diverse PGAM1 knockdown cells to levels that are comparable to the 3-PG concentrations in the corresponding control vector cells (FIG. 5A). These results further suggest that PGAM1 controls 2-PG levels in cancer cells, which contributes to PGAM1-dependent coordination of glycolysis and anabolic biosynthesis by adjusting 3-PG levels.

The molecular mechanism underlying 2-PG dependent feedback regulation of intracellular 3-PG levels was evaluated. Besides conversion to 2-PG catalyzed by PGAM1 in glycolysis, 3-PG also serves as a precursor for serine synthesis and can be converted to 3-phosphohydroxypyruvate (pPYR) by PHGDH. Since PGAM1 activity is attenuated in PGAM1 knockdown cells, it is possible that the rescued cellular 2-PG levels by methyl-2-PG treatment decreases 3-PG levels by activating PHGDH. This hypothesis was tested by examining the effect of 2-PG on PHGDH activity. PGAM1 knockdown cells were used to exclude the endogenous PGAM1 effect on 3-PG and 2-PG in the PHGDH enzyme activity reactions. Indeed, treatment with 2-PG concentrations equivalent to those determined in control H1299 cells (~45 µM) or methyl-2-PG treated PGAM1 knockdown cells (60 µM) results in higher PHGDH enzyme activity in H1299 PGAM1 knockdown cell lysates (FIG. 5B; left). Similar results were obtained by treating 212LN PGAM1 knockdown cell lysates with increasing concentrations of 2-PG (FIG. 5B; right). Moreover, treatment with increasing concentrations of 2-PG results in increased enzyme activity of recombinant PHGDH (rPHGDH) (FIG. 5C). In contrast, 2-PG concentrations that correspond to those determined in PGAM1 knockdown cells (~15 µM) did not significantly affect PHGDH activity. Together, these studies reveal a feedback mechanism by which cellular 2-PG levels contribute to control of 3-PG levels in cells through regulation of PHGDH.

Figure 5E:
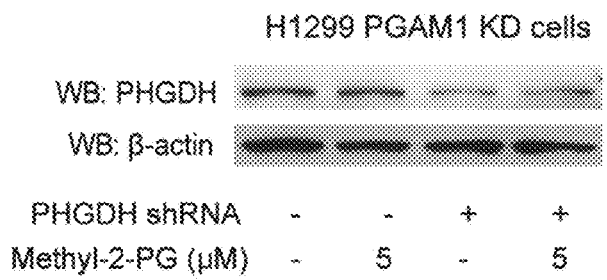
Figure 5F:
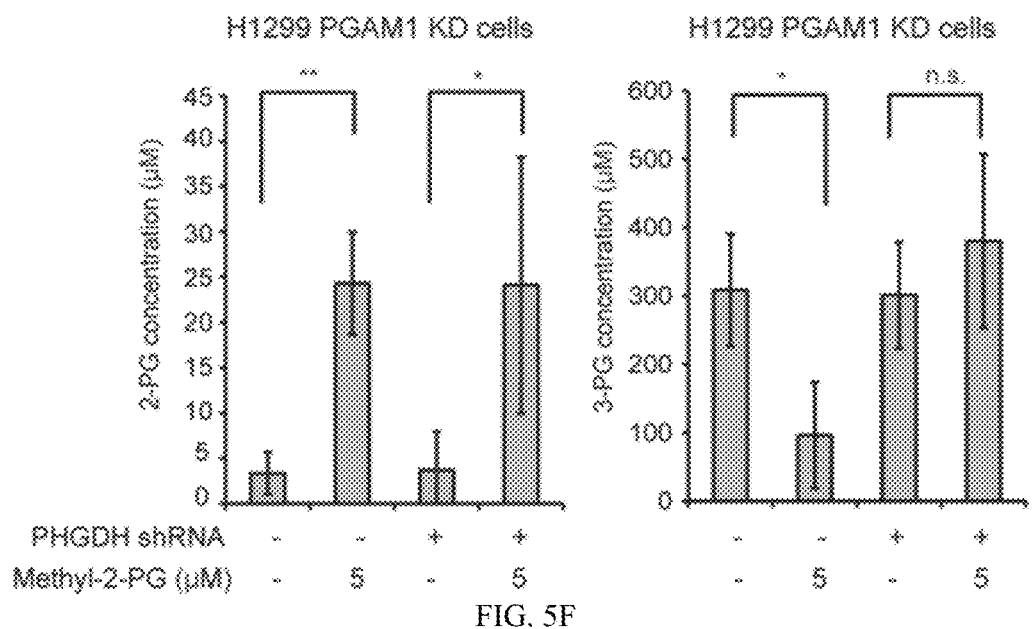
Figure 5G:
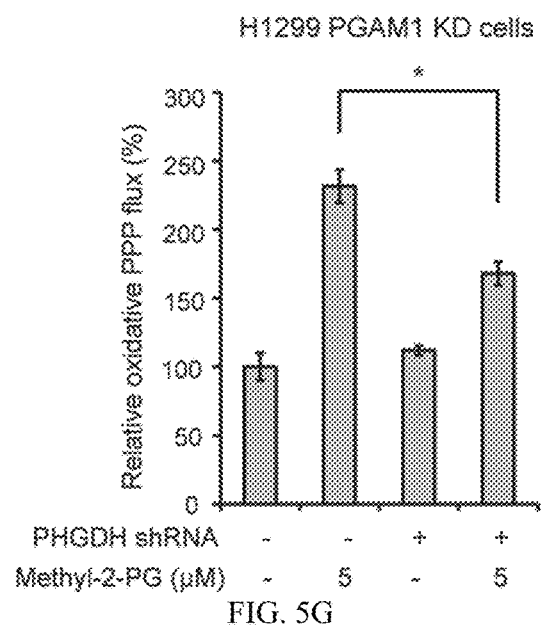
Figure 5H:
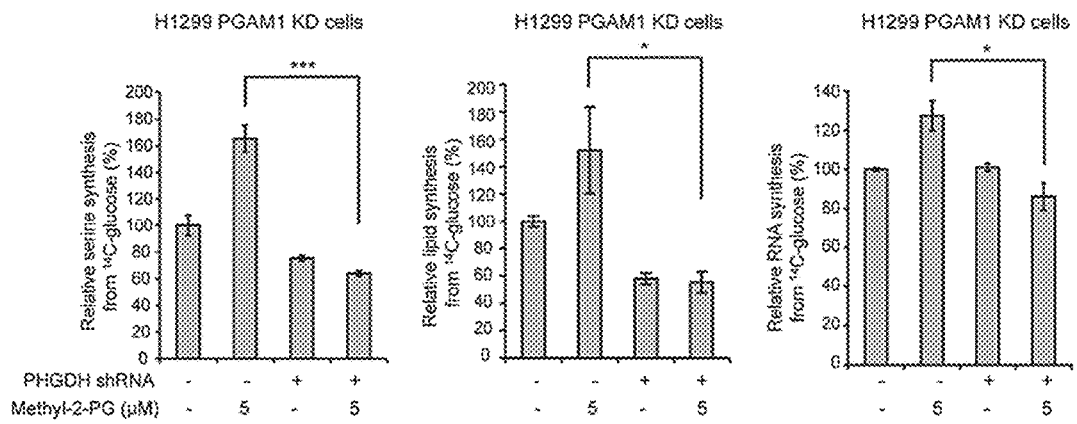

In addition, stable knockdown of PGAM1 results in significantly decreased serine biosynthesis, while treatment with methyl-2-PG rescues the phenotype (FIG. 5D). Moreover, shRNA-mediated knockdown of PHGDH (FIG. 5E) does not affect rescued 2-PG levels in PGAM1 knockdown cells upon treatment with methyl-2-PG, while PHGDH knockdown abolishes the methyl-2-PG dependent decrease of the elevated 3-PG levels in H1299 PGAM1 knockdown cells (FIG. 5F, left and right, respectively). These data support the hypothesis that PGAM1 controls 2-PG levels to regulate PHGDH, which consequently regulates 3-PG levels by diverting 3-PG in serine biosynthesis. Furthermore, knockdown of PHGDH in PGAM1 stable knockdown cells reverses the methyl-2-PG treatment dependent rescue of oxidative PPP flux as well as biosynthesis of serine, lipids and RNA (FIG. 5G-5H, respectively). These data together suggest that, besides being a glycolytic metabolite, 2-PG may also signal through PHGDH to provide regulation of PPP flux and anabolic biosynthesis, at least in part by regulating 3-PG levels.

Figure 6A:
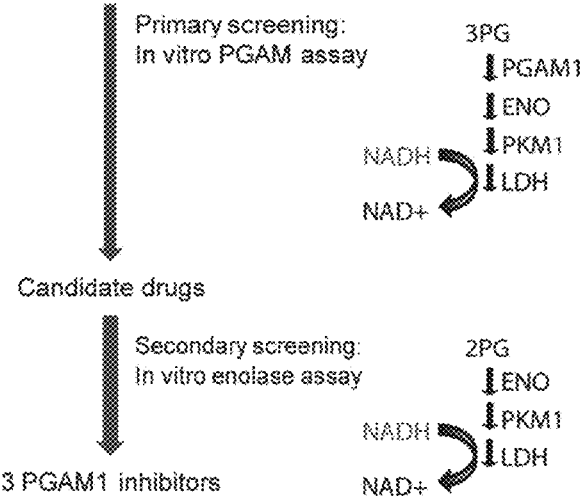
FIGS. 6A-G show illustrations and data on identification and characterization of small molecule PGAM1 inhibitor, PGMI-004A. (A) Schematic representation of the primary and secondary screening strategies to identify lead compounds as PGAM1 inhibitors. (B) Structure of alizarin and its derivatives alizarin Red S and PGAM inhibitor (PGMI)-004A. (C) PGMI-004A inhibits PGAM1 with an IC50 of 13.1 μM, which was determined by incubating purified human PGAM1 proteins with increasing concentrations of PGMI-004A. The error bars represent mean values+/−SD from three replicates of each sample. (D) Kd value was determined as 7.2±0.7 μM by incubating purified human PGAM1 proteins with increasing concentrations of PGMI-004A. The fluorescence intensity (Ex: 280 nm, em: 350 nm) from Tryptophan was measured. (E) Competitive binding assay of PGMI-004A with recombinant PGAM1 protein in the presence of increasing concentrations of PGAM1 substrate 3-PG. Increased free PGAM1 was determined by an increase in fluorescence intensity. (F) Dixon plot analysis of PGAM1 enzyme assay in the presence of different concentrations of PGMI-004A and 3-PG. The reaction velocity (v) was determined by the rate of the decrease in fluorescence (ex: 340 nm, em: 460 nm) by NADH oxidation. Ki was determined to be 3.91±2.50 μM. (G) Thermal shift melting curves of PGAM1 and PGMI-004A. Thermal shift assay was performed to examine the protein (PGAM1) and "ligand" (inhibitor PGMI-004A) interaction. Change of melting temperature (Tm) in a dose-dependent manner at concentrations from 2.504 to 80 μM demonstrates that PGMI-004A directly binds to the protein. Kd for PGAM1-PGMI-004A interaction was determined to be 9.4±2.0 μM.
Figure 6B:
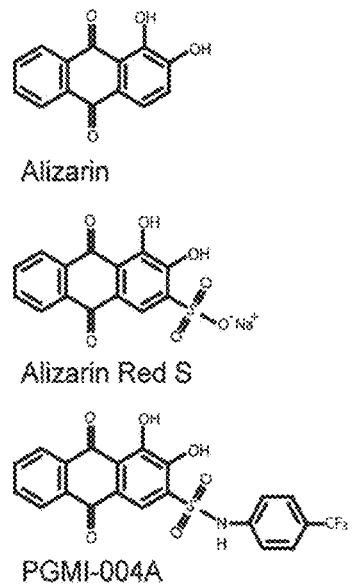

PGAM1 Enzyme Activity Strikes a Balance Between 3-PG and 2-PG Levels, which Coordinates Glycolysis and Biosynthesis to Promote Cancer Cell Proliferation In order to study the role of PGAM1 enzyme activity in cancer metabolism and tumor development, a small molecule inhibitor of PGAM1 was identified. Currently the only reported PGAM1 inhibitor is MJE3, which specifically inhibits PGAM1 activity exclusively in intact cells, probably by targeting the active site of PGAM1 with certain modifications in vivo (Evans et al., 2007; Evans et al., 2005). A screening strategy was designed using coupled PGAM1 and enolase assays and identified three lead small molecule compounds, including alizarin, as PGAM1 inhibitors from a library of FDA approved 2,000 small molecule compounds (FIG. 6A). 1,2-Dihydroxyanthraquinone a.k.a. alizarin (C14H8O4) (FIG. 6B; top) is a prominent dye, originally derived from the roots of plants of the *Madder* genus. Treatment with alizarin results in decreased proliferation of human leukemia KG1a cells in a dose-dependent manner.

Alizarin Red S (FIG. 6B; middle) was identified as a more potent PGAM1 inhibitor from a group of alizarin derivatives. Alizarin Red S derivatives were designed by adding hydrophobic groups through a sulfonamide bond. Among these compounds, PGAM1 inhibitor 004A (PGMI-004A) (FIG. 6B; bottom), is less potent than Red S; however, in vitro, it demonstrates enhanced potency to inhibit PGAM1 in leukemia KG1a cells compared to its parental compounds. This may be due to the fact that PGMI-004A is more hydrophobic than alizarin and alizarin Red S, which confers better cell permeability.

Figure 6C:
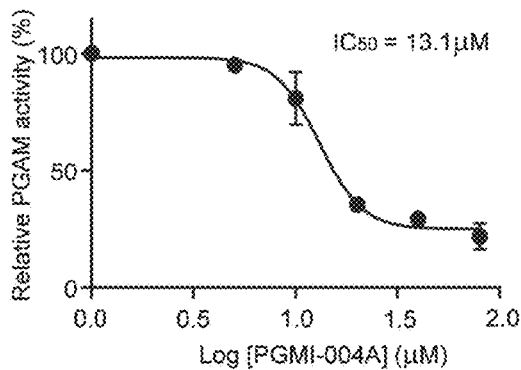
Figure 6D:
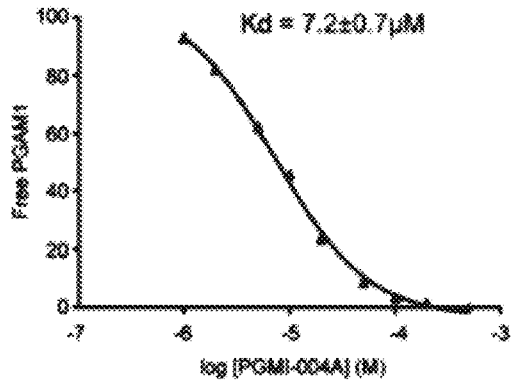
Figure 6E:
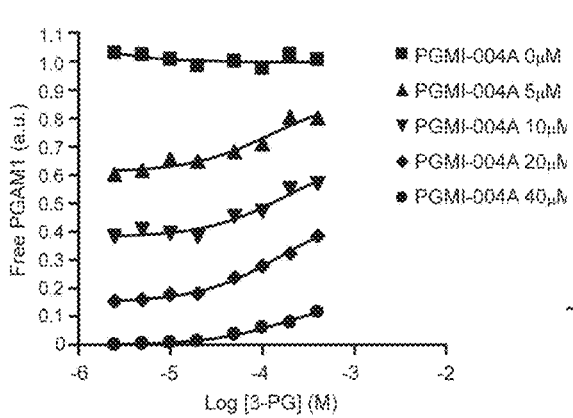
Figure 6F:
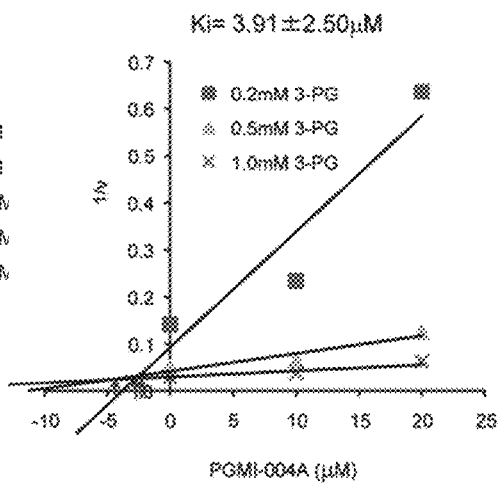
Figure 6G:
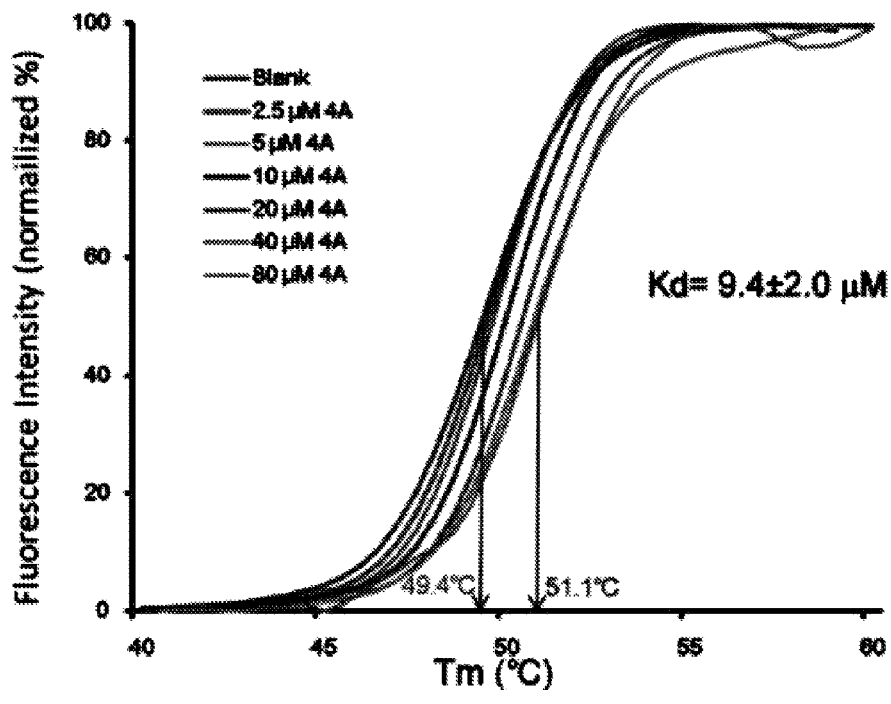

PGMI-004A inhibits PGAM1 with an $IC_{50}$ of approximately 13.1 µM (FIG. 6C) and the $K_d$ value of the PGMI-004A-PGAM1 interaction was determined to be 7.2±0.7 µM from fluorescence-based binding assay (FIG. 6D). In a competitive binding assay where PGMI-004A was incubated with recombinant PGAM1 proteins in the presence of different concentrations of PGAM1 substrate 3-PG, increasing concentrations of 3-PG caused an increase in the fluorescence intensity from PGMI-004A-unbound form of PGAM1 in the presence of different concentrations of PGMI-004A, but not in the absence of PGMI-004A (FIG. 6E). This suggests that PGMI-004A may allosterically modulate the enzyme activity of PGAM1. The Ki value was determined to be 3.91±2.50 µM using Dixon plot analysis (FIG. 6F). In addition, a thermal melt shift assay was performed to examine the interaction of protein (PGAM1) and ligand (PGMI-004A). Incubation of increasing concentrations of PGMI-004A raises PGAM1 melting temperature (Tm) in a dose-dependent manner, suggesting that PGMI-004A directly binds to the protein (FIG. 6G). The $K_d$ value for protein-ligand interaction was calculated to be 9.4±2.0 µM. Together, these results suggest that PGMI-004A directly binds to PGAM1 and inhibits its enzyme activity.

Figure 7A:
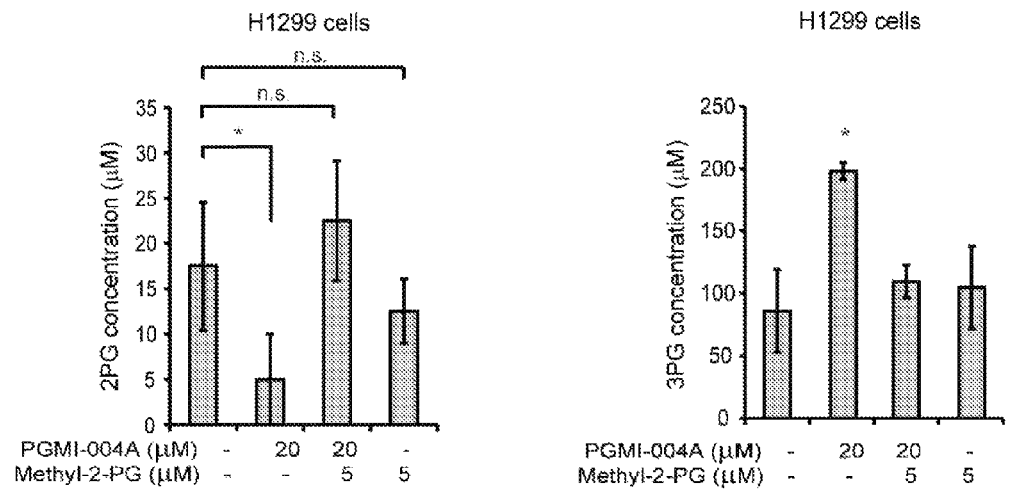
Figures 7B, 7C:
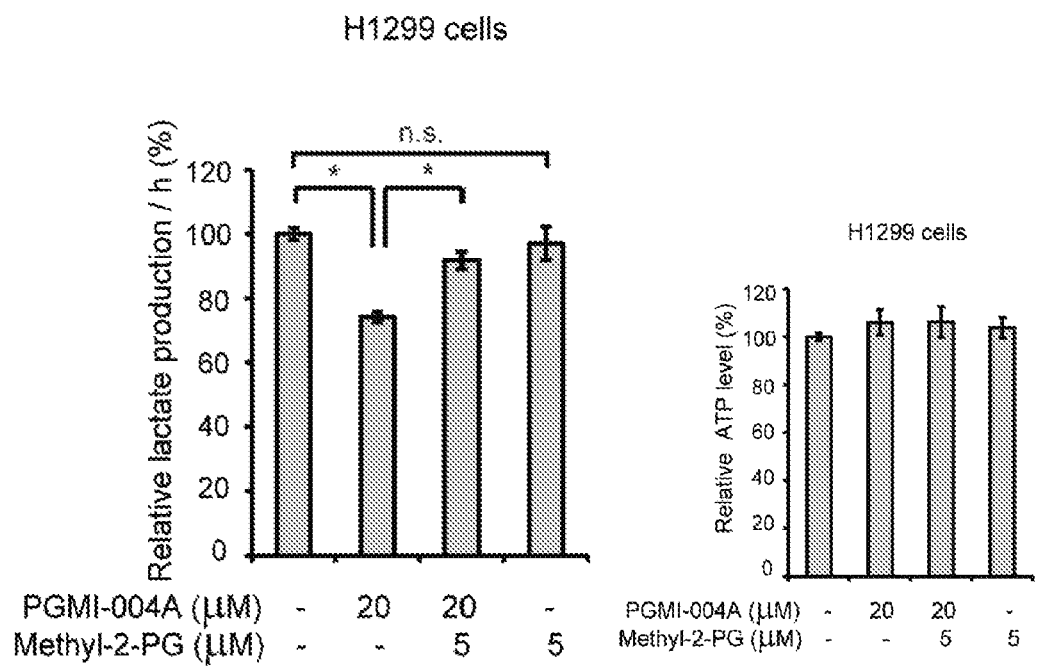
Figures 7D, 7E:
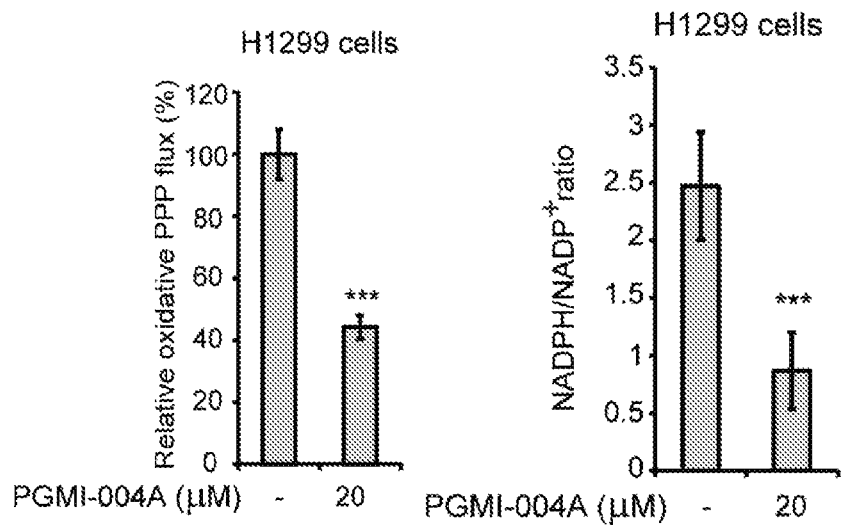
Figure 7F:
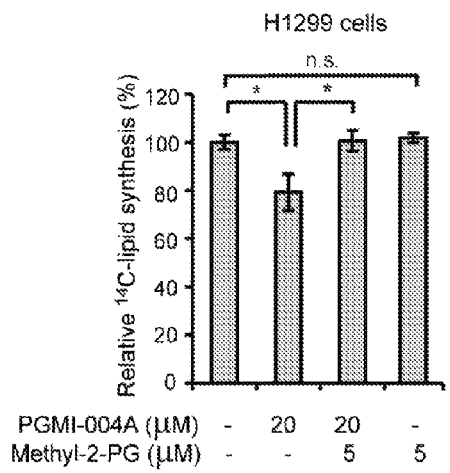
Figure 7G:
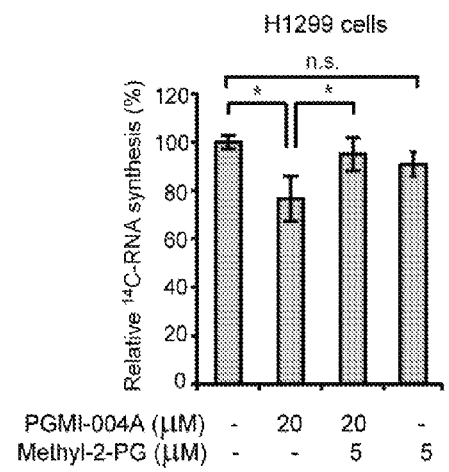
Figure 7H:
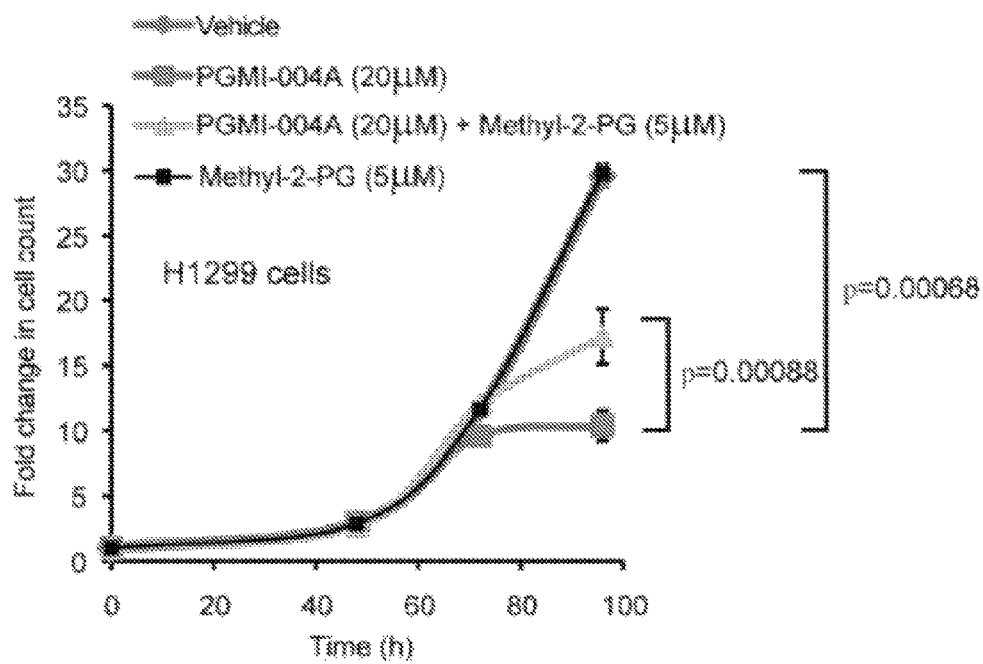

Inhibition of PGAM1 activity by PGMI-004A treatment results in decreased 2-PG and increased 3-PG levels in H1299 cells, which could be rescued by treatment with methyl-2-PG (FIG. 7A). Moreover, treatment with PGMI-004A results in significantly reduced lactate production that was rescued by methyl-2-PG treatment (FIG. 7B), but has no significant effect on intracellular ATP levels (FIG. 7C). In consonance with these observations, the rescued lactate production due to methyl-2-PG treatment was abolished when enolase was knocked down or inhibited by specific inhibitor NaF in PGMI-004A treated cells. These results also suggest that rescued 2-PG derived from methyl-2-PG is metabolized by cells to restore the decreased glycolysis due to PGAM1 inhibition in cancer cells. PGMI-004A treatment results in decreased oxidative PPP flux (FIG. 7D) and NADPH/NADP+ ratio (FIG. 7E), as well as reduced biosynthesis of lipids and RNA (FIG. 7F-7G, respectively) and cell proliferation (FIG. 7H) in H1299 cells. These phenotypes are similar to those observed in PGAM1 knockdown cells, which could be significantly rescued by treatment with methyl-2-PG, suggesting that PGMI-004A targets PGAM1 to inhibit cancer cell metabolism and proliferation.

PGMI-004A treatment results in decreased cell proliferation of diverse human cancer and leukemia cells (FIG. 7I-7J; FIG. 10E-10H), but not control human dermal fibroblasts (HDF), human foreskin fibroblasts (HFF), human HaCaT keratinocyte cells and human melanocyte PIG1 cells (FIGS. 7K and 10I), suggesting minimal non-specific toxicity of PGMI-004A in normal, proliferating human cells.

Targeting PGAM1 by PGMI-004A Treatment Inhibits Cancer Cell Proliferation and Tumor Growth, and Alters 3-PG and 2-PG Levels in Primary Leukemia Cells from Human Patients, Leading to Attenuated Leukemia Cell Proliferation An in vivo drug treatment experiment was performed. Initial toxicity studies by chronic injection of PGMI-004A to nude mice for 4 weeks revealed that 100 mg/kg/day administered intraperitoneally is a well-tolerated dose. In addition, continuous treatment with PGMI-004A (100 mg/kg/day) for 7 days did not result in significant alteration in body weight, complete blood counts (CBC) or hematopoietic properties of nude mice. Histopathological analyses revealed that no notable differences between the vehicle-treated and PGMI-004A-treated groups were evident. Xenograft experiments were performed by injecting H1299 cells to nude mice. Six days post-injection, mice were divided into two groups (n=8/group) and treated with either PGMI-004A (100 mg/kg/day) or vehicle for 21 days. PGMI-004A treatment results in significantly decreased tumor growth and tumor size in treated mice compared with mice receiving vehicle control (FIG. 8A-8B, respectively). Moreover, treatment with PGMI-004A effectively inhibits PGAM1 enzyme activity in tumors in vivo in resected tumors from xenograft nude mice. These data together suggest that targeting PGAM1 by PGMI-004A inhibits PGAM1 in vivo, and that this inhibition causes specific toxicity to tumor cells.

Figure 8D:
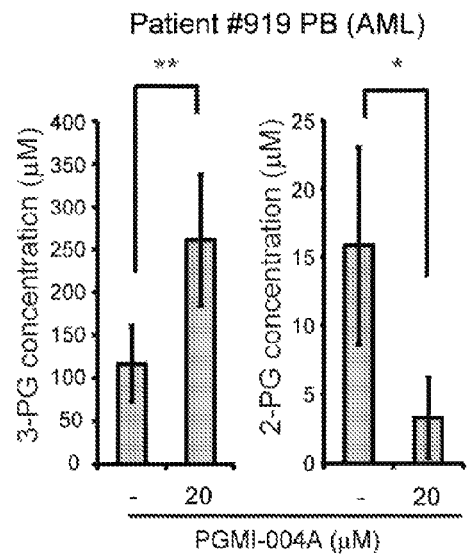
Figure 8E:
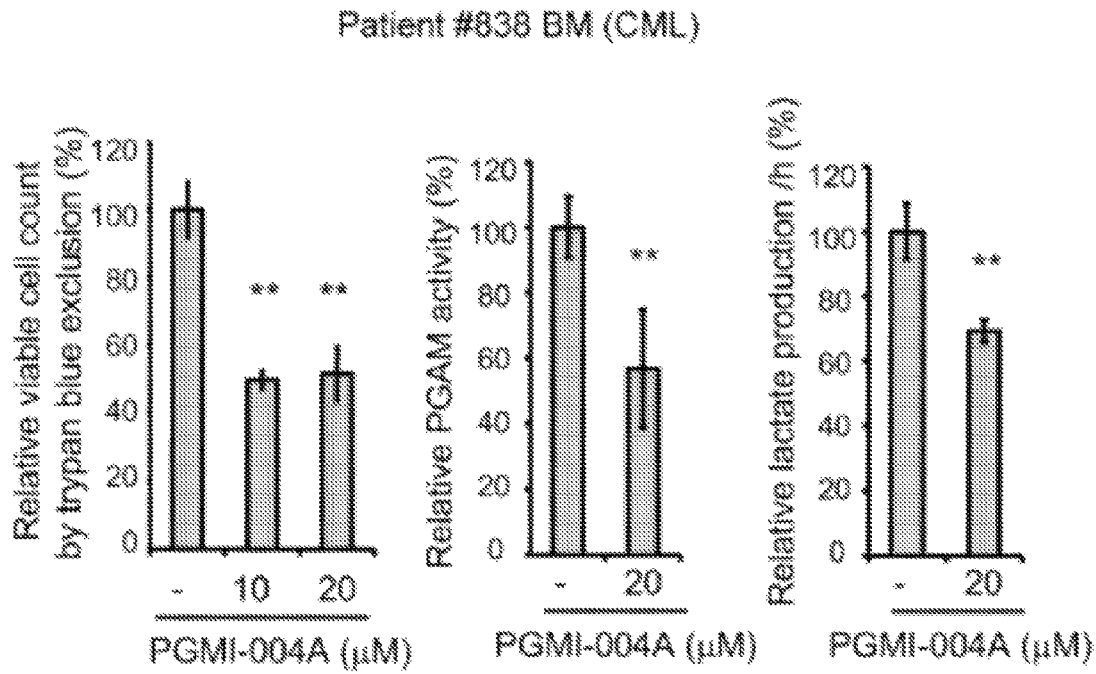
Figure 8F:
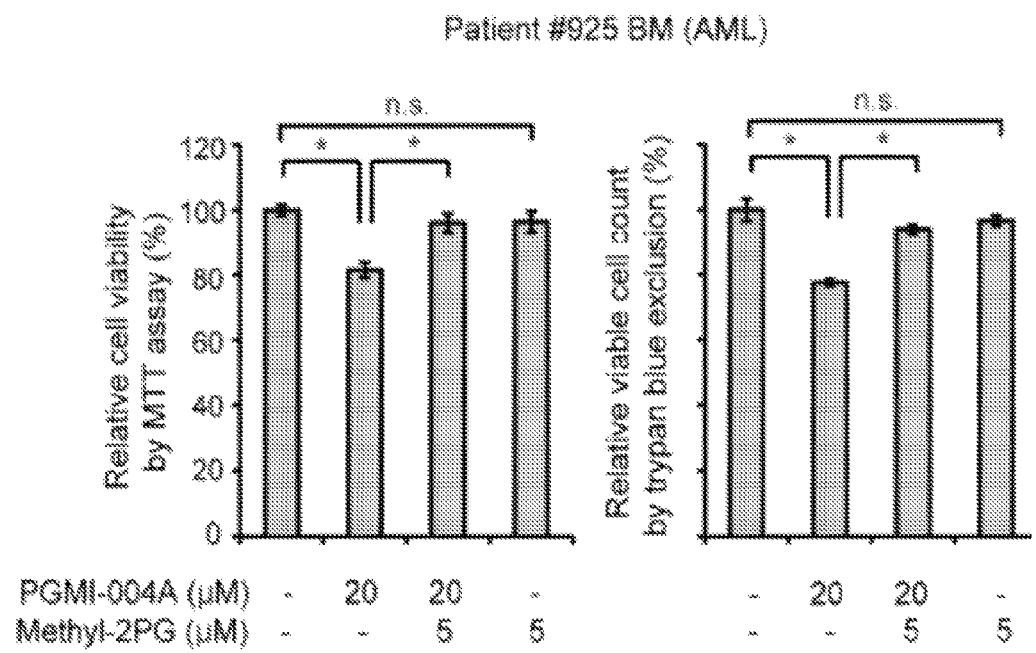
Figure 8G:
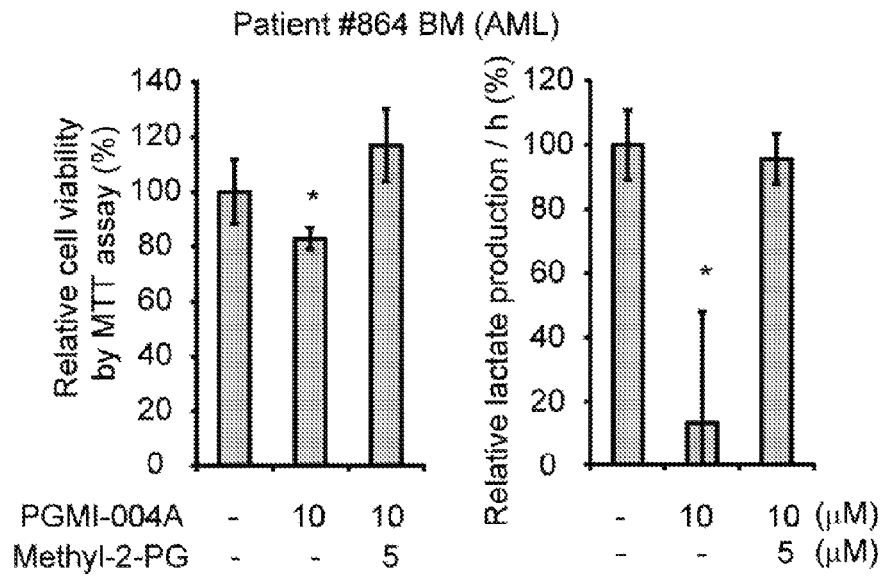
Figure 8H:
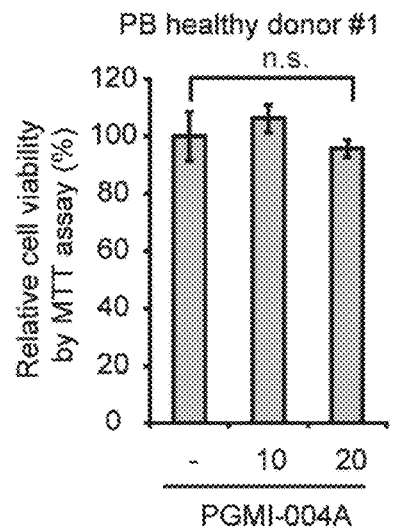
Figure 8I:
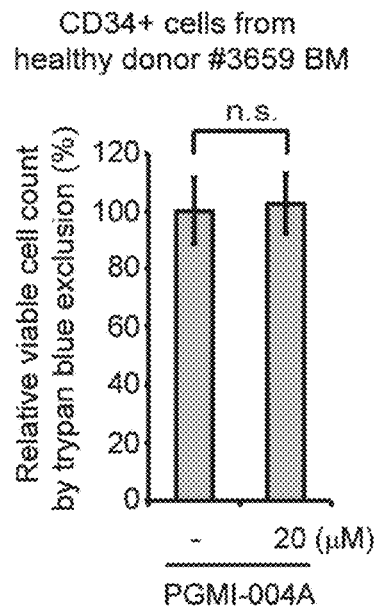

PGAM1 protein expression and enzyme activity levels are upregulated in primary leukemia cells from diverse AML, CML and B-ALL patients (n=12), compared to control peripheral blood cells from healthy donors (n=4) (FIG. 8C). Consistent with the observations in cancer cell lines, inhibiting PGAM1 by PGMI-004A treatment results in increased 3-PG and decreased 2-PG levels in primary leukemia cells from a representative AML patient (FIG. 8D). PGMI-004A treatment also results in decreased cell viability and reduced PGAM1 activity and lactate production in the samples from 7 (1 CML and 6 AML) out of 8 leukemia patients. FIG. 8E show results using samples from CML and AML patients as representatives, respectively. Moreover, methyl-2-PG treatment rescues the decreased cell viability (FIG. 8F; 8G left) and lactate production (FIG. 8G right) in primary leukemia cells from representative AML patients. In addition, PGMI-004A treatment did not affect cell viability of mononucleocytes in peripheral blood samples from two healthy human donors (FIG. 8H) and CD34+ cells isolated from bone marrow samples from four healthy donors (FIG. 8I), suggesting promising anti-cancer potential of PGMI-004A with minimal toxicity to human blood cells.

PGAM1 Molecular Inhibitors

The attenuation of PGAM1 impacts tumor growth suggest PGAM1 as an anti-cancer target. A screening strategy was designed using coupled PGAM1 and enolase assays and identified three lead small molecule compounds, including alizarin, as PGAM1 inhibitors from a library of small molecule compounds obtained from the Developmental Therapeutic Program of NIH/NCI (FIG. 9E). Alizarin (FIG. 9E; top) is a 1,2-dihydroxyanthraquinone. Treatment with alizarin results in decreased proliferation of H1299 cells in a dose-dependent manner.

Figure 9A:
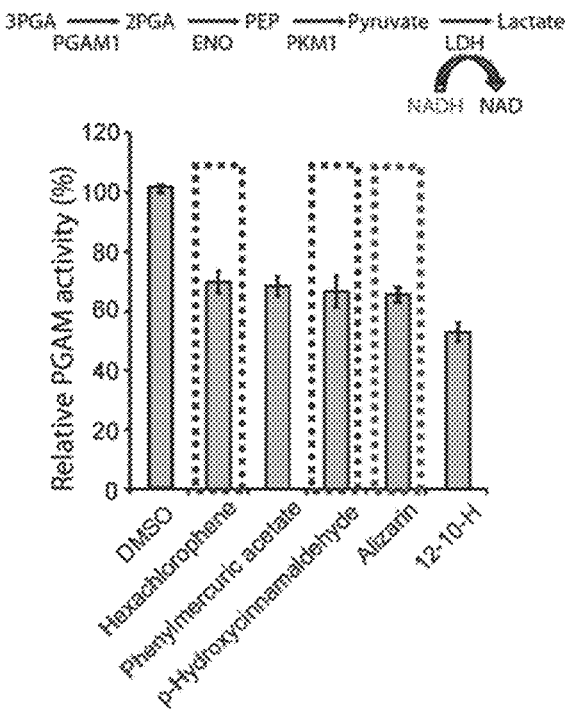
FIGS. 9A-E illustrate and show data on alizarin and alizarin Red S as PAGM1 inhibitors. (A-B) Screen identifies alizarin and its derivative alizarin Red S as PGAM1 inhibitors. Primary screen was performed as an in vitro PGAM1 assay using recombinant PGAM1 identified 5 lead compounds as potential PGAM1 inhibitors (A). Secondary screen was performed as an in vitro enolase assay using recombinant enolase to exclude potential off target effects of the lead compounds (B). Three compounds were identified as PGAM1 inhibitors including hexachlorophene, p-hydroxycinnamaldehyde and alizarin. (C) Inhibitory potency of different lead compounds including Alizarin, hexachlorophene and p-hydroxycinnamaldehyde in human leukemia KG1a cells. Cells were treated with individual compounds for 4 h. (D) Cell viability of KG1a cells in the presence of increasing concentrations of Alizarin (72 h). Cell viability was determined by trypan blue exclusion. (E) Chemical structures of commercially available alizarin derivatives. (F) Treatment with alizarin derivatives including 1,2,7-trihydroxyanthraquinone (#3); alizarin Red S (#5) and acid alizarin blue BB (#8) inhibit PGAM1 enzyme activity in the in vitro PGAM1 assay.
Figure 9B:
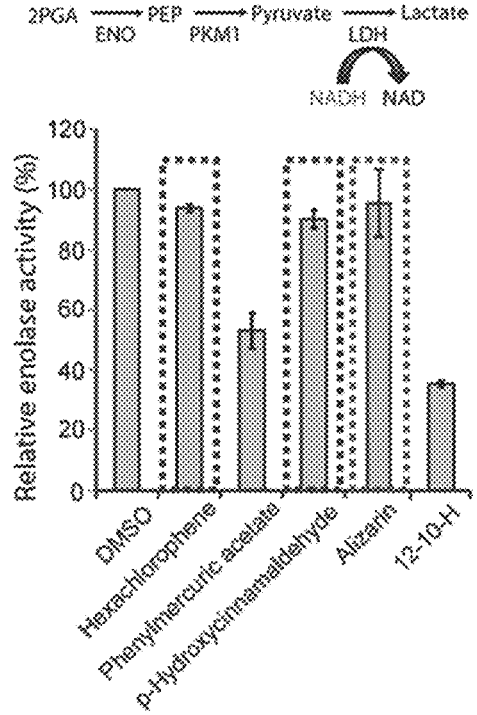
Figure 9C:
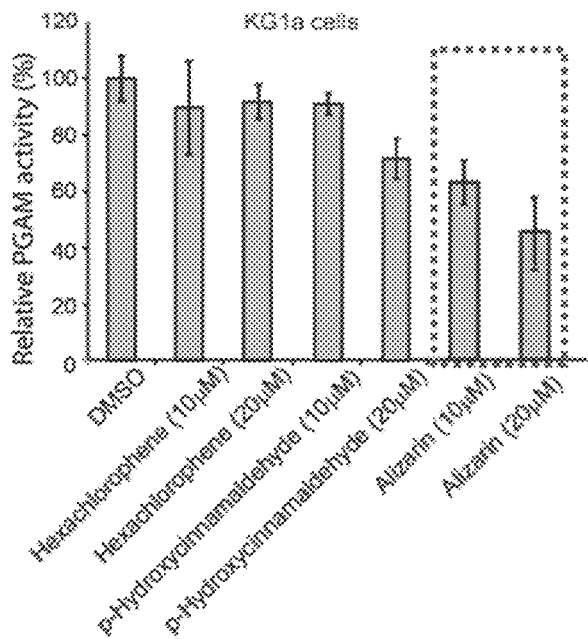
Figure 9D:
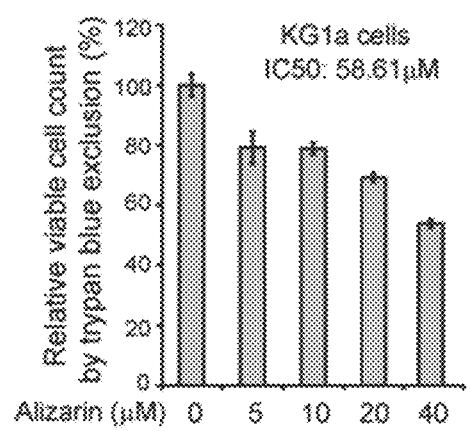
Figure 9F:
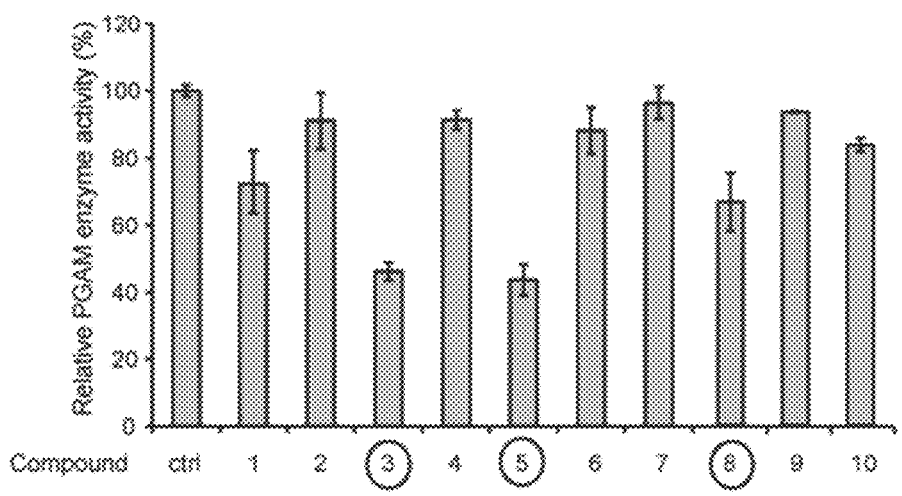
Figure 9E:
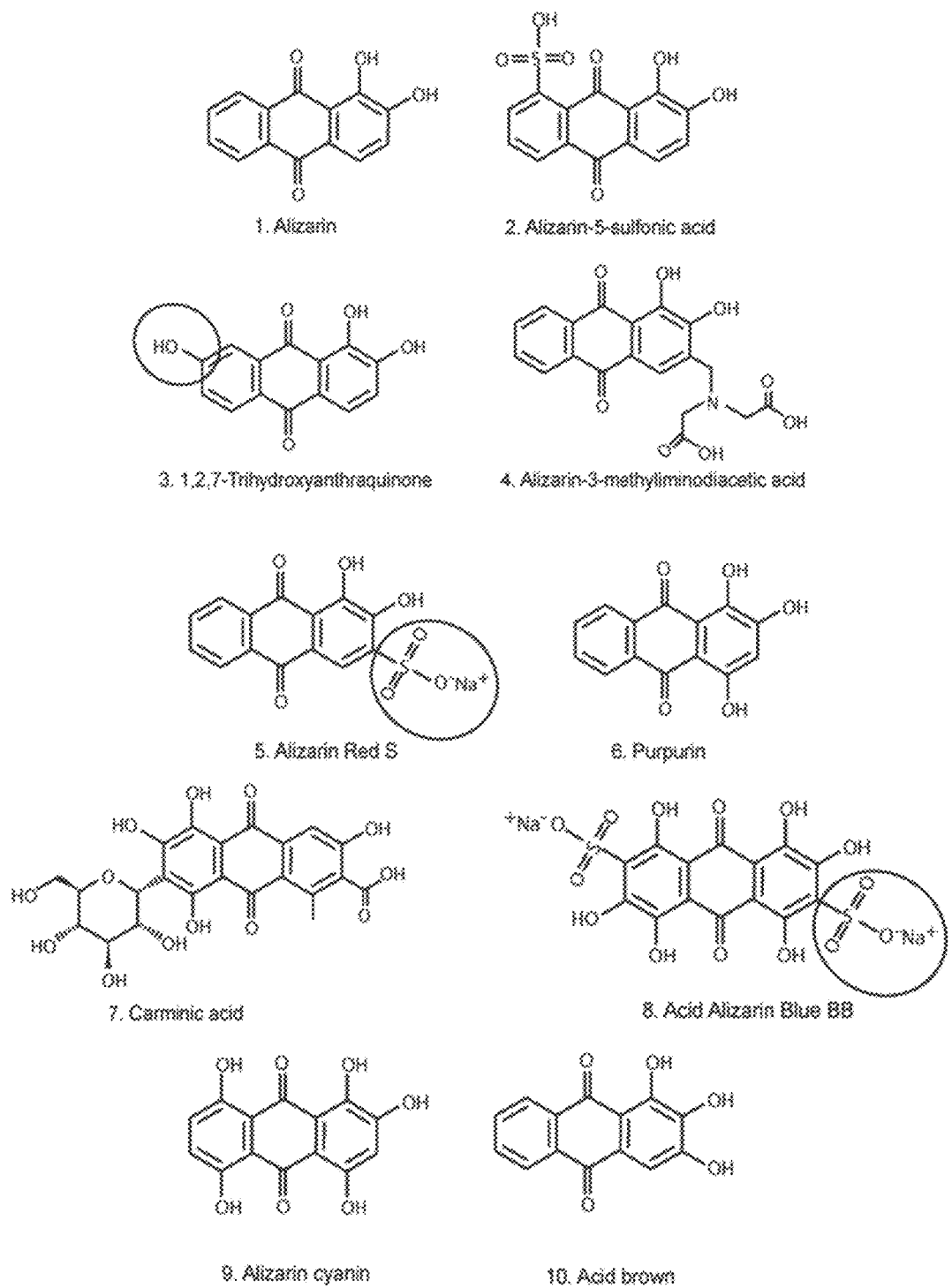

A group of alizarin derivatives were screened and found that alizarin Red S (FIG. 9E; middle) has more potent PGAM1 inhibitory potential compared to alizarin (FIG. 9F). Co-crystallization and structural analyses revealed that alizarin Red S binds to the active site of PGAM1 suggesting the molecular mechanism by which alizarin and alizarin Red S inhibit PGAM1. Modeling and analyses of unbiased Fo-Fc difference density maps was conducted, allowing us to determine the orientation of alizarin Red S. Based on this analysis, the conjugated ring system of anthracene-9,10-dione was determined to be is the main structure of alizarin Red S, which binds to the pocket of PGAM1 catalytic site by forming hydrogen bonds between its two oxygen molecules on ring C and PGAM1 residues Phe22 and Arg116. The sulfonic acid group of alizarin Red S also forms strong hydrogen bonds with Ser23 and Arg62, which further stabilizes the interaction between PGAM1 and alizarin Red S.

Figure 10A:
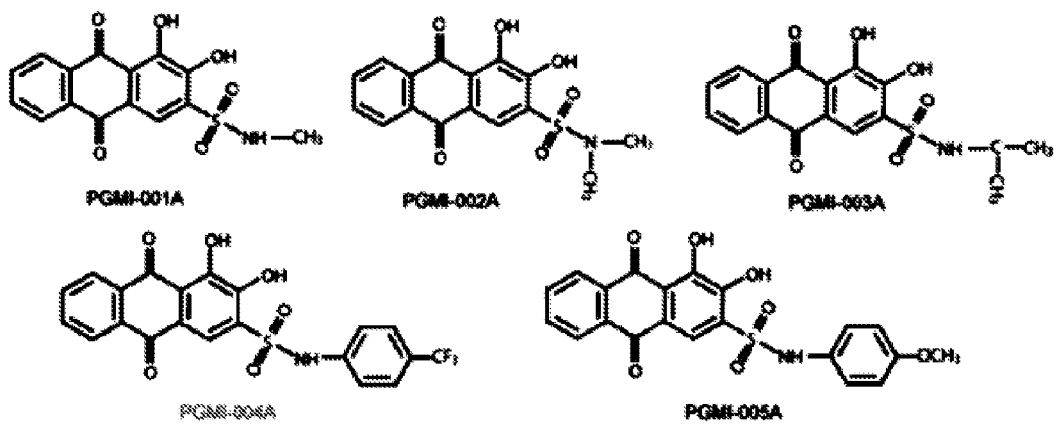
FIGS. 10A-I illustrate certain embodiments and show data on PAGM1 inhibitors. (A) Chemical structures of specially designed derivatives of alizarin Red S, including PGMI-001A to 5A. (B) Inhibitory effects of diverse alizarin derivatives on enzyme activity of recombinant PGAM1 in an in vitro PGAM1 enzyme assay. (C) PGMI-004A demonstrates more potent activity in regard to PGAM1 inhibition in KG1a cells compared to controls including alizarin, alizarin Red S and PGMI-001A (2 h). (D) Rescue of 2-PG levels in PGMI-004A-treated H1299 cells by treatment with methyl-2-PG results in increased lactate production compared with control cells treated with PGMI-004A, while this rescued phenotype was abolished when enolase was knocked down or inhibited by specific inhibitor NaF. (E-H) Effect of PGMI-004A treatment on cell proliferation of lung cancer H1299 (D), leukemia KG1a (E) and head and neck cancer 212LN cells (F) and diverse human leukemia cells (G). Cells were treated with increasing concentrations of PGMI-004A for 72 h. (I) PGMI-004A treatment does not affect cell proliferation of human foreskin fibroblasts (HFF), human HaCaT keratinocyte cells and human melanocyte PIG1 cells.
Figure 10B:
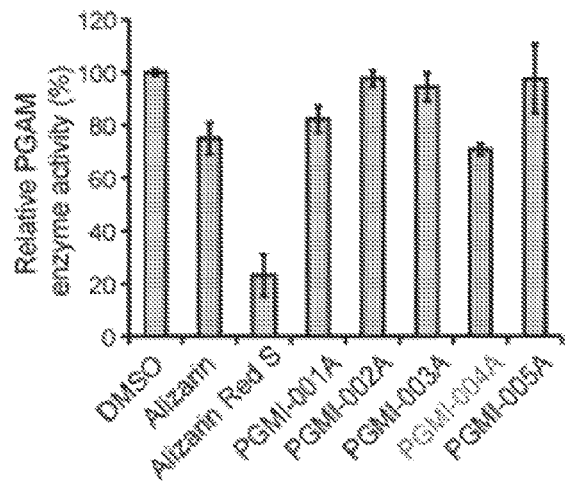
Figure 10C:
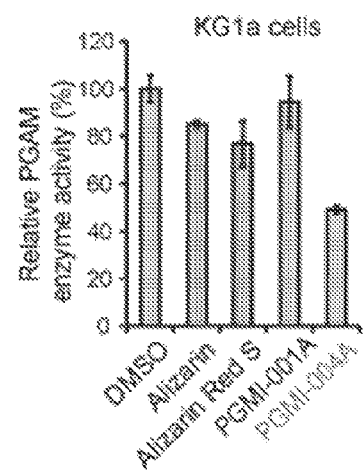
Figure 10D:
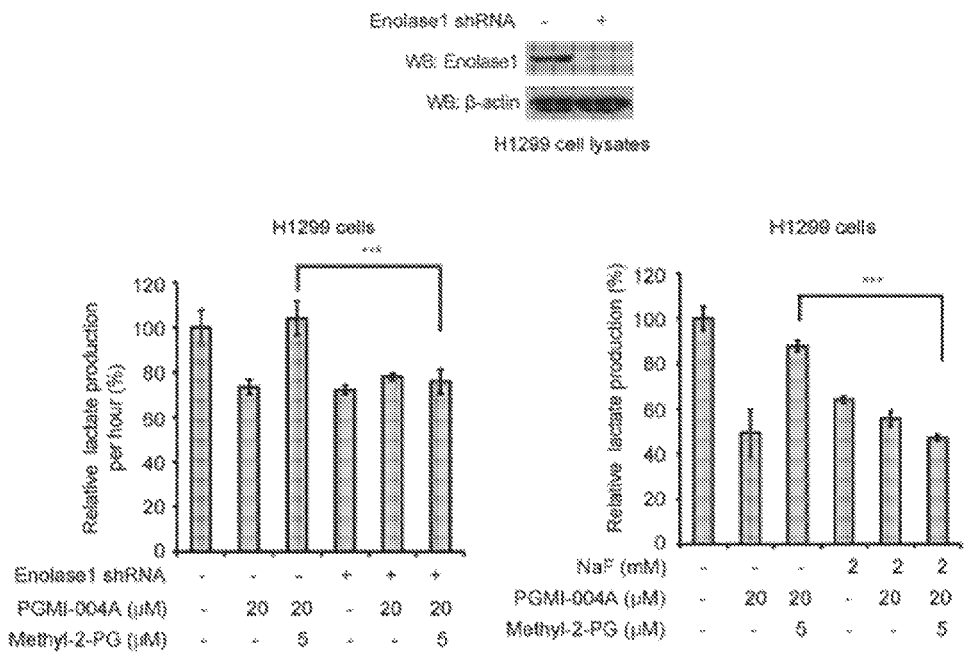
Figure 10E:
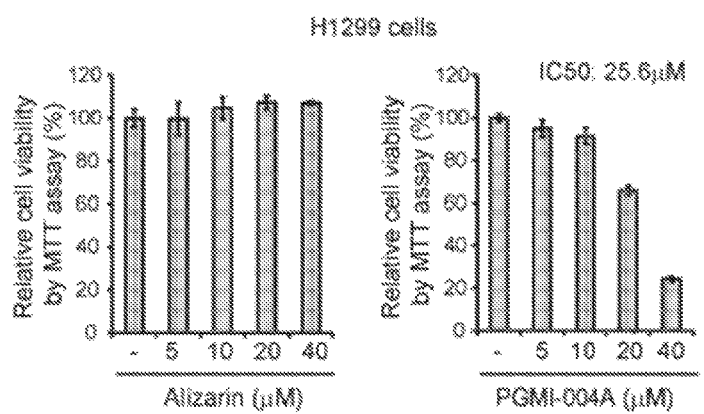
Figure 10F:
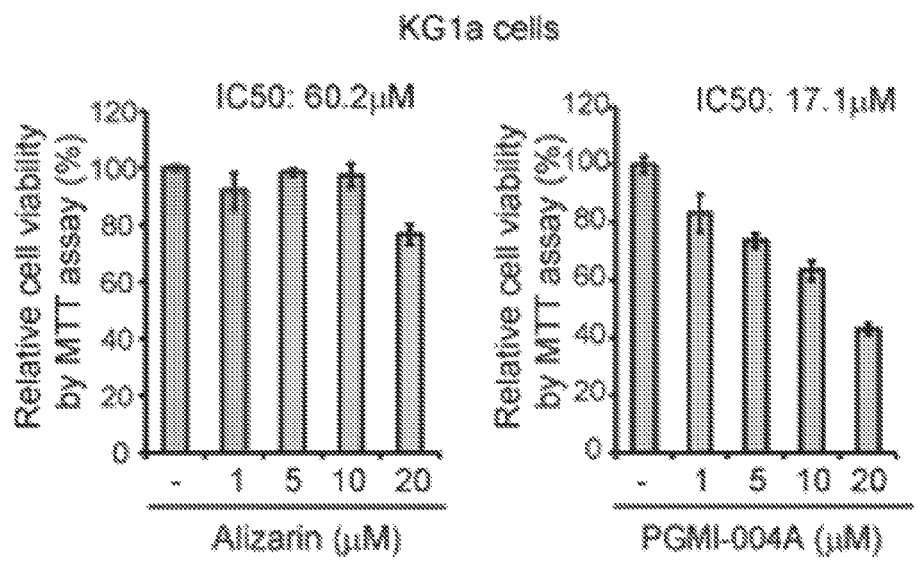
Figures 10G, 10H:
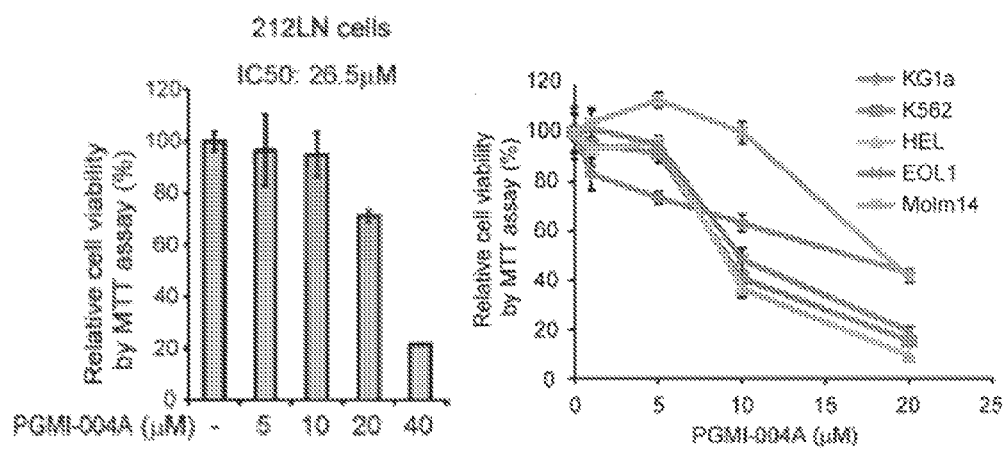
Figure 10I:
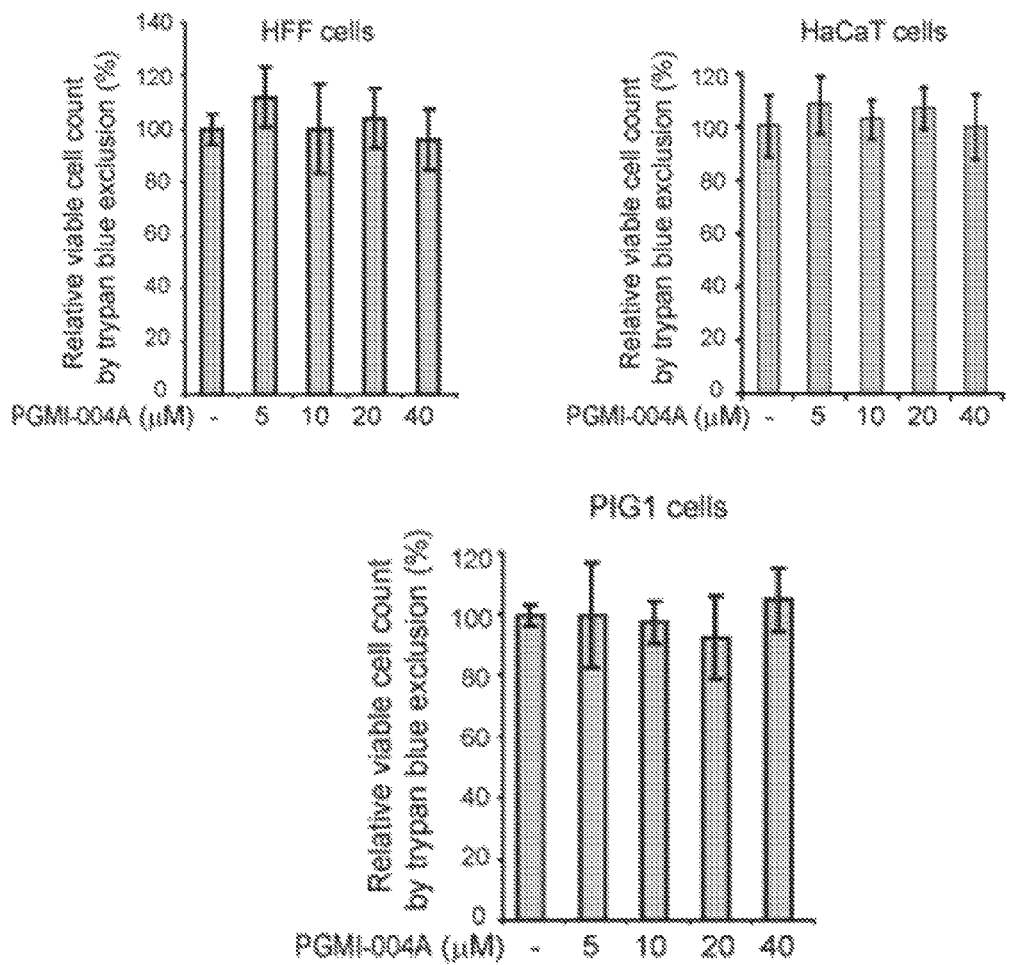
Figure 11A:
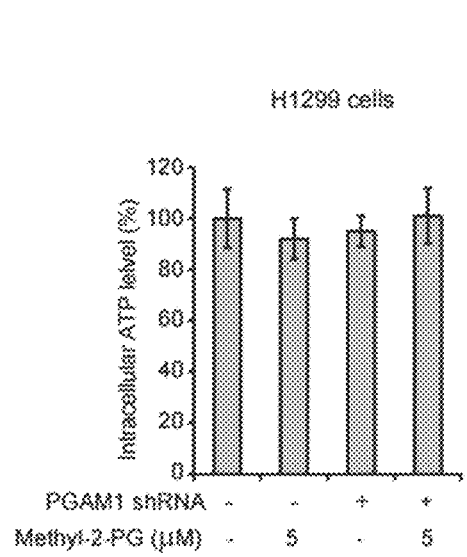
FIGS. 11A-E show data indicating rescue of reduced 2-PG levels by methyl-2PG treatment results in decreased 3-PG levels and rescues decreased biosynthesis and cell proliferation in PGAM1 knockdown breast cancer cells. (A) Intracellular ATP levels in control and PGAM1 knockdown H1299 cells in the presence and absence of methyl-2-PG. (B-E) Effect of treatment with methyl-2-PG on PPP flux (B) and biosynthesis of RNA (C) and lipids (D), as well as cell proliferation (E) in MDA-MB231 cells with stable knockdown of PGAM1 compared to control cells.
Figure 11B:
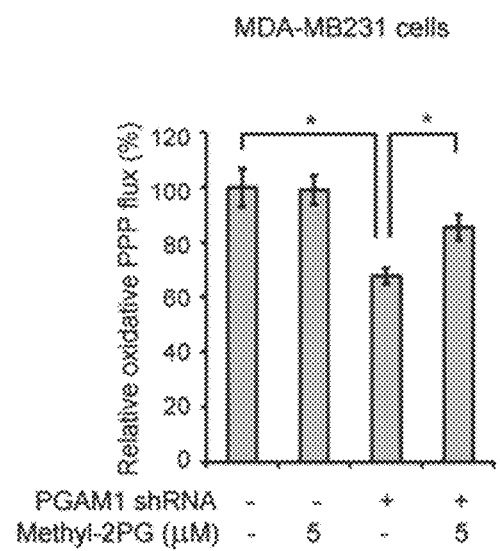
Figure 11C:
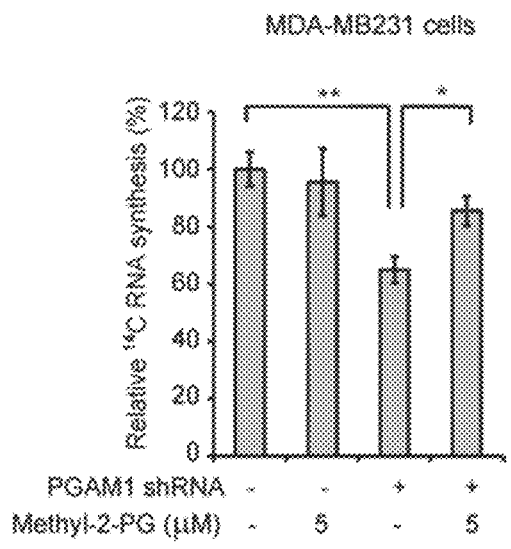
Figure 11D:
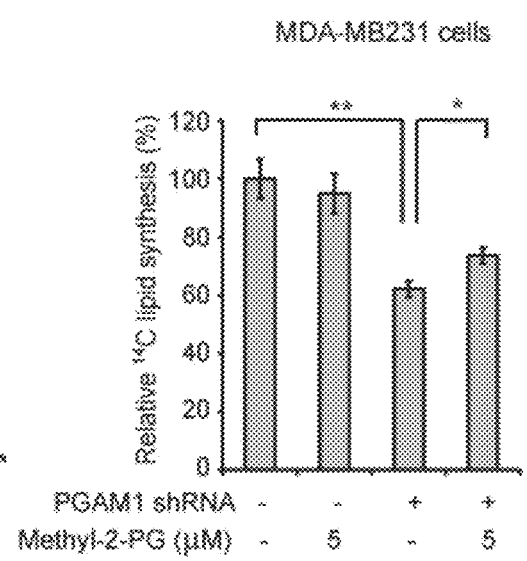
Figure 11E:
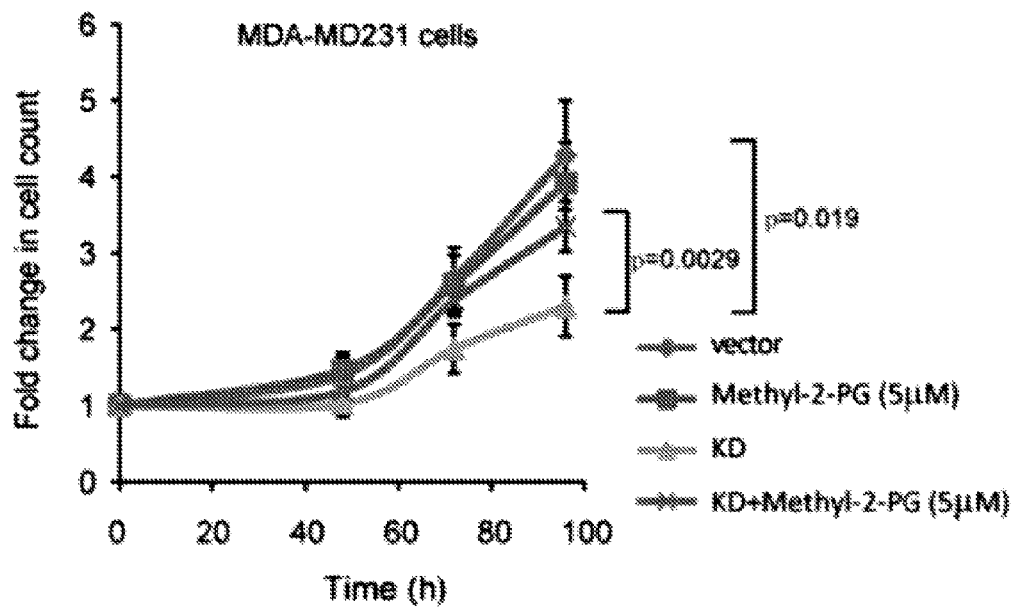
Figures 12A, 12B:
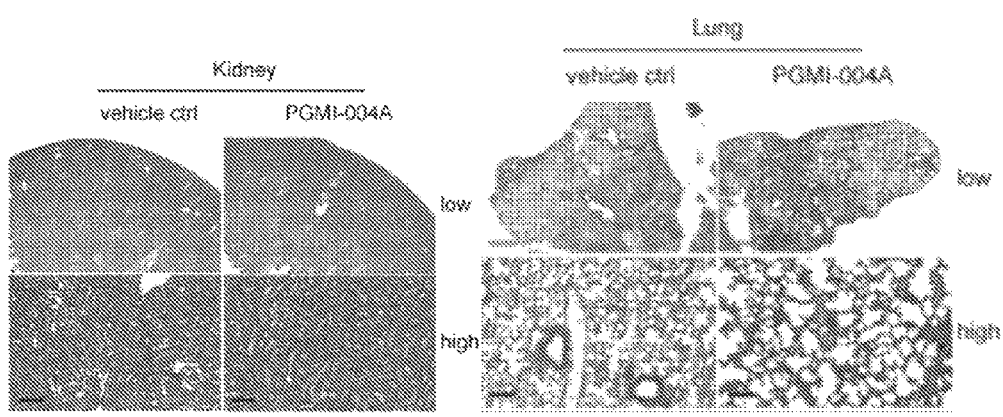
Figure 12F:
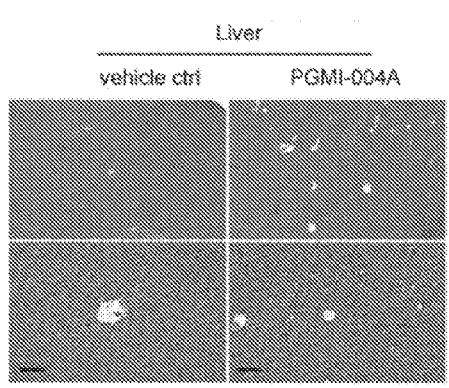
Figure 12F:
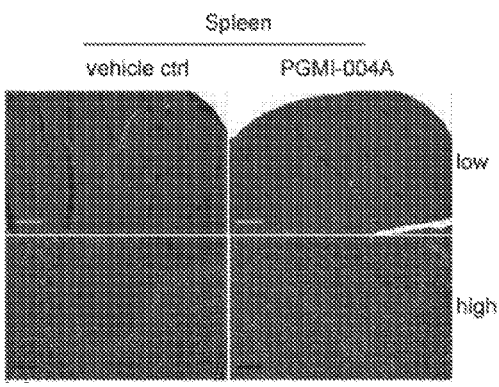
Figure 12F:
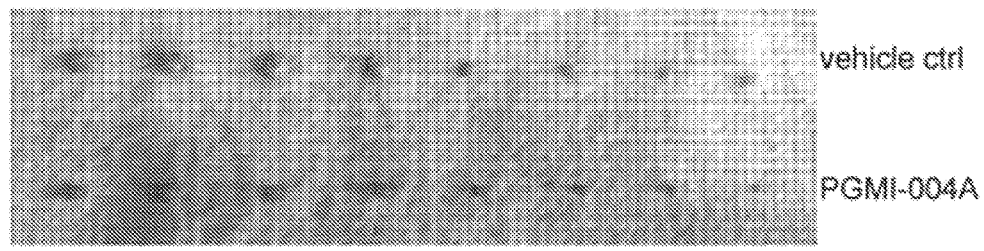
Figure 12E:
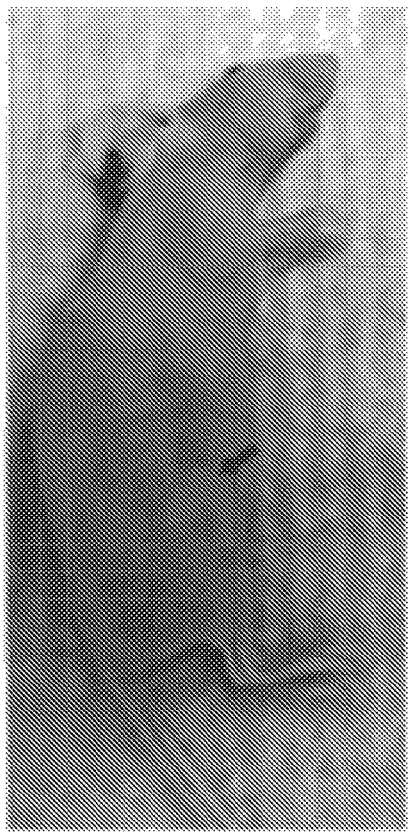
Figure 12E:
Figure 12E:
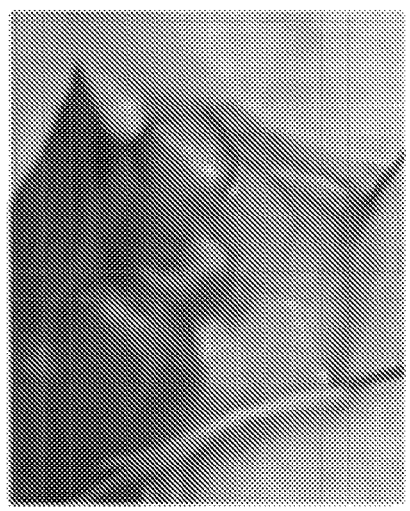
Figure 12E:

Since both alizarin and alizarin Red S are rather hydrophilic and may have low cell membrane permeability, a group of alizarin Red S derivatives were designed by adding hydrophobic groups through a sulfonamide bond (FIG. 10A). Such a sulfonamide bond would be hydrolyzed by esterase inside of cells and the active sulfonic acid group would be exposed to inhibit PGAM1. These compounds were tested and identified one derivative that was named PGAM1 inhibitor 004A (PGMI-004A) (FIG. 10A; bottom). Although PGMI-004A does not show improved inhibitory effect on PGAM1 compared to alizarin and alizarin Red S in the in vitro PGAM1 assay using purified recombinant PGAM1, PGMI-004A demonstrates enhanced potency to inhibit PGAM1 in leukemia KG1a cells compared to its parental compounds (FIG. 10C). This may be due to the fact that PGMI-004A is more hydrophobic than alizarin and alizarin Red S which confers better cell permeability. PGMI-004A treatment results in decreased cell proliferation of cancer cells including H1299 (FIG. 10E), KG1a (FIG. 10F) and 212LN cells (FIG. 10G).

The invention claimed is:

1. A compound of Formula I,

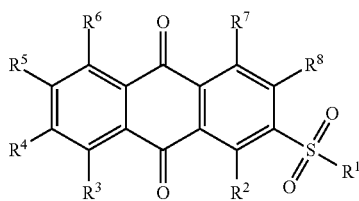

Formula I prodrug, ester, or salt thereof wherein:
$R^1$ is amino optionally substituted with one or more, the same or different, $R^9$;
$R^7$ is hydroxy;
$R^8$ is hydroxy;
$R^2$, $R^3$, $R^4$, $R^5$, and $R^6$, are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^4$, $R^5$, and $R^6$, are optionally substituted with one or more, the same or different, $R^9$;
$R^9$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{11}$;
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^1$ is amino and is substituted with an aryl ring, wherein the aryl ring is optionally substituted with one or more, the same or different $R^{10}$.

3. The compound of claim 1, wherein $R^1$ is amino and is substituted with an aryl ring, wherein the aryl ring substituted in the para position with an alkyl, wherein the alkyl group is optionally substituted with one or more, the same or different $R^{11}$.

4. The compound of claim 1, wherein $R^1$ is amino and is substituted with an aryl ring, wherein the aryl ring substituted in the para position with a methyl, wherein the methyl group is optionally substituted with one or more, the same or different $R^{11}$.

5. The compound of claim 1, wherein $R^1$ is amino and is substituted with an aryl ring, wherein the aryl ring substituted in the para position with a methyl, wherein the methyl group is substituted with one or more, the same or different halogens.

6. A pharmaceutical composition comprising a compound of claim 1 or a pharmaceutically acceptable salt thereof and a pharmaceutically acceptable excipient.

7. The pharmaceutical composition of claim 6, further comprising a second therapeutic agent.

8. A compound 3,4-dihydroxy-9,10-dioxo-N-(4-(trifluoromethyl)phenyl)-9,10-dihydroanthracene-2-sulfonamide or salts thereof.

9. A pharmaceutical composition comprising a compound of claim 8 or pharmaceutically acceptable salt thereof and a pharmaceutically acceptable excipient.

10. The pharmaceutical composition of claim 9, further comprising a second therapeutic agent.

11. The pharmaceutical composition of claim 9 in the form of a tablet, pill, or capsule.

12. The pharmaceutical composition of claim 9 in the form of a physiologically acceptable sterile aqueous solution comprising a buffering agent or isotonic agent.

13. The pharmaceutical composition of claim 9 wherein the pharmaceutically acceptable excipient is selected from ethanol, propylene glycol, polyethylene glycol, glycerol, olive oil, sesame oil, viscoleo, and ethyl oleate.

14. The pharmaceutical composition of claim 9 wherein the pharmaceutically acceptable excipient is selected from sodium citrate, dicalcium phosphate, starch, lactose, sucrose, glucose, mannitol, silicic acid, carboxymethylcellulose, alginate, gelatin, polyvinylpyrrolidone, acacia, calcium carbonate, alginic acid, sodium carbonate, paraffin, cetyl alcohol, glycerol monostearate, kaolin, bentonite, talc, calcium stearate, magnesium stearate, and sodium lauryl sulfate.

15. The pharmaceutical composition of claim 6 in the form of a tablet, pill, or capsule.

16. The pharmaceutical composition of claim 6 in the form of physiologically acceptable sterile aqueous solution comprising a buffering agent or isotonic agent.

17. The pharmaceutical composition of claim 6 wherein the pharmaceutically acceptable excipient is selected from ethanol, propylene glycol, polyethylene glycol, glycerol, olive oil, sesame oil, viscoleo, and ethyl oleate.

18. The pharmaceutical composition of claim 6 wherein the pharmaceutically acceptable excipient is selected from sodium citrate, dicalcium phosphate, starch, lactose, sucrose, glucose, mannitol, silicic acid, carboxymethylcellulose, alginate, gelatin, polyvinylpyrrolidone, acacia, calcium carbonate, alginic acid, sodium carbonate, paraffin, cetyl alcohol, glycerol monostearate, kaolin, bentonite, talc, calcium stearate, magnesium stearate, and sodium lauryl sulfate.

* * * * *

SEQUENCE LISTING

```
<160> NUMBER OF SEQ ID NOS: 1

<210> SEQ ID NO 1
<211> LENGTH: 59
<212> TYPE: DNA
<213> ORGANISM: Homo sapiens
```

```
<400> SEQUENCE: 1
ccggcaagaa cttgaagcct atcaactcga gttgataggc ttcaagttct tgttttttg     59
```